(12) United States Patent
Hattori et al.

(10) Patent No.: US 7,928,264 B2
(45) Date of Patent: Apr. 19, 2011

(54) AMINOALCOHOL DERIVATIVES

(75) Inventors: Kouji Hattori, Chuo-ku (JP); Susumu Toda, Chuo-ku (JP); Kenichi Washizuka, Chuo-ku (JP); Shinji Ito, Chuo-ku (JP); Daisuke Tanabe, Chuo-ku (JP); Takanobu Araki, Chuo-ku (JP); Minoru Sakurai, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 1102 days.

(21) Appl. No.: 11/547,847

(22) PCT Filed: Sep. 20, 2005

(86) PCT No.: PCT/JP2005/017669
§ 371 (c)(1),
(2), (4) Date: Oct. 6, 2006

(87) PCT Pub. No.: WO2006/033446
PCT Pub. Date: Mar. 30, 2006

(65) Prior Publication Data
US 2008/0039506 A1    Feb. 14, 2008

(30) Foreign Application Priority Data

Sep. 21, 2004  (AU) .................................. 2004905450
Feb. 21, 2005  (AU) .................................. 2005900789

(51) Int. Cl.
*C07C 213/00* (2006.01)
(52) U.S. Cl. ..................... 564/339; 546/304; 546/335
(58) Field of Classification Search ............... 564/339
See application file for complete search history.

(56) References Cited

U.S. PATENT DOCUMENTS

| | | | |
|---|---|---|---|
| 5,232,946 | A | 8/1993 | Hurnaus et al. |
| 7,037,938 | B2 * | 5/2006 | Hattori et al. ............... 514/534 |
| 7,417,060 | B2 * | 8/2008 | Hattori et al. ............... 514/357 |
| 7,629,366 | B2 * | 12/2009 | Hattori et al. ............... 514/357 |
| 2004/0106653 | A1 | 6/2004 | Sakurai et al. |
| 2005/0137236 | A1 | 6/2005 | Hattori et al. |
| 2006/0100252 | A1 | 5/2006 | Hattori et al. |

FOREIGN PATENT DOCUMENTS

| WO | WO 90/06299 | 6/1990 |
|---|---|---|
| WO | WO 02/10141 A1 | 2/2002 |
| WO | 02 32897 | 4/2002 |
| WO | 02 094770 | 11/2002 |
| WO | 2004 002939 | 1/2004 |

OTHER PUBLICATIONS

Hcaplus 2004:20641, Jan. 8, 2004, "Preparation of alpha-aryl/pyridinyl ethanolamines as selective Beta 3 adrenergic receptor agonists", Hattori et. al.*

Hcaplus 1989:477643 Abstract, "Preparation of new phenylethanolamines and pharmaceuticals containing them", Hurnaus et. al., 1988.*
Patani et. al., "Bioisosterism: A Rational Approach in Drug Design", Chem. Rev. 1996, pp. 3147-3176.*
H. Elizabeth Taylor, et al., "1-Alkylcarbonyloxymethyl prodrugs of 5-fluorouracil (5-FU): synthesis, physicochemical properties, and topical delivery of 5-FU", Journal of Pharmaceutical Sciences, vol. 87, No. 1, Jan. 1998, pp. 15-20.
M.D. Mashkovskiy, "Medicaments", Moscow, Medicine, 2001, vol. 1, p. 7.
M. Imanishi et al., J. Med. Chem, 2008, vol. 51, pp. 1925-1944.

* cited by examiner

*Primary Examiner* — Janet L Andres
*Assistant Examiner* — Heidi Reese
(74) *Attorney, Agent, or Firm* — Oblon, Spivak, McClelland, Maier & Neustadt, L.L.P.

(57) ABSTRACT

The present invention relates to a compound of the formula [I]: wherein (a), in which —Y—, $R^4$, $R^5$ and $R^6$ are $^4$ $R^5$ each as defined in the description, etc., $R^1$ is hydrogen, halogen, lower alkyl, hydroxy, etc., $R^2$ is hydrogen, lower alkyl or hydroxy(lower)alkyl, $R^3$ is hydrogen or an amino protective group, $20^{R7}$ is hydrogen, lower alkyl, cyclo(lower)alkyl, lower R9 alkenyl, —Z—$R^9$ or (b), in which —Z— is —O—, —S—, $R^9$—SO— or —SO$_2$—, and each $R^9$ is independently hydrogen, lower alkyl, cyclo(lower)alkyl, etc., and $R^8$ is -D-E-$R^{10}$, in which -D- is —CONHSO$_2$— or —SO$_2$NHCO—, E is bond or lower alkylene, and $R^{10}$ is halogen, cyano, carboxy, etc., or a prodrug thereof or a salt thereof. The compound [I] of the present invention and pharmaceutically acceptable salts thereof are useful for the prophylactic and/or the therapeutic treatment of ulcer, overactive bladder, and the like.

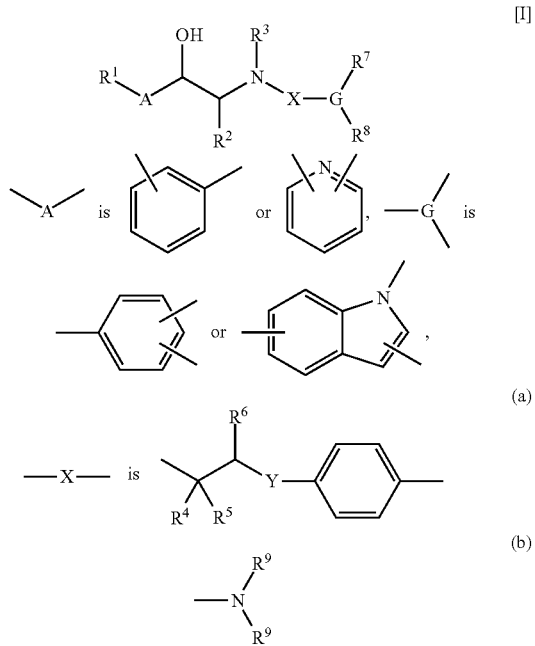

27 Claims, No Drawings

AMINOALCOHOL DERIVATIVES

CROSS REFERENCES TO RELATED APPLICATIONS

This application is a 371 of International Patent Application No. PCT/JP05/17669, filed on Sep. 20, 2005, and claims priority to Australian Patent Application No. 2004905450, filed on Sep. 21, 2004, and Australian Patent Application No. 2005900789, filed on Feb. 21, 2005.

FIELD OF THE INVENTION

This invention relates to new aminoalcohol derivatives and salts thereof which are beta-3 ($\beta_3$) adrenergic receptor agonists and useful as a medicament.

BACKGROUND OF THE INVENTION

International Publication No. WO 90/06299, published Jun. 14, 1990, describes derivatives of phenylethanolamines as having an effect on the metabolism, preferably reduction of the blood sugar level and body fat, International Publication No. WO 02/32897, published Apr. 25, 2002, describes derivatives of alpha-aryl ethanolamines useful as $\beta_3$ adrenergic receptor agonists, and International Publication Nos. WO 2004/002939, published Jan. 8, 2004, and WO 2005/061433, published Jul. 7, 2005, describe aminoalcohol derivatives useful as $\beta_3$ adrenergic receptor agonist.

DISCLOSURE OF THE INVENTION

This invention relates to new aminoalcohol derivatives which are $\beta_3$ adrenergic receptor agonists and salts thereof.

More particularly, it relates to new aminoalcohol derivatives and salts thereof which are useful for the treatment and/or prevention of gastro-intestinal disorders, ulcer, overactive bladder, micturition disorders, pancreatitis, obesity, diabetes, etc., to processes for the preparation thereof, to a pharmaceutical composition comprising the same and to a method of using the same therapeutically in the treatment and/or prevention of the aforesaid disorders in a human being or an animal.

One object of this invention is to provide new and useful aminoalcohol derivatives and salts thereof which are useful for the treatment and/or prevention of the aforesaid disorders.

Another object of this invention is to provide processes for the preparation of said aminoalcohol derivatives and salts thereof.

A further object of this invention is to provide a pharmaceutical composition comprising, as an active ingredient, said aminoalcohol derivatives and salts thereof.

Still further object of this invention is to provide a therapeutical method for the treatment and/or prevention of the aforesaid diseases in a human being or an animal, using said aminoalcohol derivatives and salts thereof.

The object aminoalcohol derivatives of this invention are new and can be represented by compound of the following formula [I]:

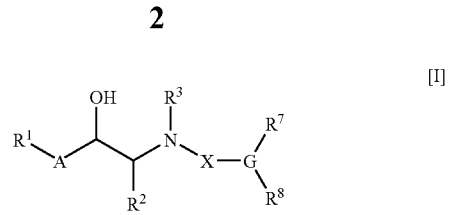

wherein

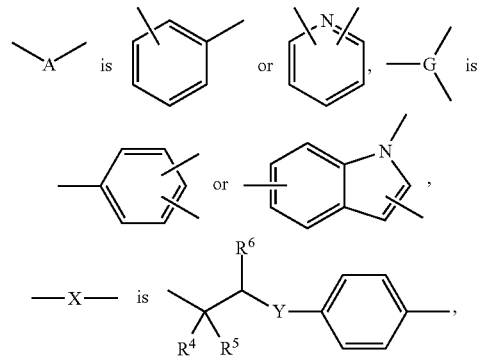

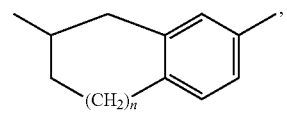

in which —Y— is bond, —O—, —NH— or —CH$_2$—, and
$R^4$, $R^5$ and $R^6$ are each independently hydrogen, lower alkyl or hydroxy(lower)alkyl, or

in which n is 0, 1 or 2, $R^1$ is hydrogen, halogen, lower alkyl, hydroxy, lower alkoxy, aryloxy, nitro, amino, (mono or di)(lower)alkylamino or arylamino, $R^2$ is hydrogen, lower alkyl or hydroxy(lower)alkyl, $R^3$ is hydrogen or an amino protective group, $R^7$ is hydrogen, lower alkyl, cyclo(lower)alkyl, lower alkenyl, —Z—R$^9$ or $$-\text{N}\begin{matrix}R^9\\R^9\end{matrix},$$

in which —Z— is —O—, —S—, —SO— or —SO$_2$—, and
each $R^9$ is independently hydrogen, lower alkyl, cyclo(lower)alkyl, lower alkenyl, carbamoyl, lower alkylcarbamoyl, lower alkylsulfonyl, aryl or a heterocyclic group, and $R^8$ is -D-E-R$^{10}$, in which -D- is —CONHSO$_2$— or —SO$_2$NHCO—, E is bond or lower alkylene, and $R^{10}$ is halogen, cyano, carboxy, lower alkoxycarbonyl, carbamoyl, lower alkylcarbamoyl, a heterocyclic group, —O—R$^{11}$, —S—R$^{11}$ or

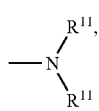
in which
each $R^{11}$ is independently hydrogen, lower alkyl, lower alkanoyl, lower alkoxycarbonyl or aryl(lower)alkyl,
or a prodrug thereof or a salt thereof.
According to this invention, the object compounds can be prepared by processes which are illustrated in the following schemes.
Process 1
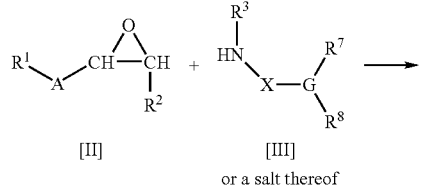
Process 2
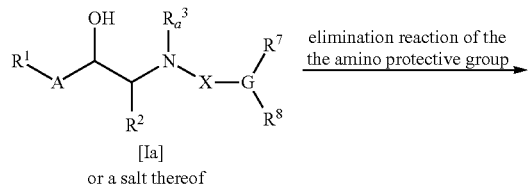
Process 3
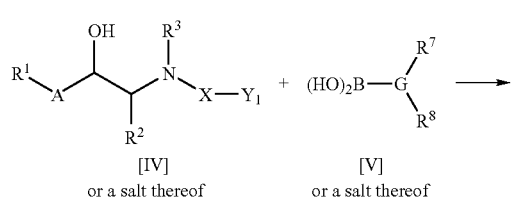
Process 4
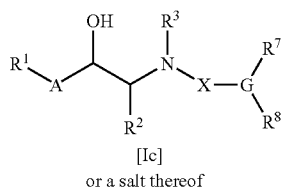
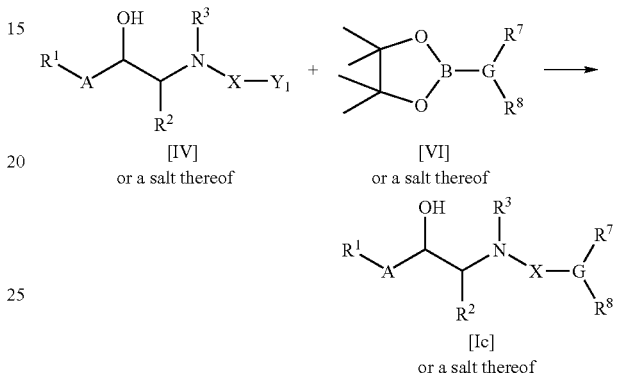
Process 5
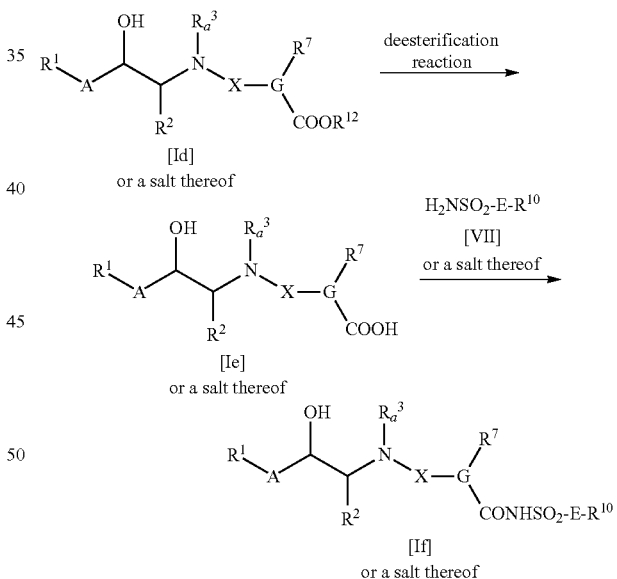
Process 6
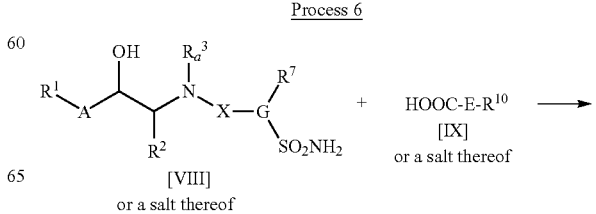

-continued

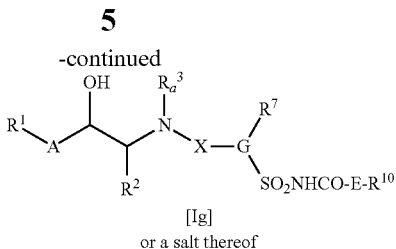

[Ig]

or a salt thereof wherein

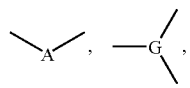

—X—, $R^1$, $R^2$, $R^3$, $R^7$, $R^8$, E and $R^{10}$ are each as defined above,
$R_a^3$ is an amino protective group,
$R^{12}$ is lower alkyl, and
$Y_1$ is a leaving group.

As to the starting compounds [II], [III], [Ia], [IV], [V], [VI], [Id], [VIII] and [IX], some of them are novel and can be prepared by the procedures described in the Preparations and Examples mentioned below or a conventional manner.

In the above and subsequent description of the present specification, suitable examples of the various definition to be included within the scope of the invention are explained in detail in the following.

The term "lower" is intended to mean a group having 1 to 8, preferably 1 to 7, more preferably 1 to 6, most preferably 1 to 4, carbon atom(s), unless otherwise indicated.

Suitable "lower alkyl" and "lower alkyl" moiety in the terms of "hydroxy(lower)alkyl", "(mono or di)(lower)alkylamino", "lower alkylcarbamoyl", "lower alkylsulfonyl" and "aryl(lower)alkyl" may include straight or branched one having 1 to 8, preferably 1 to 7, more preferably 1 to 6 carbon atom(s), such as methyl, ethyl, propyl, isopropyl, butyl, isobutyl, sec-butyl, tert-butyl, pentyl, isopentyl, 1-methylpentyl, tert-pentyl, neo-pentyl, hexyl, isohexyl, and the like, in which preferable one may be methyl, ethyl, propyl, isopropyl or isobutyl.

Suitable "lower alkoxy" and "lower alkoxy" moiety in the term of "lower alkoxycarbonyl" may include methoxy, ethoxy, propoxy, isopropoxy, butoxy, iso-butoxy, tert-butoxy, pentyloxy, tert-pentyloxy, hexyloxy, and the like, in which preferable one may be methoxy or tert-butoxy.

Suitable "lower alkanoyl" may include formyl, acetyl, propanoyl, butanoyl, 2-methylpropanoyl, pentanoyl, 2,2-dimethylpropanoyl, hexanoyl, and the like, in which preferable one may be acetyl.

Suitable "cyclo(lower)alkyl" may include cyclopropyl, cyclobutyl, cyclopentyl, cyclohexyl, cycloheptyl, cyclooctyl, and the like, in which preferable one may be cyclo($C_3$-$C_7$) alkyl, and more preferable one may be cyclopentyl, cyclohexyl or cycloheptyl.

Suitable "lower alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, 1-(or 2-)methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1-(or 2- or 3-)butenyl, and the like, in which preferable one may be $C_2$-$C_4$ alkenyl.

Suitable "lower alkylene" may include straight or branched alkylene having 1 to 6 carbon atoms, such as methylene, ethylene, trimethylene, 2,2-dimethyltrimethylene, 3,3-dimethyltrimethylene, tetramethylene, pentamethylene, hexamethylene and propylene, in which preferable one may be straight alkylene having 1 to 4 carbon atoms.

Suitable "halogen" may be fluoro, chloro, bromo and iodo, in which preferable one may be fluoro or chloro.

Suitable "aryl" and "aryl" moiety in the terms of "aryloxy", "arylamino" and "aryl(lower)alkyl" may include phenyl, naphthyl, indenyl, anthryl, and the like, in which preferable one may be phenyl.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.;

saturated 3 to 7-membered heteromonocyclic group containing 1 to 4 nitrogen atoms [e.g. pyrrolidinyl, imidazolidinyl, piperidyl, piperazinyl, homopiperazinyl, etc.];
unsaturated condensed heterocyclic group containing 1 to 5 nitrogen atoms, for example, indolyl, isoindolyl, indolizinyl, benzimidazolyl, quinolyl, isoquinolyl, imidazopyridyl, indazolyl, benzotriazolyl, tetrazolopyridazinyl [e.g. tetrazolo[1,5-b]pyridazinyl, etc.], quioxalinyl, etc.;
unsaturated 3 to 6-membered heteromonocyclic group containing an oxygen atom, for example, pyranyl, furyl, etc.;
saturated 3 to 6-membered heteromonocyclic group containing an oxygen atom, for example, 1H-tetrahydropyranyl, tetrahydrofuranyl, etc.;
unsaturated 3 to 6-membered heteromonocyclic group containing 1 to 2 sulfur atoms, for example, thienyl, etc.;
unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], oxazolinyl [e.g. 2-oxazolinyl, etc.], etc.;
saturated 3 to 6-membered heteromonocyclic group containing 1 to 2 oxygen atoms and 1 to 3 nitrogen atoms [e.g. morpholinyl, etc.];
unsaturated condensed heterocyclic group containing 1 to 2 oxygen atoms and 1 to 3 nitrogen atoms [e.g. benzofurazanyl, benzoxazolyl, benzoxadiazolyl, etc.];
unsaturated 3 to 6-membered heteromonocyclic group containing 1 to 2 sulfur atoms and 1 to 3 nitrogen atoms, for example, thiazolyl, thiadiazolyl [e.g. 1,2,4-thiadiazolyl, 1,3,4-thiadiazolyl, 1,2,5-thiadiazolyl, etc.], etc.;
saturated 3 to 6-membered heteromonocyclic group containing 1 to 2 sulfur atoms and 1 to 3 nitrogen atoms [e.g. thiazolidinyl, etc.];
unsaturated condensed heterocyclic group containing 1 to 2 sulfur atoms and 1 to 3 nitrogen atoms [e.g. benzothiazolyl, benzothiadiazolyl, etc.];
unsaturated condensed heterocyclic group containing 1 to 2 oxygen atoms [e.g. benzofuranyl, benzodioxolyl, chromanyl, etc.], and the like.

Suitable "leaving group" may include hydroxy, reactive group derived from hydroxy, and the like.

Suitable "reactive group derived from hydroxy" may include acid residue and the like.

Suitable "acid residue" may include halogen [e.g. fluoro, chloro, bromo, iodo], acyloxy [e.g. acetoxy, tosyloxy, mesyloxy, trifluoromethanesulfonyloxy, etc.], and the like.

Suitable example of "amino protective group" may be common amino protective group such as substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkyloxycarbonyl [e.g. benzyloxycarbonyl, p-nitro-benzyloxycarbonyl, etc.], substituted or unsubstituted arenesulfonyl [e.g. benzenesulfonyl, tosyl, etc.], nitrophenylsulfenyl, aryl(lower)alkyl [e.g. trityl, benzyl, etc.], and the like, in which preferable one is tert-butoxycarbonyl.

Suitable salts of the object aminoalcohol derivative [I] are pharmaceutically acceptable salts and include conventional non-toxic salts such as an inorganic acid addition salt [e.g. hydrochloride, hydrobromide, sulfate, phosphate, etc.], an organic acid addition salt [e.g. formate, acetate, trifluoroacetate, oxalate, maleate, fumarate, tartrate, citrate, methanesulfonate, benzenesulfonate, toluenesulfonate, etc.], an alkali metal salt [e.g. sodium salt, potassium salt, etc.], and the like, in which preferable one is hydrochloride.

The Processes 1 to 6 for preparing the object compounds of the present invention are explained in detail in the following.

Process 1

The object compound [I] or a salt thereof can be prepared by reacting a compound [II] with a compound [III] or a salt thereof.

Suitable salt of the compound [III] may be the same as those exemplified for the compound [I].

The reaction is preferably carried out in the presence of a base such as an alkali metal carbonate [e.g. sodium carbonate, potassium carbonate, etc.], an alkaline earth metal carbonate [e.g. magnesium carbonate, calcium carbonate, etc.], an alkali metal bicarbonate [e.g. sodium bicarbonate, potassium bicarbonate, etc.], tri(lower)alkylamine [e.g. trimethylamine, triethylamine, etc.], picoline, and the like.

The reaction is usually carried out in a conventional solvent, such as an alcohol [e.g. methanol, ethanol, propanol, isopropanol, etc.], diethyl ether, tetrahydrofuran, dioxane, or any other organic solvent which does not adversely influence the reaction.

The reaction temperature is not critical, and the reaction can be carried out under cooling to heating.

Process 2

The object compound [Ib] or a salt thereof can be prepared by subjecting a compound [Ia] or a salt thereof to elimination reaction of the amino protective group.

Suitable salts of the compounds [Ia] and [Ib] may be the same as those exemplified for the compound [I].

This reaction can be carried out in a similar manner to that of Example 3 mentioned below.

Process 3

The object compound [Ic] or a salt thereof can be prepared by reacting a compound [IV] or a salt thereof with a compound [V] or a salt thereof.

Suitable salts of the compounds [Ic], [IV] and [V] may be the same as those exemplified for the compound [I].

This reaction can be carried out in a similar manner to that of Example 2 mentioned below.

Process 4

The object compound [Ic] or a salt thereof can be prepared by reacting a compound [IV] or a salt thereof with a compound [VI] or a salt thereof.

Suitable salts of the compounds [Ic], [IV] and [VI] may be the same as those exemplified for the compound [I].

This reaction can be carried out in a similar manner to that of Preparation 43 mentioned below.

Process 5

The object compound [If] or a salt thereof can be prepared by subjecting a compound [Id] or a salt thereof to deesterification reaction followed by reacting the resulting compound [Ie] or a salt thereof with a compound [VII] or a salt thereof.

Suitable salts of the compounds [If], [Id], [Ie] and [VII] may be the same as those exemplified for the compound [I].

These reactions can be carried out in a similar manner to that of Preparation 3 and Example 11 mentioned below.

Process 6

The object compound [Ig] or a slat thereof can be prepared by reacting a compound [VIII] or a salt thereof with a compound [IX] or a salt thereof.

Suitable salt of the compounds [Ig], [VIII] and [IX] may be the same as those exemplified for the compound [I].

This reaction can be carried out in a similar manner to that of Example 18 mentioned bellow.

The compounds obtained by the above processes can be isolated and purified by a conventional method such as pulverization, recrystallization, column chromatography, reprecipitation, and the like, and converted to the desired salt in conventional manners, if necessary.

It is to be noted that the compound [I] and the other compounds may include one or more stereoisomers due to asymmetric carbon atoms, and all of such isomers and mixture thereof are included within the scope of this invention.

It is further to be noted that isomerization or rearrangement of the object compound [I] may occur due to the effect of the light, acid base or the like, and the compound obtained as the result of said isomerization or rearrangement if also included within the scope of the present invention.

It is also to be noted that the solvating form of the compound [I] [e.g. hydrate, etc.] and any form of the crystal of the compound [I] are included within the scope of the present invention.

The object compound [I] or a salt thereof are useful for the treatment and/or prevention of gastro-intestinal disorders in human beings or animals, and more particularly for the treatment and/or prevention of spasm or hyperanakinesia in case of irritable bowel syndrome, gastritis, gastric ulcer, duodenal ulcer, enteritis, cholecystopathy, cholantitis, urinary calculus, and the like; for the treatment and/or prevention of ulcer such as gastric ulcer, duodenal ulcer, peptic ulcer, and the like; for the treatment and/or prevention of overactive bladder such as nervous pollakiuria, neurogenic bladder dysfunction, nocturia, unstable bladder, cystospasm, chronic cystitis, chronic prostatitis, prostatic hypertrophy, and the like; for the treatment and/or prevention of micturition disorders such as stress incontinence, urge incontinence, mixed incontinence, functional incontinence, overflow incontinence, and the like; for the treatment and/or prevention of pancreatitis, obesity, diabetes, glycosuria, hyperlipidemia, hypertension, atherosclerosis, glaucoma, melancholia, depression, and the like; for the treatment and/or prevention of diseases as the result of insulin resistance [e.g. hypertension, hyperinsulinemia, etc.]; for the treatment and/or prevention of neurogenetic inflammation; and for reducing a wasting condition, and the like.

Additionally, $\beta_3$ adrenergic receptor agonists are known to lower triglyceride and cholesterol levels and to raise high density lipoprotein levels in mammals (U.S. Pat. No. 5,451,677). Accordingly, the object compound [I] is useful in the treatment and/or prevention of conditions such as hyper-triglyceridaemia, hypercholesterolaemia and in lowering high density lipoprotein levels as well as in the treatment of atherosclerotic and cardiovascular diseases and relates conditions.

Moreover, the object compound [I] is useful for inhibiting uterine contractions, preventing premature labor, and treating and preventing dysmenorrhea.

Additionally, the object compound [I] may be expected, when used together with an anticholinergic agent for overactive bladder such as propiverine hydrochloride, oxybutinin hydrochloride, flavoxate hydrochloride, tolterodine tartrate, and the like, to exert an enhanced anti-overactive-bladder effect.

For therapeutic purpose, the compound (I) and a pharmaceutically acceptable salt thereof of the present invention can be used in a form of pharmaceutical preparation containing one of said compounds, as an active ingredients, in admixture with a pharmaceutically acceptable carrier such as an organic or inorganic solid or liquid excipient suitable for oral, parenteral, external including topical, internal, intravenous, intramuscular, inhalant, nasal, intraarticular, intraspinal, transtracheal or transocular administration. The pharmaceutical preparations may be solid, semi-solid or solutions such as capsules, tablets, pellets, dragees, powders, granules, suppositories, ointments, creams, lotions, inhalants, injections, cataplasms, gels, tapes, eye drops, solution, syrups, aerosols, suspension, emulsion, and the like. If desired, there may be included in these preparations, auxiliary substances, stabilizing agents, wetting or emulsifying agents, buffers and other commonly used additives.

While the dosage of the compound (I) will vary depending upon the age and condition of a patient, an average single dose of about 0.1 mg, 1 mg, 10 mg, 50 mg, 100 mg, 250 mg, 500 mg and 1000 mg of the compound (I) may be effective for treating diseases such as ulcer, overactive bladder, micturition disorders, and the like. In general, amounts between 0.1 mg/body and about 1,000 mg/body may be administered per day.

In order to show the usefulness of the compound [I] for the prophylactic and therapeutic treatment of above-mentioned disease in human being or animals, a representative compound of the compound [I] was tested on the following pharmaceutical test.

Test

Effect on the increase in intravesical pressure induced by carbachol in anesthetized dog Test Compound (1) 3-(Cyclohexyloxy)-N-[(2-hydroxyethyl)sulfonyl]-4'-[2-[[(2R)-2-hydroxy-2-phenylethyl]amino]ethyl]-4-biphenylcarboxamide hydrochloride (the object compound of Example 1-(8) mentioned below)

Test Method

Female Beagle dogs weighing 8.0-15.0 kg were fasted for 24 hours and maintained under halothane anesthesia. A 12F Foley catheter was lubricated with water soluble jelly, inserted into the urethral orifice, and advanced approximately 10 cm until the balloon tip was placed well inside the bladder. The balloon was then inflated with 5 ml of room air and catheter slowly withdrawn just part the first resistance that was felt at the bladder neck. Urine was completely drained out through the catheter, and 30 ml of biological saline was infused. The catheter was connected to pressure transducer, and intravesical pressure (IVP) was continuously recorded. The test compound was administered intradermally at 30 minutes before the administration of carbachol (1.8 μg/kg). Percent inhibition of IVP increase by test compound was calculated by dividing IVPa (IVP increase induced by carbachol after test compound administration) by IVPb (IVP increase induced by carbachol just before test compound administration).

| Test Result | |
|---|---|
| Treatment | Percent inhibition of IVP increase |
| Test Compound (1) (0.032 mg/kg) | 78 |

Preferred embodiments of the object compound [I] are as follows:

—X— is

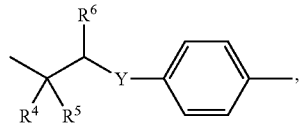

in which —Y— is bond, —O—, —NH— or —CH$_2$—, and
$R^4$, $R^5$ and $R^6$ are each independently hydrogen, lower alkyl (more preferably $C_1$-$C_4$ alkyl) or hydroxy(lower)alkyl (more preferably hydroxy($C_1$-$C_4$)alkyl).

More preferred embodiments of the object compound [I] are as follows:

$R^1$ is hydrogen, halogen (more preferably fluoro or chloro), nitro or amino, $R^2$ is hydrogen or lower alkyl (more preferably $C_1$-$C_4$ alkyl, most preferably methyl), $R^3$ is hydrogen, $R^7$ is hydrogen, lower alkyl (more preferably $C_1$-$C_4$ alkyl, most preferably isopropyl or isobutyl), cyclo(lower)alkyl (more preferably cyclo($C_3$-$C_6$)alkyl, most preferably cyclopentyl), —Z—$R^9$ or

in which —Z— is —O—, —S—, —SO— or —SO$_2$—, and each $R^9$ is independently hydrogen, lower alkyl (more preferably $C_1$-$C_4$ alkyl, most preferably propyl, isopropyl or isobutyl) or cyclo(lower)alkyl (more preferably cyclo($C_3$-$C_6$)alkyl, most preferably cyclopentyl, cyclohexyl or cycloheptyl), and $R^8$ is -D-E-$R^{10}$, in which -D- is —CONHSO$_2$— or —SO$_2$NHCO—, E is bond or lower alkylene (more preferably $C_1$-$C_4$ alkylene, most preferably methylene, ethylene, trimethylene, 3,3-dimethyltrimethylene or tetramethylene), and $R^{10}$ is halogen, cyano, carboxy, lower alkoxycarbonyl (more preferably $C_1$-$C_4$ alkoxycarbonyl, most preferably methoxycarbonyl), carbamoyl, pyridyl, —O—$R^{11}$ or

in which each $R^{11}$ is independently hydrogen, lower alkyl (more preferably $C_1$-$C_4$ alkyl, most preferably methyl or ethyl), lower alkanoyl (more preferably $C_1$-$C_4$ alkanoyl, most preferably acetyl) or lower alkoxycarbonyl (more preferably $C_1$-$C_4$ alkoxycarbonyl, most preferably tert-butoxycarbonyl).

Furthermore preferred embodiments of the compound [I] are as follows:

—X— is

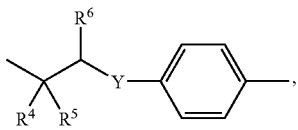

in which —Y— is bond, —O—, —NH— or —CH$_2$—, and $R^4$, $R^5$ and $R^6$ are each hydrogen, $R^7$ is lower alkyl (more preferably $C_1$-$C_4$ alkyl, most preferably isopropyl or isobutyl), cyclo(lower)alkyl (more preferably cyclo($C_3$-$C_6$)alkyl, most preferably cyclopentyl), —Z—$R^9$ or

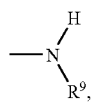

in which —Z— is —O— or —S—, and each $R^9$ is independently lower alkyl or cyclo(lower)alkyl (more preferably $C_1$-$C_4$ alkyl, most preferably propyl, isopropyl or isobutyl) or cyclo(lower)alkyl (more preferably cyclo($C_3$-$C_6$)alkyl, most preferably cyclopentyl, cyclohexyl or cycloheptyl), and $R^8$ is -D-E-$R^{10}$, in which -D- is —CONHSO$_2$— or —SO$_2$NHCO—, E is bond or lower alkylene (more preferably, $C_1$-$C_4$ alkylene, most preferably methylene, ethylene, trimethylene, 3,3-dimethyltrimethylene or tetramethylene), and $R^{10}$ is cyano, carboxy, carbamoyl, pyridyl, —O—$R^{11}$ or

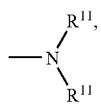

in which each $R^{11}$ is independently hydrogen lower alkyl (more preferably $C_1$-$C_4$ alkyl, most preferably methyl or ethyl).

The following Preparations and Examples are given for the purpose of illustrating this invention. The group of "carbamoyl" aforementioned may be hereinafter referred to as a group of "aminocarbonyl".

PREPARATION 1

To a solution of tert-butyl [(2R)-2-hydroxy-2-phenylethyl] [2-[3'-(isopropoxy)-4'-[[(methylsulfonyl)amino]carbonyl]-4-biphenylyl]ethyl]carbamate (65 mg) in 1,4-dioxane (2 ml) was added hydrochloric acid 1,4-dioxane solution (4N, 4 ml) at room temperature and the mixture was stirred at the same temperature for 2.5 hours. The mixture was evaporated under reduced pressure to give 4'-[2-[[(2R)-2-hydroxy-2-phenylethyl]amino]ethyl]-3-isopropoxy-N-(methylsulfonyl)-4-biphenylcarboxamide hydrochloride (38 mg).

NMR (200 MHz, DMSO-d$_6$, δ): 1.37 (6H, d, J=5.7 Hz), 3.06-3.25 (6H, m), 3.38 (3H, s), 4.97-5.00 (2H, m), 6.23 (1H, br s), 7.28-7.48 (9H, m), 7.72-7.79 (3H, m)

(+)ESI-MS (m/z): 497 (M+H)$^+$

EXAMPLE 1

The following compounds were obtained according to a similar manner to that of Preparation 1.

(1) 4'-[2-[[(2R)-2-Hydroxy-2-phenylethyl]amino]ethyl]-N-[(3-hydroxypropyl)sulfonyl]-3-isopropoxy-4-biphenylcarboxamide hydrochloride NMR (200 MHz, DMSO-d$_6$, δ): 1.36 (6H, d, J=6.0 Hz), 1.81-1.95 (2H, m), 2.99-2.73 (6H, m), 3.47-3.58 (4H, m), 4.75 (1H, t, J=5.0 Hz), 4.91-5.05 (2H, m), 6.24 (1H, d, J=4.0 Hz), 7.31-7.43 (9H, m), 7.68-7.76 (3H, m)

(+)ESI-MS (m/z): 541 (M+H)$^+$ (2) 4'-[2-[[(2R)-2-Hydroxy-2-phenylethyl]amino]ethyl]-N-[(3-hydroxypropyl)sulfonyl]-3-(isopropylthio)-4-biphenylcarboxamide hydrochloride NMR (200 MHz, DMSO-d$_6$, δ): 1.25 (6H, d, J=6.5 Hz), 1.85-1.99 (2H, m), 3.02-3.27 (6H, m), 3.49-3.58 (4H, m), 3.62-3.72 (1H, m), 4.76 (1H, br s), 4.95-5.04 (1H, m), 6.23 (1H, d, J=4 Hz), 7.31-7.42 (7H, m), 7.55-7.64 (2H, m), 7.70-7.74 (3H, m), 8.92 (1H, br s), 9.26 (1H, br s), 12.14 (1H, s)

(−)ESI-MS (m/z): 555 (M−H)$^-$ (3) 3-(Cyclohexyloxy)-4'-[2-[[(2R)-2-hydroxy-2-phenylethyl]amino]ethyl]-N-[(3-hydroxypropyl)sulfonyl]-4-biphenylcarboxamide hydrochloride NMR (200 MHz, DMSO-d$_6$, δ): 1.34-2.01 (12H, m), 2.99-3.27 (6H, m), 3.46-3.59 (4H, m), 4.71-4.84 (2H, m), 4.94-5.04 (1H, m), 6.23 (1H, d, J=3.5 Hz), 7.32-7.43 (9H, m), 7.71-7.75 (3H, m)

(−)ESI-MS (m/z): 579 (M−H)$^-$ (4) 3-(Cyclohexyloxy)-N-[(3-hydroxypropyl)sulfonyl]-4'-[2-[[(2R)-2-hydroxy-2-(3-pyridyl)ethyl]amino]ethyl]-4-biphenylcarboxamide dihydrochloride NMR (200 MHz, DMSO-d$_6$, δ): 1.35-2.02 (12H, m), 3.05-3.39 (6H, m), 3.48-3.60 (4H, m), 4.75-4.87 (1H, m), 5.27-5.35 (1H, m), 7.33-7.44 (4H, m), 7.71-7.75 (3H, m), 7.98 (1H, dd, J=5.5, 8.5 Hz), 8.49 (1H, d, J=8.5 Hz), 8.83-8.91 (2H, m), 9.30 (1H, br s), 9.41 (1H, br s), 11.18 (1H, s)

(−)ESI-MS (m/z): 580 (M−H)$^-$ (5) 3-(Cyclohexyloxy)-4'-[2-[[(2R)-2-hydroxy-2-(3-pyridyl)ethyl]amino]ethyl]-N-[(2-methoxyethyl)sulfonyl]-4-biphenylcarboxamide dihydrochloride NMR (200 MHz, DMSO-d$_6$, δ): 1.31-2.04 (10H, m), 3.04-3.50 (6H, m), 3.23 (3H, s), 3.72-3.84 (4H, m), 4.78-4.89 (1H, m), 5.27-5.37 (1H, m), 7.34-7.45 (4H, m), 7.68-7.79 (3H, m), 8.00 (1H, dd, J=5.5, 8.4 Hz), 8.51 (1H, d, J=8.4 Hz), 8.83-8.92 (2H, m), 9.33 (1H, br s), 9.45 (1H, br s), 11.19 (1H, s)

(−)ESI-MS (m/z): 580 (M−H)$^-$ (6) 3-(Cyclohexyloxy)-N-[(2-hydroxyethyl)sulfonyl]-4'-[2-[[(2R)-2-hydroxy-2-(3-pyridyl)ethyl]amino]ethyl]-4-biphenylcarboxamide dihydrochloride NMR (200 MHz, DMSO-d$_6$, δ): 1.30-2.01 (10H, m), 3.02-3.49 (6H, m), 3.67 (2H, t, J=6.0 Hz), 3.84 (2H, t, J=5.8 Hz), 4.75-4.89 (1H, m), 5.26-5.37 (1H, m), 7.32-7.45 (4H, m), 7.69-7.82 (3H, m), 7.97 (1H, d, J=5.4 Hz), 8.5 (1H, d, J=8.0 Hz), 8.82-8.93 (2H, m), 9.31 (1H, br s), 9.43 (1H, br s), 11.1 (1H, br s)

(−)ESI-MS (m/z): 566 (M−H)$^-$ (7) N-[(3-Hydroxypropyl)sulfonyl]-4'-[2-[[(2R)-2-hydroxy-2-(3-pyridyl)ethyl]amino]ethyl]-3-isopropoxy-4-biphenylcarboxamide dihydrochloride NMR (200 MHz, DMSO-d$_6$, δ): 1.37 (6H, d, J=6 Hz), 1.81-1.96 (2H, m), 3.03-3.6 (8H, m), 4.91-5.03 (1H, m), 5.25-5.34 (1H, m), 7.32-7.44 (4H, m), 7.68-7.77 (3H, m), 7.96 (1H, dd, J=5.6, 8 Hz), 8.46 (1H, d, J=8 Hz), 8.8-8.89 (2H, m), 9.26 (1H, br s), 9.37 (1H, br s), 11.22 (1H, s)
(−)ESI-MS (m/z): 540 (M−H)⁻
(8) 3-(Cyclohexyloxy)-N-[(2-hydroxyethyl)sulfonyl]-4'-[2-[[(2R)-2-hydroxy-2-phenylethyl]amino]ethyl]-4-biphenylcarboxamide hydrochloride
NMR (200 MHz, DMSO-d₆, δ): 1.31-2.03 (10H, m), 3.00-3.29 (6H, m), 3.66 (2H, t, J=6 Hz), 3.79-3.87 (2H, m), 4.76-4.87 (1H, m), 4.95-5.11 (2H, m), 6.23 (1H, d, J=3.6 Hz), 7.31-7.44 (9H, m), 7.69-7.81 (3H, m)
(−)ESI-MS (m/z): 565 (M−H)⁻

PREPARATION 2

The following compounds were obtained according to a similar manner to that of Example 2.
(1) Methyl 4'-[2-[(tert-butoxycarbonyl)[(2R)-2-hydroxy-2-(3-pyridyl)ethyl]amino]ethyl]-3-(cycloheptyloxy)-4-biphenylcarboxylate
(+)ESI-MS (m/z): 589 (M+H)⁺
(2) Methyl 4'-[3-[(tert-butoxycarbonyl)[(2R)-2-hydroxy-2-(3-pyridyl)ethyl]amino]propyl]-3-isopropoxy-4-biphenylcarboxylate
(+)ESI-MS (m/z): 549 (M+H)⁺, 571 (M+Na)⁺

PREPARATION 3

To a solution of methyl 4'-[2-[(tert-butoxycarbonyl)-[(2R)-2-hydroxy-2-(3-pyridyl)ethyl]amino]ethyl]-3-(cycloheptyloxy)-4-biphenylcarboxylate (813 mg) in methanol (8.1 ml) and tetrahydrofuran (2.4 ml) was added 1N sodium hydroxide (4.14 ml) and the mixture was stirred at room temperature for 24 hours. The mixture was quenched by the addition of 1N hydrochloric acid (4.14 ml) and the solvent was removed by evaporation. The residue was chromatographed on silica gel (eluent: hexane/ethyl acetate) to give 4'-[2-[(tert-butoxycarbonyl)[(2R)-2-hydroxy-2-(3-pyridyl)ethyl]amino]ethyl]-3-(cycloheptyloxy)-4-biphenylcarboxylic acid (575 mg) as a white solid.
(−)ESI-MS (m/z): 573 (M−H)⁻

PREPARATION 4

To a solution of 4-bromo-2-cyclopentylbenzoic acid (4.05 g) in N,N-dimethylformamide (40 ml) was added N,N'-carbonyldiimidazole (2.68 g) at room temperature and the mixture was stirred for 4 hours. To the mixture were added 3-(aminosulfonyl)propyl acetate (3.0 g) and 1,8-diazabicyclo[5.4.0]undec-7-ene (2.7 ml) and the whole was stirred at 120° C. for 20 hours. After cooling to room temperature, the mixture was quenched by the addition of 1N hydrochloric acid (100 ml) and extracted with ethyl acetate (100 ml, 50 ml). The combined extracts were washed with water (100 ml×2) and brine (100 ml), and dried over magnesium sulfate. Filtration followed by evaporation gave a yellow solid (6.77 g) which was chromatographed on silica gel (eluent: hexane/ethyl acetate) to give 3-[[(4-bromo-2-cyclopentylbenzoyl)amino]sulfonyl]propyl acetate (5.20 g) as a white solid.
(−)ESI-MS (m/z): 430, 432 (M−H)⁻

PREPARATION 5

A mixture of 3-[[(4-bromo-2-cyclopentylbenzoyl)amino]sulfonyl]propyl acetate (5.17 g), bis(pinacolato)diboron (3.34 g), [1,1'-bis(diphenylphosphino)ferrocene]-dichloropalladium(II), complex with dichloromethane (1:1, 977 mg), 1,1'-bis(diphenylphosphino)ferrocene (331 mg), potassium acetate (4.70 g) and 1,4-dioxane (52 ml) was stirred at 95° C. for 2 hours. After cooling to room temperature, the mixture was quenched by the addition of 0.5N hydrochloric acid (100 ml) and extracted with ethyl acetate (100 ml). The organic layer was separated and washed with water (100 ml) and 10% sodium chloride solution (100 ml). To the organic layer were added water (100 ml), ammonium acetate (4.15 g) and sodium periodate (8.95 g). The mixture was stirred at room temperature overnight. The insoluble solid was filtered off and washed with ethyl acetate, and the organic layer was separated. The organic layer was washed with 0.5N hydrochloric acid (100 ml) and brine (100 ml), and dried over magnesium sulfate. Filtration followed by evaporation gave a brown solid (6.62 g) which was chromatographed on silica gel (eluent: ethyl acetate/methanol) to give [4-[[[[3-(acetyloxy)propyl]-sulfonyl]amino]carbonyl]-3-cyclopentylphenyl]boronic acid (3.34 g) as a brown solid.
(−)ESI-MS (m/z): 396 (M−H)⁻

PREPARATION 6

[4-[[[[3-(Acetyloxy)propyl]sulfonyl]amino]carbonyl]-3-cyclopentylphenyl]boronic acid (3.28 g) was dissolved in 2.5N hydrogen chloride in methanol (20 ml) and the mixture was stirred at room temperature for 17 hours. The solvent was removed by evaporation to give [3-cyclopentyl-4-[[[(3-hydroxypropyl)sulfonyl]amino]carbonyl]phenyl]boronic acid (3.16 g) as a brown solid.
(−)ESI-MS (m/z): 354 (M−H)⁻

PREPARATION 7

A mixture of 2-bromoethanol (7.0 g) and potassium thiocyanate (5.4 g) in methanol (40 ml) was refluxed for 7 hours. After precipitate was filtered off, the filtrate was evaporated under reduced pressure. The residue was suspended in chloroform/methanol (5/1). The precipitate was filtered off. The filtrate was evaporated under reduced pressure to give the thiocyanate (4.4 g). To a mixture of the thiocyanate in pyridine (4.8 ml)/dichloromethane (20 ml) was added acetic anhydride (5.3 ml) in dichloromethane (5 ml) at 5° C. The mixture was stirred at room temperature for 6 hours. The precipitate was filtered off. The filtrate was washed with water, dried over sodium sulfate and evaporated under reduced pressure to give 2-thiocyanatoethyl acetate (5.6 g).
NMR (200 MHz, DMSO-d₆, δ): 2.06 (3H, s), 3.36 (2H, t, J=5.8 Hz), 4.32 (2H, t, J=5.8 Hz)

PREPARATION 8

A solution of 2-thiocyanatoethyl acetate (5.6 g) in water (20 ml) was bubbled with chlorine gas for 20 minutes under ice-cooling with stirring followed by extraction with dichloromethane. After the extract was dried over sodium sulfate, the solvent was evaporated under reduced pressure to give sulfonyl chloride (6.0 g, colorless oil). The sulfonyl chloride was dissolved in dichloromethane (60 ml) and bubbled with ammonia gas for 1 hour under ice-cooling. The precipitate was filtered off, and the filtrate was washed with water, dried over sodium sulfate and evaporated under reduced pressure. The residue was purified by column chromatography on silica gel (chloroform/methanol=92/8 to 90/10) to give 2-(aminosulfonyl)ethyl acetate (385 mg).
NMR (200 MHz, CDCl₃, δ): 2.11 (3H, s), 3.47 (2H, t, J=6.0 Hz), 4.54 (2H, t, J=6.0 Hz), 5.10 (2H, br s)
(−)ESI-MS (m/z): 166 (M−H)⁻

PREPARATION 9

A mixture of [(2-bromoethoxy)methyl]benzene (6.0 g) and sodium sulfate (3.9 g) in water (12 ml) and ethanol (36 ml) was refluxed overnight. The mixture was acidified with conc. hydrochloric acid under ice-cooling. The mixture was evaporated under reduced pressure. The residue was suspended in dichloromethane/methanol (4/1) and filtered off through Celite pad. The filtrate was evaporated to give 2-(benzyloxy)ethanesulfonic acid (4.5 g).

(−)ESI-MS (m/z): 215 (M−H)−

PREPARATION 10

To a 2-(benzyloxy)ethanesulfonic acid (4.0 g) was added thionyl chloride (13.5 ml) dropwise at ambient temperature for 15 minutes and the mixture was stirred at the same temperature for 10 minutes. To the mixture was added dropwise N,N-dimethylformamide (0.072 ml) at ambient temperature. The mixture was stirred at the same temperature for 20 minutes and refluxed for 1 hour. After cooling down to room temperature, the mixture was evaporated under reduced pressure to give 2-(benzyloxy)ethanesulfonyl chloride (4.1 g).

NMR (200 MHz, CDCl$_3$, δ): 3.92-4.08 (4H, m), 4.60 (2H, s), 7.32-7.39 (5H, m)

PREPARATION 11

To a 28% ammonium hydroxide (10 ml) was added dropwise 2-(benzyloxy)ethanesulfonyl chloride (4.1 g) in dichloromethane (10 ml) over 10 minutes under ice-cooling. The mixture was stirred at ambient temperature overnight. The organic layer was separated and the aqueous layer was extracted with dichloromethane/methanol (5/1). The combined organic layer was dried over sodium sulfate and evaporated under reduced pressure. The residue was purified by column chromatography on silica gel (hexane/ethyl acetate=50/50) to give 2-(benzyloxy)ethanesulfonamide (1.6 g).

NMR (200 MHz, CDCl$_3$, δ): 3.39 (2H, t, J=5.5 Hz), 3.96 (2H, t, J=5.5 Hz), 4.57 (2H, s), 4.84 (2H, br s), 7.30-7.42 (5H, m)

(+)ESI-MS (m/z): 238 (M+Na)+

PREPARATION 12

The following compounds were obtained according to a similar manner to that of Preparation 4.

(1) 3-[[[4-Bromo-2-(cyclohexyloxy)benzoyl]amino]-sulfonyl]propyl acetate (−)ESI-MS (m/z): 460 (M−H)−

(2) N-[[2-(Benzyloxy)ethyl]sulfonyl]-4-bromo-2-(cyclohexyloxy)benzamide (−)ESI-MS (m/z): 494 (M−H)−

(3) 3-[[(4-Bromo-2-isopropoxybenzoyl)amino]sulfo-nyl]-propyl acetate (+)ESI-MS (m/z): 444 (M+Na)+

PREPARATION 13

The following compounds were obtained according to a similar manner to that of Preparation 5.

(1) [4-[[[[3-(Acetyloxy)propyl]sulfonyl]amino]carbonyl]-3-(cyclohexyloxy)phenyl]boronic acid
(+)ESI-MS (m/z): 450 (M+Na)+
(2) [4-[[[[2-(Benzyloxy)ethyl]sulfonyl]amino]carbonyl]-3-(cyclohexyloxy)phenyl]boronic acid
(+)ESI-MS (m/z): 484 (M+Na)+
(3) [4-[[[[3-(Acetyloxy)propyl]sulfonyl]amino]carbonyl]-3-isopropoxyphenyl]boronic acid
(+)ESI-MS (m/z): 410 (M+Na)+
(4) [4-[[[[3-(Acetyloxy)propyl]sulfonyl]amino]carbonyl]-3-isobutylphenyl]boronic acid
(−)ESI-MS (m/z): 384 (M−H)−

PREPARATION 14

The following compounds were obtained according to a similar manner to that of Preparation 6.
(1) [3-(Cyclohexyloxy)-4-[[[(3-hydroxypropyl)sulfonyl]-amino]carbonyl]phenyl]boronic acid
(+)ESI-MS (m/z): 450 (M+Na)+
(2) [4-[[[(3-Hydroxypropyl)sulfonyl]amino]carbonyl]-3-isopropoxyphenyl]boronic acid
(+)ESI-MS (m/z): 368 (M+Na)+
(3) [4-[[[(3-Hydroxypropyl)sulfonyl]amino]carbonyl]-3-isobutylphenyl]boronic acid
(−)ESI-MS (m/z): 342 (M−H)−

PREPARATION 15

The following compounds were obtained according to a similar manner to that of Example 15.
(1) Methyl 4'-[2-[(tert-butoxycarbonyl)[(1S,2R)-2-hydroxy-1-methyl-2-phenylethyl]amino]ethyl]-3-(cyclohexyloxy)-4-biphenylcarboxylate
(+)ESI-MS (m/z): 610 (M+Na)+
(2) Methyl 4'-[2-[(tert-butoxycarbonyl)[(2R)-2-phenyl-2-(tetrahydro-2H-pyran-2-yloxy)ethyl]amino]ethyl]-3-cyclopentyl-4-biphenylcarboxylate
(+)ESI-MS (m/z): 650 (M+Na)+
(3) tert-Butyl [2-[4'-(aminosulfonyl)-3'-(cyclohexyloxy)-4-biphenylyl]ethyl][(2R)-2-phenyl-2-(tetrahydro-2H-pyran-2-yloxy)ethyl]carbamate
(+)ESI-MS (m/z): 701 (M+Na)+

PREPARATION 16

The following compounds were obtained according to a similar manner to that of Preparation 3.
(1) 4'-[2-[(tert-Butoxycarbonyl)[(1S,2R)-2-hydroxy-1-methyl-2-phenylethyl]amino]ethyl]-3-(cyclohexyloxy)-4-biphenylcarboxylic acid
(+)ESI-MS (m/z): 610 (M+Na)+
(2) 4'-[2-[(tert-Butoxycarbonyl)[(2R)-2-phenyl-2-(tetrahydro-2H-pyran-2-yloxy)ethyl]amino]ethyl]-3-cyclopentyl-4-biphenylcarboxylic acid
(−)ESI-MS (m/z): 612 (M−H)−
(3) 4'-[2-[(tert-Butoxycarbonyl)[(2R)-2-(3-chlorophenyl)-2-hydroxyethyl]amino]ethyl]-3-(isopropylthio)-4-biphenylcarboxylic acid
(−)ESI-MS (m/z): 568, 570 (M−H)−
(4) 4'-[3-[(tert-Butoxycarbonyl)[(2R)-2-hydroxy-2-(3-pyridyl)ethyl]amino]propyl]-3-isopropoxy-4-biphenylcarboxylic acid
(−)ESI-MS (m/z): 533 (M−H)−

PREPARATION 17

The following compound was obtained according to a similar manner to that of Example 26.

Methyl 4'-[2-[(tert-butoxycarbonyl)[(2R)-2-(3-chlorophenyl)-2-hydroxyethyl]amino]ethyl]-3-(isopropylthio)-4-biphenylcarboxylate (+)ESI-MS (m/z): 606 (M+Na)$^+$

PREPARATION 18

The following compound was obtained according to a similar manner to that of Example 11.

3-[[(4-Bromo-2-isobutylbenzoyl)amino]sulfonyl]propyl acetate (−)ESI-MS (m/z): 418, 420 (M−H)$^−$

PREPARATION 19

The following compounds were obtained according to a similar manner to that of Preparation 7.

(1) Methyl 3-thiocyanatopropanoate
(+)ESI-MS (m/z): 168 (M+Na)$^+$ (2) 4-Hydroxybutyl thiocyanate
NMR (200 MHz, CDCl$_3$, δ): 1.69-1.79 (2H, m), 1.9-2.03 (2H, m), 2.99-3.06 (2H, m), 3.68-3.74 (2H, m), 4.00 (1H, s)

(3) 4-Thiocyanatobutyl acetate
NMR (200 MHz, CDCl$_3$, δ): 1.77-2.07 (4H, m), 2.10 (3H, s), 2.99 (2H, t, J=7 Hz), 4.12 (2H, t, J=6.1 Hz)

PREPARATION 20

Methyl 3-thiocyanatopropanate (2.00 g) was dissolved in water (20 ml) and cooled at 0° C. Chlorine gas was bubbled into the solution for 1 hour at the same temperature. The reaction mixture was poured into the mixture of cold water and diethyl ether and the aqueous layer was separated. The organic layer was washed with brine and dried over magnesium sulfate. Evaporation of the solvent afforded methyl 3-(chlorosulfonyl)propanoate (2.31 g).

NMR (200 MHz, CDCl$_3$, δ): 3.06 (2H, t, J=8 Hz), 3.79 (3H, s), 4.01 (2H, d, J=8 Hz)

PREPARATION 21

Methyl 3-(chlorosulfonyl)propanoate (2.31 g) was dissolved in dichloromethane (1.85 ml) and tetrahydrofuran (4.60 ml) and cooled at −10° C. Ammonia gas was bubbled into the solution for 1.5 hours at the same temperature. After filtration through Celite, the reaction mixture was evaporated. The residue was purified by column chromatography on silica gel eluting with chloroform and methanol to give methyl 3-(aminosulfonyl)propanoate (1.80 g).

NMR (400 MHz, CDCl$_3$, δ): 2.90 (2H, t, J=7.2 Hz), 3.48 (2H, t, J=7.2 Hz), 3.74 (3H, s), 4.94 (2H, br s)

(+)ESI-MS (m/z): 190 (M+Na)$^+$

PREPARATION 22

The following compound was obtained according to a similar manner to that of Preparation 20.

4-(Chlorosulfonyl)butyl acetate
NMR (200 MHz, CDCl$_3$, δ): 1.79-1.93 (2H, m), 2.07 (3H, s), 2.07-2.23 (2H, m), 3.72 (2H, t, J=7.7 Hz), 4.14 (2H, t, J=6.1 Hz)

PREPARATION 23

The following compound was obtained according to a similar manner to that of Preparation 21.

4-(Aminosulfonyl)butyl acetate
(−)ESI-MS (m/z): 194 (M−H)$^−$

PREPARATION 24

To an ammonium hydroxide (28%, 80 ml) was added a solution of 4-bromo-2-fluorobenzenesulfonyl chloride (10 g) in dichloromethane (80 ml) dropwise for 1 hour at approximately 0° C. The reaction mixture was stirred vigorously for an additional 2 hours at the same temperature. The phases were separated. The aqueous phase was washed with dichloromethane. The combined organic extracts were washed with brine, dried over sodium sulfate and evaporated to give 4-bromo-2-fluorobenzenesulfonamide (8.0 g).

(+)ESI-MS (m/z): 276 (M+Na)$^+$

PREPARATION 25

To a suspension of sodium hydride (60%, 0.65 g) in N,N-dimethylformamide (22 ml) was added a solution of cyclohexanol (2.7 ml) in N,N-dimethylformamide (6 ml) for 30 minutes at ambient temperature. The suspension was stirred for 30 minutes at room temperature. A solution of 4-bromo-2-fluorobenzenesulfonamide (3 g) in N,N-dimethylformamide (13 ml) was added dropwise over 30 minutes at ambient temperature. The suspension was stirred at room temperature for 1 hour and at 60° C. for 2 hours. The suspension was poured into a mixture of ice (35 ml) and aqueous hydrochloric acid solution (1N, 35 ml), and the mixture was stirred at room temperature for 1 hour. The mixture was filtered to collect precipitate and the precipitate was washed with water and hexane. The precipitate was dried under reduced pressure to give 4-bromo-2-(cyclohexloxy)benzenesulfonamide (3.6 g).

(+)ESI-MS (m/z): 356 (M+Na)$^+$

PREPARATION 26

To a solution of 4-bromo-2-(cyclohexyloxy)benzenesulfonamide (3.6 g) in 1,4-dioxane (35 ml) were added bis(pinacolate)diboron (3.0 g), dichlorobis(triphenylphosphine)palladium(II) (528 mg) and potassium acetate (3.16 g), and the mixture was stirred at 95° C. for 2 hours under nitrogen atmosphere. After cooling down to room temperature, the mixture was poured into brine and extracted with ethyl acetate. The organic layer was separated, washed with brine, dried over sodium sulfate and evaporated under reduced pressure to give residue (6.4 g). To a mixture of the above residue in ethyl acetate (50 ml) and water (50 ml) were added ammonium acetate (1.8 g) and sodium periodate (5.0 g). The mixture was stirred at room temperature overnight. Precipitate was filtered off and the precipitate was washed with ethyl acetate/methanol (9/1). The filtrate was washed with aqueous hydrochloric acid solution (0.5N) and brine, dried over sodium sulfate and evaporated under reduced pressure. The residue was purified by column chromatography on silica gel (chloroform/methanol=95/5) to give [4-(aminosulfonyl)-3-(cyclohexyloxy)phenyl]boronic acid (2.5 g).

(+)ESI-MS (m/z): 322 (M+Na)$^+$

EXAMPLE 2

A mixture of tert-butyl [2-(4-bromophenyl)ethyl]-[(2R)-2-(3-chlorophenyl)-2-hydroxyethyl]carbamate (250 mg), [4-[[[(3-hydroxypropyl)sulfonyl]amino]carbonyl]-3-isopropoxyphenyl]boronic acid (228 mg), [1,1'-bis(diphenylphosphino)ferrocene]dichloropalladium(II), complex with dichloromethane (1:1, 67.3 mg), 1,1'-bis(diphenylphosphino)ferrocene (45.7 mg), N,N-dimethylformamide (5 ml) and 2N sodium carbonate solution (1.32 ml) was stirred at 80° C. for 2 hours. After cooling to room temperature, the mixture was quenched by the addition of 1N hydrochloric acid (2.64 ml) and partitioned between ethyl acetate (20 ml) and water (20 ml). The organic layer was separated, washed with water (20 ml×2) and brine (20 ml), and dried over magnesium sulfate. Filtration followed by evaporation gave a brown foam which was chromatographed on silica gel (eluent: hexane/ethyl acetate) to give tert-butyl [(2R)-2-(3-chlorophenyl)-2-hydroxyethyl][2-[4'-[[[(3-hydroxypropyl)sulfonyl]amino]-carbonyl]-3'-isopropxy-4-biphenylyl]ethyl]carbamate (236 mg) as a pale yellow solid.

(−)ESI-MS (m/z): 673 (M−H)−

EXAMPLE 3

To a solution of tert-butyl [(2R)-2-(3-chlorophenyl)-2-hydroxyethyl][2-[4'-[[[(3-hydroxypropyl)sulfonyl]amino]-carbonyl]-3'-isopropoxy-4-biphenylyl]ethyl]carbamate (231 mg) in 1,4-dioxane (2.3 ml) was added 4N hydrogen chloride in 1,4-dioxane (2.3 ml) and the mixture was stirred at room temperature for 5 hours. The precipitates were collected by filtration, washed with 1,4-dioxane, and dried under reduced pressure to give 4'-[2-[[(2R)-2-(3-chlorophenyl)-2-hydroxyethyl]amino]ethyl]-N-[(3-hydroxypropyl)sulfonyl]-3-isopropoxy-4-biphenylcarboxamide hydrochloride (158 mg) as a white solid.

NMR (400 MHz, DMSO-$d_6$, δ): 1.33 (6H, d, J=6.2 Hz), 1.85-1.92 (2H, m), 3.01-3.12 (3H, m), 3.19-3.27 (3H, m), 3.49-3.55 (4H, m), 4.74 (1H, t, J=5.1 Hz), 4.92-5.04 (2H, m), 6.37 (1H, d, J=4.0 Hz), 7.34-7.49 (8H, m), 7.70 (1H, d, J=8.1 Hz), 7.74 (2H, d, J=8.4 Hz), 9.06 (2H, br), 11.2 (1H, br)

(−)ESI-MS (m/z): 573 (M−H)−

EXAMPLE 4

The following compounds were obtained according to a similar manner to that of Example 2.

(1) tert-Butyl [(2R)-2-hydroxy-2-phenylethyl][2-[[4'-[[[(3-hydroxypropyl)sulfonyl]amino]carbonyl]-3'-isopropoxy-4-biphenylyl]oxy]ethyl]carbamate
(−)ESI-MS (m/z): 655 (M−H)−

(2) tert-Butyl [2-[[3'-(cyclohexyloxy)-4'-[[[(3-hydroxypropyl)sulfonyl]amino]carbonyl]-4-biphenylyl]oxy]-ethyl][(2R)-2-hydroxy-2-phenylethyl]carbamate
(−)ESI-MS (m/z): 695 (M−H)−

(3) tert-Butyl [2-[[3'-cyclopentyl-4'-[[[(3-hydroxypropyl)sulfonyl]amino]carbonyl]-4-biphenylyl]oxy]-ethyl][(2R)-2-hydroxy-2-phenylethyl]carbamate
(−)ESI-MS (m/z): 665 (M−H)−

(4) tert-Butyl [(2R)-2-(3-chlorophenyl)-2-hydroxyethyl]-[2-[[4'-[[[(3-hydroxypropyl)sulfonyl]amino]carbonyl]-3'-isopropoxy-4-biphenylyl]oxy]ethyl]carbamate
(−)ESI-MS (m/z): 689 (M−H)−

(5) tert-Butyl [(2R)-2-(3-chlorophenyl)-2-hydroxyethyl]-[2-[[3'-cyclopentyl-4'-[[[(3-hydroxypropyl)sulfonyl]-amino]carbonyl]-4-biphenylyl]oxy]ethyl]carbamate
(−)ESI-MS (m/z): 699 (M−H)−

(6) 3-[[[[4'-[2-[(tert-Butoxycarbonyl)[(2R)-2-(6-chloro-3-pyridyl)-2-hydroxyethyl]amino]ethoxy]-3-(cyclohexyloxy)-4-biphenylyl]carbonyl]amino]-sulfonyl]propyl acetate
(−)ESI-MS (m/z): 772 (M−H)−

(7) tert-Butyl [2-[3'-(cyclohexyloxy)-4'-[[[(3-hydroxypropyl)sulfonyl]amino]carbonyl]-4-biphenylyl]ethyl]-[(2R)-2-hydroxy-2-(4-nitrophenyl)ethyl]carbamate
(−)ESI-MS (m/z): 724 (M−H)−

(8) tert-Butyl [(2R)-2-hydroxy-2-(4-nitrophenyl)ethyl][2-[4'-[[[(3-hydroxypropyl)sulfonyl]amino]carbonyl]-3'-isobutyl-4-biphenylyl]ethyl]carbamate
(−)ESI-MS (m/z): 682 (M−H)−

(9) tert-Butyl [2-[3'-cyclopentyl-4'-[[[(3-hydroxypropyl)sulfonyl]amino]carbonyl]-4-biphenylyl]ethyl]-[(2R)-2-hydroxy-2-(4-nitrophenyl)ethyl]carbamate
(−)ESI-MS (m/z): 694 (M−H)−

(10) tert-Butyl [2-[4'-[[[[2-(benzyloxy)ethyl]sulfonyl]-amino]carbonyl]-3'-(cyclohexyloxy)-4-biphenylyl]-ethyl][(2R)-2-hydroxy-2-(4-nitrophenyl)ethyl]-carbamate

(11) tert-Butyl [2-[[3'-(cyclohexyloxy)-4'-[[[(3-hydroxypropyl)sulfonyl]amino]carbonyl]-4-biphenylyl]oxy]-ethyl][(2R)-2-hydroxy-2-(4-nitrophenyl)ethyl]-carbamate
(−)ESI-MS (m/z): 740 (M−H)−

(12) tert-Butyl [2-[[3'-cyclopentyl-4'-[[[(3-hydroxypropyl)sulfonyl]amino]carbonyl]-4-biphenylyl]oxy]-ethyl][(2R)-2-hydroxy-2-(4-nitrophenyl)ethyl]-carbamate
(−)ESI-MS (m/z): 710 (M−H)−

(13) tert-Butyl [2-[3'-(cyclohexyloxy)-4'-[[[(3-hydroxypropyl)sulfonyl]amino]carbonyl]-4-biphenylyl]ethyl]-[(2R)-2-hydroxy-2-(3-nitrophenyl)ethyl]carbamate
(−)ESI-MS (m/z): 724 (M−H)−

(14) 4'-[2-[[(1S,2R)-2-Hydroxy-1-methyl-2-phenylethyl]-amino]ethyl]-N-[(3-hydroxypropyl)sulfonyl]-3-isopropoxy-4-biphenylcarboxamide hydrochloride
NMR (200 MHz, DMSO-$d_6$, δ): 0.97 (3H, t, J=6.6 Hz), 1.26 (6H, d, J=6.0 Hz), 1.7-2.0 (2H, m), 3.0-3.2 (2H, m), 3.3-3.7 (6H, m), 4.74 (1H, m), 4.97 (1H, m), 5.20 (1H, m), 6.13 (1H, m), 7.1-7.5 (9H, m), 7.6-7.9 (3H, m)
ESI-MS (m/z): 555 (M+H)

(15) N-[(3-Hydroxypropyl)sulfonyl]-4'-[2-[[(2R)-2-hydroxy-2-(3-pyridyl)ethyl]amino]ethyl]-3-propoxy-4-biphenylcarboxamide dihydrochloride
NMR (200 MHz, DMSO-$d_6$, δ): 1.01 (3H, t, J=6.2 Hz), 1.7-2.0 (4H, m), 2.8-4.2 (12H, m), 5.24 (1H, m), 7.1-7.4 (4H, m), 7.5-8.0 (4H, m), 8.36 (1H, m), 8.7-9.0 (2H, m)
ESI-MS (m/z): 542 (M+H)

(16) [3-[3'-(Cyclohexyloxy)-4'-[[[(3-hydroxypropyl)sulfonyl]amino]carbonyl]-4-biphenylyl]propyl][(2R)-2-hydroxy-2-phenylethyl]carbamate
(−)ESI-MS (m/z): 693 (M−H)−

(17) tert-Butyl [(2R)-2-hydroxy-2-phenylethyl][3-[4'-[[[(3-hydroxypropyl)sulfonyl]amino]carbonyl]-3'-isopropoxy-4-biphenylyl]propyl]carbamate
(−)ESI-MS (m/z): 653 (M−H)−

(18) tert-Butyl [(2R)-2-hydroxy-2-phenylethyl][3-[4'-[[[(3-hydroxypropyl)sulfonyl]amino]carbonyl]-3'-isobutyl-4-biphenylyl]propyl]carbamate
(−)ESI-MS (m/z): 651 (M−H)−

(19) tert-Butyl [3-[3'-cyclopentyl-4'-[[[(3-hydroxypropyl)sulfonyl]amino]carbonyl]-4-biphenylyl]propyl]-[(2R)-2-hydroxy-2-phenylethyl]carbamate
(−)ESI-MS (m/z): 663 (M−H)−

(20) tert-Butyl [3-[3'-(cyclohexyloxy)-4'-[[[(3-hydroxypropyl)sulfonyl]amino]carbonyl]-4-biphenylyl]-propyl][(2R)-2-hydroxy-2-(4-nitrophenyl)ethyl]-carbamate
(−)ESI-MS (m/z): 738 (M−H)−

(21) tert-Butyl [3-[3'-cyclopentyl-4'-[[[(3-hydroxypropyl)sulfonyl]amino]carbonyl]-4-biphenylyl]propyl]-[(2R)-2-hydroxy-2-(4-nitrophenyl)ethyl]carbamate
(−)ESI-MS (m/z): 708 (M−H)−

(22) tert-Butyl [(2R)-2-(3-chlorophenyl)-2-hydroxyethyl][3-[4'-[[[(3-hydroxypropyl)sulfonyl]amino]-carbonyl]-3'-isopropoxy-4-biphenylyl]propyl]carbamate
(−)ESI-MS (m/z): 687, 688, 689 (M−H)−

(23) tert-Butyl [3-[3'-(cyclohexyloxy)-4'-[[[(3-hydroxypropyl)sulfonyl]amino]carbonyl]-4-biphenylyl]-propyl][(2R)-2-hydroxy-2-(3-pyridyl)ethyl]carbamate (−)ESI-MS (m/z): 694 (M−H)⁻

EXAMPLE 5

The following compounds were obtained according to a similar manner to that of Example 3.

(1) 4'-[2-[[(2R)-2-Hydroxy-2-phenylethyl]amino]ethoxy]-N-[(3-hydroxypropyl)sulfonyl]-3-isopropoxy-4-biphenylcarboxamide hydrochloride NMR (400 MHz, DMSO-d₆, δ): 1.37 (6H, d, J=5.9 Hz), 1.85-1.92 (2H, m), 3.10 (1H, dd, J=10.6, 12.4 Hz), 3.27 (1H, dd, J=1.8, 12.4 Hz), 3.44-3.57 (6H, m), 4.35-4.44 (2H, m), 4.75 (1H, t, J=5.1 Hz), 4.94-5.06 (2H, m), 6.23 (1H, d, J=3.7 Hz), 7.12 (2H, d, J=8.8 Hz), 7.31-7.44 (7H, m), 7.71 (1H, d, J=8.1 Hz), 7.75 (2H, d, J=8.8 Hz), 9.21 (2H, br), 11.0 (1H, br)

(−)ESI-MS (m/z): 555 (M−H)⁻

(2) 3-(Cyclohexyloxy)-4'-[2-[[(2R)-2-hydroxy-2-phenylethyl]amino]ethoxy]-N-[(3-hydroxypropyl)sulfonyl]-4-biphenylcarboxamide hydrochloride NMR (400 MHz, DMSO-d₆, δ): 1.30-1.63 (6H, m), 1.69-1.77 (2H, m), 1.84-1.91 (2H, m), 1.93-2.01 (2H, m), 3.10 (1H, dd, J=10.6, 12.4 Hz), 3.27 (1H, dd, J=2.2, 12.4 Hz), 3.44-3.58 (6H, m), 4.35-4.43 (2H, m), 4.74 (1H, t, J=5.1 Hz), 4.79-4.85 (1H, m), 5.01-5.05 (1H, m), 6.22 (1H, d, J=3.7 Hz), 7.12 (2H, d, J=8.8 Hz), 7.31-7.43 (7H, m), 7.74 (1H, d, J=8.1 Hz), 7.75 (1H, d, J=8.8 Hz), 9.20 (2H, br), 11.0 (1H, br)

(−)ESI-MS (m/z): 595 (M−H)⁻

(3) 3-Cyclopentyl-4'-[2-[[(2R)-2-hydroxy-2-phenylethyl]amino]ethoxy]-N-[(3-hydroxypropyl)sulfonyl]-4-biphenylcarboxamide hydrochloride NMR (400 MHz, DMSO-d₆, δ): 1.60-1.71 (4H, m), 1.77-1.91 (4H, m), 1.99-2.07 (2H, m), 3.08-3.13 (1H, m), 3.25-3.31 (2H, m), 3.44-3.47 (2H, m), 3.51-3.57 (4H, m), 4.34-4.42 (2H, m), 4.78 (1H, br), 5.01-5.05 (1H, m), 6.23 (1H, d, J=3.7 Hz), 7.11 (2H, d, J=8.8 Hz), 7.31-7.46 (6H, m), 7.53, (1H, dd, J=1.5, 8.1 Hz), 7.62 (1H, d, J=1.5 Hz), 7.70 (2H, d, J=8.8 Hz), 9.06 (1H, br), 9.21 (1H, br), 12.1 (1H, br)

(−)ESI-MS (m/z): 565 (M−H)⁻

(4) 4'-[2-[[(2R)-2-(3-Chlorophenyl)-2-hydroxyethyl]amino]ethoxy]-N-[(3-hydroxypropyl)sulfonyl]-3-isopropoxy-4-biphenylcarboxamide hydrochloride NMR (400 MHz, DMSO-d₆, δ): 1.37 (6H, d, J=6.2 Hz), 1.84-1.92 (2H, m), 3.12 (1H, dd, J=10.3, 12.4 Hz), 3.28-3.31 (1H, m), 3.44 (2H, t, J=5.1 Hz), 3.49-3.57 (4H, m), 4.34-4.42 (2H, m), 4.74 (1H, t, J=5.1 HZ), 4.94-5.07 (2H, m), 6.36 (1H, d, J=4.0 Hz), 7.12 (2H, d, J=8.8 Hz), 7.33-7.49 (6H, m), 7.71 (1H, d, J=8.1 Hz), 7.76 (2H, d, J=8.8 Hz), 9.12 (2H, br), 11.1 (1H, br)

(−)ESI-MS (m/z): 589 (M−H)⁻

(5) 4'-[2-[[(2R)-2-(3-Chlorophenyl)-2-hydroxyethyl]amino]ethoxy]-3-cyclopentyl-N-[(3-hydroxypropyl)sulfonyl]-4-biphenylcarboxamide hydrochloride NMR (400 MHz, DMSO-d₆, δ): 1.60-1.70 (4H, m), 1.77-1.91 (4H, m), 1.99-2.06 (2H, m), 3.12 (1H, dd, J=10.6, 12.4 Hz), 3.27-3.31 (1H, m), 3.44 (2H, t, J=4.8 Hz), 3.51-3.57 (4H, m), 4.32-4.41 (2H, m), 4.76 (1H, t, J=4.8 Hz), 5.02-5.06 (1H, m), 6.35 (1H, d, J=4.0 Hz), 7.10 (2H, d, J=8.8 Hz), 7.37-7.54 (6H, m), 7.62 (1H, d, J=1.5 Hz), 7.70 (2H, d, J=8.8 Hz), 9.04 (2H, br), 12.1 (1H, br)

(−)ESI-MS (m/z): 599 (M−H)⁻

(6) 3-(Cyclohexyloxy)-N-[(3-hydroxypropyl)sulfonyl]-4'-[2-[[(2R)-2-hydroxy-2-(3-pyridyl)ethyl]amino]ethoxy]-4-biphenylcarboxamide dihydrochloride NMR (400 MHz, DMSO-d₆, δ): 1.31-1.63 (6H, m), 1.69-1.78 (2H, m), 1.84-1.91 (2H, m), 1.93-2.00 (2H, m), 3.23-3.58 (8H, m), 4.36-4.44 (2H, m), 4.79-4.85 (1H, m), 5.27 (1H, dd, J=2.9, 9.5 Hz), 6.68 (1H, br), 7.12 (2H, d, J=8.8 Hz), 7.34 (1H, dd, J=1.5, 8.1 Hz), 7.40 (1H, d, J=1.5 Hz), 7.74 (1H, d, J=8.1 Hz), 7.75 (2H, d, J=8.8 Hz), 7.86 (1H, dd, J=5.5, 8.1 Hz), 8.34 (1H, d, J=8.1 Hz), 8.78 (1H, dd, J=1.5, 5.5 Hz), 8.84 (1H, d, J=1.5 Hz), 9.23 (1H, br)

(−)ESI-MS (m/z): 596 (M−H)⁻

(7) 4'-[2-[[(2R)-2-(4-Aminophenyl)-2-hydroxyethyl]amino]-ethyl]-3-(cyclohexyloxy)-N-[(3-hydroxypropyl)sulfonyl]-4-biphenylcarboxamide dihydrochloride NMR (400 MHz, DMSO-d₆, δ): 1.30-1.63 (6H, m), 1.71-1.76 (2H, m), 1.84-1.98 (4H, m), 3.00-3.12 (3H, m), 3.16-3.26 (3H, m), 4.49-3.58 (4H, m), 3.73 (1H, s), 4.78-4.82 (1H, m), 4.97-4.99 (1H, m), 6.25 (1H, s), 7.22-7.24 (2H, m), 7.34-7.43 (6H, m), 7.72-7.74 (3H, m), 8.89 (1H, br s), 9.20 (1H, br s), 9.57 (3H, br), 11.2 (1H, br s)

(−)ESI-MS (m/z): 594 (M−H)⁻

(8) 4'-[2-[[(2R)-2-(4-Aminophenyl)-2-hydroxyethyl]amino]-ethyl]-N-[(3-hydroxypropyl)sulfonyl]-3-isobutyl-4-biphenylcarboxamide dihydrochloride NMR (400 MHz, DMSO-d₆, δ): 0.87 (6H, d, J=6.6 Hz), 1.79-1.91 (3H, m), 2.73 (1H, d, J=7.0 Hz), 3.00-3.12 (3H, m), 3.16-3.26 (3H, m), 3.51-3.57 (4H, m), 4.94 (1H, dd, J=2.2, 9.9 Hz), 6.25 (1H, br), 7.22 (2H, d, J=8.1 Hz), 7.38 (2H, d, J=8.1 Hz), 7.42 (2H, d, J=8.1 Hz), 7.53-7.61 (3H, m), 7.70 (2H, d, J=8.1 Hz), 8.88 (1H, br), 9.17 (1H, br), 9.48 (3H, br), 12.1 (1H, br)

(−)ESI-MS (m/z): 552 (M−H)⁻

(9) 4'-[2-[[(2R)-2-(4-Aminophenyl)-2-hydroxyethyl]amino]-ethyl]-3-cyclopentyl-N-[(3-hydroxypropyl)sulfonyl]-4-biphenylcarboxamide dihydrochloride NMR (400 MHz, DMSO-d₆, δ): 1.60-1.71 (4H, m), 1.76-1.91 (4H, m), 1.98-2.07 (2H, m), 3.0-3.34 (7H, m), 3.51-3.58 (4H, m), 4.96-4.99 (1H, m), 6.25 (1H, br), 7.22 (2H, d, J=8.1 Hz), 7.37-7.48 (5H, m), 7.56 (1H, dd, J=1.5, 8.1 Hz), 7.64 (1H, d, J=1.5 Hz), 7.69 (2H, d, J=8.4 Hz), 8.89 (1H, br), 9.18 (1H, br), 9.51 (3H, br), 12.2 (1H, br)

(−)ESI-MS (m/z): 564 (M−H)⁻

(10) 4'-[2-[[(2R)-2-(4-Aminophenyl)-2-hydroxyethyl]amino]-ethyl]-3-(cyclohexyloxy)-N-[(2-hydroxyethyl)-sulfonyl]-4-biphenylcarboxamide dihydrochloride NMR (400 MHz, DMSO-d₆, δ): 1.31-1.63 (6H, m), 1.69-1.78 (2H, m), 1.92-2.01 (2H, m), 3.00-3.27 (6H, m), 3.65-3.85 (4H, m), 6.27 (1H, br), 7.29 (2H, d, J=8.4 Hz), 7.36 (1H, dd, J=1.5, 8.1 Hz), 7.39 (2H, d, J=8.4 Hz), 7.42 (1H, d, J=1.5 Hz), 7.45 (2H, d, J=8.4 Hz), 7.73 (2H, d, J=8.4 Hz), 7.78 (1H, d, J=8.1 Hz), 8.95 (1H, br), 9.31 (1H, br), 9.86 (3H, br), 11.1 (1H, br)

(−)ESI-MS (m/z): 580 (M−H)⁻

(11) 4'-[2-[[(2R)-2-(4-Aminophenyl)-2-hydroxyethyl]amino]-ethoxy]-3-(cyclohexyloxy)-N-[(3-hydroxypropyl)-sulfonyl]-4-biphenylcarboxamide dihydrochloride NMR (400 MHz, DMSO-d₆, δ): 1.31-1.63 (6H, m), 1.69-1.77 (2H, m), 1.84-1.91 (2H, m), 1.93-2.00 (2H, m), 3.04-3.30 (4H, m), 3.49-3.58 (4H, m), 4.35-4.44 (2H, m), 4.79-4.85 (1H, m), 5.04 (1H, dd, J=2.2, 10.3 Hz), 6.27 (1H, br), 7.12 (2H, d, J=8.8 Hz), 7.27 (2H, d, J=8.1 Hz), 7.34 (1H, dd, J=1.5, 8.1 Hz), 7.41 (1H, d, J=1.5 Hz), 7.45 (2H, d, J=8.1 Hz), 7.74 (1H, d, J=8.1 Hz), 7.75 (1H, d, J=8.4 Hz), 9.03 (1H, br), 9.31 (1H, br), 9.79 (3H, br), 11.1 (1H, br)

(−)ESI-MS (m/z): 610 (M−H)⁻

(12) 4'-[2-[[(2R)-2-(4-Aminophenyl)-2-hydroxyethyl]amino]-ethoxy]-3-cyclopentyl-N-[(3-hydroxypropyl)sulfonyl]-4-biphenylcarboxamide dihydrochloride NMR (400 MHz, DMSO-d$_6$, δ): 1.60-1.71 (4H, m), 1.76-1.91 (4H, m), 1.98-2.07 (2H, m), 3.05-3.35 (5H, m), 3.51-3.58 (4H, m), 4.33-4.42 (2H, m), 5.02 (1H, dd, J=2.2, 10.3 Hz), 6.25 (1H, br), 7.11 (2H, d, J=8.8 Hz), 7.24 (2H, d, J=7.7 Hz), 7.42-7.46 (3H, m), 7.53 (1H, dd, J=1.5, 8.1 Hz), 7.62 (1H, d, J=1.5 Hz), 7.70 (2H, d, J=8.8 Hz), 8.99 (1H, br), 9.23 (1H, br), 9.54 (3H, br), 12.1 (1H, br)

(−)ESI-MS (m/z): 580 (M−H)$^-$

(13) 4'-[2-[[(2R)-2-(3-Aminophenyl)-2-hydroxyethyl]amino]-ethyl]-3-(cyclohexyloxy)-N-[(3-hydroxypropyl)-sulfonyl]-4-biphenylcarboxamide dihydrochloride NMR (400 MHz, DMSO-d$_6$, δ): 1.30-1.63 (7H, m), 1.68-1.77 (2H, m), 1.84-1.91 (2H, m), 1.92-1.99 (2H, m), 2.95-3.28 (6H, m), 3.49-3.56 (4H, m), 4.81 (1H, heptuplet, J=4.0 Hz), 5.04 (1H, dd, J=2.2, 10.3 Hz), 6.38 (1H, br), 7.20 (1H, d, J=8.1 Hz), 7.28-7.46 (7H, m), 7.72-7.74 (3H, m), 8.97 (1H, br), 9.38 (1H, br), 9.88 (3H, br), 11.2 (1H, br)

(−)ESI-MS (m/z): 594 (M−H)$^-$

(14) 3-(Cycloheptyloxy)-N-[(3-hydroxypropyl)sulfonyl]-4'-[2-[[(2R)-2-hydroxy-2-(3-pyridyl)ethyl]amino]ethyl]-4-biphenylcarboxamide dihydrochloride NMR (400 MHz, DMSO-d$_6$, δ): 1.43-1.61 (6H, m), 1.64-1.73 (2H, m), 1.76-1.91 (4H, m), 2.00-2.09 (2H, m), 3.04-3.42 (4H, m), 3.49-3.56 (4H, m), 4.93-4.98 (1H, m), 5.25 (1H, dd, J=2.9, 9.2 Hz), 6.72 (1H, br), 7.34-7.36 (2H, m), 7.40 (2H, d, J=8.1 Hz), 7.72 (1H, d, J=7.7 Hz), 7.74 (2H, d, J=8.1 Hz), 7.90 (1H, dd, J=5.5, 8.1 Hz), 8.38 (1H, d, J=7.7 Hz), 8.80 (1H, dd, J=1.5, 5.5 Hz), 8.86 (1H, d, J=1.5 Hz), 9.16 (1H, br), 9.31 (1H, br), 11.2 (1H, br s)

(−)ESI-MS (m/z): 594 (M−H)$^-$

(15) 4'-[2-[[(2R)-2-(6-Chloro-3-pyridyl)-2-hydroxyethyl]-amino]ethyl]-3-(cyclohexyloxy)-N-[(2-hydroxyethyl)sulfonyl]-4-biphenylcarboxamide hydrochloride NMR (200 MHz, DMSO-d$_6$, δ): 1.24-2.02 (8H, m), 3.02-3.54 (6H, m), 3.67 (2H, t, J=6.0 Hz), 3.84 (2H, t, J=5.8 Hz), 4.76-4.87 (1H, m), 5.08-5.16 (1H, m), 6.48 (1H, br s), 7.32-7.44 (4H, m), 7.57 (1H, d, J=8.5 Hz), 7.67-7.80 (3H, m), 7.91 (1H, dd, J=2.3, 8.0 Hz), 8.46 (1H, d, J=2.0 Hz), 9.07 (1H, br s), 9.31 (1H, br s), 11.10 (1H, s)

(−)ESI-MS (m/z): 600 (M−H)$^-$

(16) 4'-[2-[[(2R)-2-Hydroxy-2-phenylethyl]amino]ethyl]-N-[(3-hydroxypropyl)sulfonyl]-3-isobutoxy-4-biphenylcarboxamide hydrochloride NMR (200 MHz, DMSO-d$_6$, δ): 1.04 (6H, d, J=7.0 Hz), 1.80-1.94 (2H, m), 2.03-2.17 (1H, m), 2.99-3.30 (6H, m), 3.46-3.59 (4H, m), 4.03 (2H, d, J=6.0 Hz), 4.74 (1H, t, J=5.0 Hz), 4.96-5.05 (1H, m), 6.23 (1H, d, J=3.5 Hz), 7.30-7.41 (9H, m), 7.67-7.77 (3H, m), 9.16 (1H, br)

(−)ESI-MS (m/z): 553 (M−H)$^-$

(17) 3-(Cyclohexyloxy)-N-[(2-hydroxyethyl)sulfonyl]-4'-[2-[[(1S,2R)-2-hydroxy-1-methyl-2-phenylethyl]amino]-ethyl]-4-biphenylcarboxamide hydrochloride NMR (200 MHz, DMSO-d$_6$, δ): 0.97 (3H, d, J=7.0 Hz), 1.33-2.02 (10H, m), 3.07-3.50 (5H, m), 3.66 (2H, t, J=6.0 Hz), 3.79-3.88 (2H, m), 4.76-4.88 (1H, m), 4.99-5.11 (1H, m), 5.22 (1H, br s), 6.15 (1H, d, J=4.0 Hz), 7.29-7.45 (9H, m), 7.71-7.81 (3H, m), 8.97 (2H, br s), 11.10 (1H, s)

(−)ESI-MS (m/z): 579 (M−H)$^-$

(18) 3-Cyclopentyl-4'-[2-[[(2R)-2-hydroxy-2-phenylethyl]-amino]ethyl]-N-[(3-hydroxypropyl)sulfonyl]-4-biphenyl-carboxamide hydrochloride NMR (200 MHz, DMSO-d$_6$, δ): 1.59-2.10 (10H, m), 2.99-3.30 (7H, m), 3.18-3.61 (4H, m), 4.73-4.81 (1H, m), 4.95-5.04 (1H, m), 6.23 (1H, d, J=4.0 Hz), 7.32-7.58 (9H, m), 7.64-7.71 (3H, m), 8.91 (1H, br s), 9.24 (1H, br s), 12.15 (1H, br s)

(−)ESI-MS (m/z): 549 (M−H)$^-$

(19) 3-(Cyclohexyloxy)-N-[(ethylamino)sulfonyl]-4'-[2-[[(2R)-2-hydroxy-2-(3-pyridyl)ethyl]amino]ethyl]-4-biphenylcarboxamide dihydrochloride NMR (200 MHz, DMSO-d$_6$, δ): 1.09 (3H, t, J=7.0 Hz), 1.29-1.81 (7H, m), 1.91-2.04 (2H, m), 2.94-3.46 (8H, m), 4.77-4.90 (1H, m), 5.25-5.34 (1H, m), 7.34-7.42 (4H, m), 7.71-7.80 (3H, m), 7.90-7.99 (2H, m), 8.46 (1H, d, J=8 Hz), 8.82-8.89 (2H, m), 9.25 (1H, br s), 9.40 (1H, br s), 10.90 (1H, s)

(−)ESI-MS (m/z): 565 (M−H)$^-$

(20) 3-Cyclohexylamino-4'-[2-[[(2R)-2-hydroxy-2-phenylethyl]amino]ethoxy]-N-[(3-hydroxypropyl)-sulfonyl]-4-biphenylcarboxamide dihydrochloride NMR (200 MHz, DMSO-d$_6$, δ): 1.26-1.89 (12H, m), 3.00-3.71 (9H, m), 4.35-4.43 (2H, m), 5.03 (1H, d, J=7.5 Hz), 6.82 (1H, d, J=8.5 Hz), 6.94 (1H, s), 7.10 (2H, d, J=8.5 Hz), 7.25-7.49 (5H, m), 7.70 (2H, d, J=8.5 Hz), 7.81 (1H, d, J=8.5 Hz), 9.00 (1H, br s), 9.26 (1H, br s)

(−)ESI-MS (m/z): 594 (M−H)$^-$

(21) 4'-[2-[[(2R)-2-Hydroxy-2-phenylethyl]amino]ethoxy]-N-[(3-hydroxypropyl)sulfonyl]-3-(isopropylthio)-4-biphenylcarboxamide hydrochloride NMR (200 MHz, DMSO-d$_6$, δ): 1.25 (6H, d, J=6.5 Hz), 1.85-1.99 (2H, m), 3.11-3.72 (9H, m), 4.32-4.45 (2H, m), 4.75 (1H, br s), 5.03 (1H, d, J=10 Hz), 6.22 (1H, d, J=3.5 Hz), 7.12 (2H, d, J=8.5 Hz), 7.31-7.43 (5H, m), 7.53-7.62 (2H, m), 7.71-7.75 (3H, m), 9.00 (1H, br s), 9.26 (1H, br s), 12.11 (1H, br s)

(−)ESI-MS (m/z): 571 (M−H)$^-$

(22) 4'-[2-[[(2R)-2-(3-Chlorophenyl)-2-hydroxyethyl]amino]ethyl]-N-[(3-hydroxypropyl)sulfonyl]-3-(isopropylthio)-4-biphenylcarboxamide hydrochloride NMR (200 MHz, DMSO-d$_6$, δ): 1.25 (6H, d, J=6.5 Hz), 1.85-1.99 (2H, m), 2.96-3.27 (6H, m), 3.50-3.72 (5H, m), 4.75 (1H, br s), 4.99 (1H, d, J=10 Hz), 6.35 (1H, d, J=4 Hz), 7.34-7.52 (6H, m), 7.54-7.67 (2H, m), 7.67-7.81 (3H, m), 8.87 (1H, br s), 8.98 (1H, br s), 12.13 (1H, br s)

(−)ESI-MS (m/z): 589, 591 (M−H)$^-$

(23) 3-(Cyclohexyloxy)-4'-[3-[[(2R)-2-hydroxy-2-phenylethyl]amino]propyl]-N-[(3-hydroxypropyl)-sulfonyl]-4-biphenylcarboxamide hydrochloride NMR (400 MHz, DMSO-d$_6$, δ): 1.28-1.65 (6H, m), 1.67-1.79 (2H, m), 1.83-2.11 (6H, m), 2.72 (2H, t, J=7.60 Hz), 2.94-3.04 (3H, m), 3.11-3.19 (1H, m), 3.47-3.59 (4H, m), 4.74 (1H, t, J=4.8 Hz), 4.77-4.85 (1H, m), 4.93-5.0 (1H, m), 6.18 (1H, d, J=3.6 Hz), 7.23-7.44 (9H, m), 7.67-7.76 (3H, m)

(−)ESI-MS (m/z): 593 (M−H)$^-$

(24) 4'-[3-[[(2R)-2-Hydroxy-2-phenylethyl]amino]propyl]-N-[(3-hydroxypropyl)sulfonyl]-3-isopropoxy-4-biphenylcarboxamide hydrochloride NMR (400 MHz, DMSO-d$_6$, δ): 1.37 (6H, d, J=6.0 Hz), 1.83-1.93 (2H, m), 1.95-2.09 (2H, m), 2.72 (2H, t, J=8.0 Hz), 2.93-3.05 (3H, m), 3.10-3.19 (1H, m), 3.47-3.60 (4H, m), 4.75 (1H, t, J=5.20 Hz), 4.91-5.03 (2H, m), 6.18 (1H, d, J=4 Hz), 7.29=7.44 (9H, m), 7.67-7.73 (3H, m)

(−)ESI-MS (m/z): 553 (M−H)$^-$

(25) 4'-[3-[[(2R)-2-Hydroxy-2-phenylethyl]amino]propyl]-N-[(3-hydroxypropyl)sulfonyl]-3-isobutyl-4-biphenylcarboxamide hydrochloride NMR (400 MHz, DMSO-d$_6$, δ): 0.87 (6H, d, J=6.4 Hz), 1.79-1.93 (3H, m), 1.95-2.08 (2H, m), 2.65-2.77 (4H, m), 2.93-3.04 (3H, m), 3.09-3.19 (1H, m), 3.47-3.59 (4H, m), 4.70-4.82 (1H, m), 4.91-5.01 (1H, m), 6.14-6.21 (1H, m), 7.27-7.43 (7H, m), 7.50-7.69 (5H, m), 12.11 (1H, s)

(−)ESI-MS (m/z): 551 (M−H)$^-$

(26) 3-Cyclopentyl-4'-[3-[[(2R)-2-hydroxy-2-phenylethyl]-amino]propyl]-N-[(3-hydroxypropyl)sulfonyl]-4-biphenylcarboxamide hydrochloride NMR (200 MHz, DMSO-$d_6$, δ): 1.52-2.20 (12H, m), 2.71 (2H, t, J=7.53 Hz), 2.87-3.29 (5H, m), 3.45-3.66 (4H, m), 4.69-4.86 (1H, m), 4.89-5.05 (1H, m), 6.18 (1H, d, J=4.02 Hz), 7.25-7.70 (12H, m)

(−)ESI-MS (m/z): 563 (M−H)$^-$

(27) 4'-[3-[[(2R)-2-(4-Aminophenyl)-2-hydroxyethyl]amino]-propyl]-3-(cyclohexyloxy)-N-[(3-hydroxypropyl)-sulfonyl]-4-biphenylcarboxamide dihydrochloride NMR (400 MHz, DMSO-$d_6$, δ): 1.28-1.64 (6H, m), 1.67-1.79 (2H, m), 1.82-2.11 (6H, m), 2.72 (2H, t, J=7.6 Hz), 2.89-3.19 (4H, m), 4.76-4.86 (1H, m), 4.95-5.04 (1H, m), 7.23-7.50 (8H, m), 7.65-7.78 (3H, m)

(−)ESI-MS (m/z): 608 (M−H)$^-$

(28) 4'-[3-[[(2R)-2-(4-Aminophenyl)-2-hydroxyethyl]amino]-propyl]-3-cyclopentyl-N-[(3-hydroxypropyl)sulfonyl]-4-biphenylcarboxamide dihydrochloride NMR (400 MHz, DMSO-$d_6$, δ): 1.41-1.71 (4H, m), 1.75-1.93 (4H, m), 1.96-2.10 (4H, m), 2.71 (2H, t, J=7.32 Hz), 2.92-3.04 (3H, m), 3.07-3.19 (1H, m), 3.26-3.36 (1H, m), 3.49-3.60 (4H, m), 4.95-5.01 (1H, m), 7.23-7.58 (8H, m), 7.60-7.71 (3H, m)

(−)ESI-MS (m/z): 578 (M−H)$^-$

(29) 4'-[3-[[(2R)-2-(3-Chlorophenyl)-2-hydroxyethyl]-amino]propyl]-N-[(3-hydroxypropyl)sulfonyl]-3-isopropoxy-4-biphenylcarboxamide hydrochloride NMR (400 MHz, DMSO-$d_6$, δ): 1.37 (6H, d, J=5.9 Hz), 1.84-1.93 (2H, m), 1.95-2.07 (2H, m), 2.72 (2H, t, J=7.5 Hz), 2.91-3.07 (3H, m), 3.14-3.24 (1H, m), 3.49-3.58 (4H, m), 4.92-5.03 (2H, m), 6.33 (1H, br s), 7.32-7.52 (8H, m), 7.68-7.73 (3H, m), 11.21 (1H, s)

(−)ESI-MS (m/z): 587 (M−H)$^-$

(30) 3-(Cyclohexyloxy)-N-[(3-hydroxypropyl)sulfonyl]-4'-[3-[[(2R)-2-hydroxy-2-(3-pyridyl)ethyl]amino]propyl]-4-biphenylcarboxamide dihydrochloride NMR (400 MHz, DMSO-$d_6$, δ): 1.28-1.65 (6H, m), 1.67-1.79 (2H, m), 1.81-2.13 (6H, m), 2.73 (2H, t, J=7.68 Hz), 2.90-3.05 (2H, m), 3.10-3.23 (1H, m), 3.27-3.38 (1H, m), 3.47-3.60 (4H, m), 4.76-4.86 (1H, m), 5.22-5.30 (1H, m), 7.32-7.44 (4H, m), 7.67-7.76 (3H, m), 7.91-7.98 (1H, m), 8.44 (1H, d, J=8.05 Hz), 8.79-8.89 (2H, m), 11.2 (1H, s)

(−)ESI-MS (m/z): 594 (M−H)$^-$

(31) N-[(3-Hydroxypropyl)sulfonyl]-4'-[3-[[(2R)-2-hydroxy-2-(3-pyridyl)ethyl]amino]propyl]-3-isobutoxy-4-biphenylcarboxamide dihydrochloride NMR (400 MHz, DMSO-$d_6$, δ): 1.04 (6H, d, J=7 Hz), 1.83-1.91 (2H, m), 1.99-2.13 (3H, m), 2.73 (2H, t, J=7.5 Hz), 2.95-3.03 (2H, m), 3.12-3.22 (1H, m), 3.28-3.37 (1H, m), 3.47-3.58 (4H, m), 4.03 (2H, d, J=6.2 Hz), 5.23-5.28 (1H, m), 7.33-7.39 (4H, m), 7.67-7.74 (3H, m), 7.91-7.97 (1H, m), 8.43 (1H, d, J=8 Hz), 8.79-8.89 (2H, m), 11.21 (1H, s)

(−)ESI-MS (m/z): 568 (M−H)$^-$

(32) N-[(3-Hydroxypropyl)sulfonyl]-4'-[3-[[(2R)-2-ydroxy-2-(3-pyridyl)ethyl]amino]propyl]-3-isopropoxy-4-biphenylcarboxamide dihydrochloride NMR (200 MHz, DMSO-$d_6$, δ): 1.37 (6H, d, J=6 Hz), 1.81-2.11 (4H, m), 2.73 (2H, t, J=7.3 Hz), 2.9-3.41 (4H, m), 3.46-3.61 (4H, m), 4.91-5.05 (1H, m), 5.19-5.31 (1H, m), 7.31-7.43 (4H, m), 7.66-7.76 (3H, m), 7.89-7.99 (1H, m), 8.44 (1H, d, J=8 Hz), 8.78-8.89 (2H, m), 11.2 (1H, s)

(−)ESI-MS (m/z): 554 (M−H)$^-$

EXAMPLE 6

A mixture of 3-[[[[4'-[2-[(tert-butoxycarbonyl)[(2R)-2-(6-chloro-3-pyridyl)-2-hydroxyethyl]amino]ethoxy]-3-(cyclohexyloxy)-4-biphenylyl]carbonyl]amino]sulfonyl]-propyl acetate (311 mg), 10% palladium on activated carbon (50% wet, 62 mg), ammonium formate (253 mg), methanol (6.2 ml) and water (6.2 ml) was refluxed for 3 hours. After cooling to room temperature, the catalyst was removed by filtration and washed with methanol. The filtrate was concentrated in vacuo and the residue was chromatographed on silica gel (eluent: hexane/ethyl acetate) to give 3-[[[[4'-[2-(tert-butoxycarbonyl)[(2R)-2-hydroxy-2-(3-pyridyl)ethyl]amino]ethoxy]-3-(cyclohexyloxy)-4-biphenylyl]carbonyl]amino]sulfonyl]propyl acetate (156 mg) as a white solid.

(−)ESI-MS (m/z): 738 (M−H)$^-$

EXAMPLE 7

To a solution of 3-[[[[4'-[2-[(tert-butoxycarbonyl)-[(2R)-2-hydroxy-2-(3-pyridyl)ethyl]amino]ethoxy]-3-(cyclohexyloxy)-4-biphenylyl]carbonyl]amino]sulfonyl]-propyl acetate (152 mg) in methanol (1.52 ml) and tetrahydrofuran (0.76 ml) was added 1N sodium hydroxide (0.616 ml) and the mixture was stirred at room temperature for 4 hours. The mixture was quenched by the addition of 1N hydrochloric acid (0.616 ml) and the solvent was concentrated in vacuo. The residual solid was dissolved in chloroform/methanol (4/1, 10 ml) and dried over magnesium sulfate. Filtration followed by evaporation gave a white solid (161 mg) which was chromatographed on silica gel (eluent: hexane/ethyl acetate) to give tert-butyl [2-[[3'-(cyclohexyloxy)-4'-[[[(3-hydroxypropyl)sulfonyl]amino]carbonyl]-4-biphenylyl]oxy]ethyl][(2R)-2-hydroxy-2-(3-pyridyl)ethyl]carbamate (135 mg) as a white solid.

(−)ESI-MS (m/z): 696 (M−H)$^-$

EXAMPLE 8

A mixture of tert-butyl [2-[3'-(cyclohexyloxy)-4'-[[[(3-hydroxporpyl)sulfonyl]amino]carbonyl]-4-biphenylyl]ethyl][(2R)-2-hydroxy-2-(4-nitrophenyl)ethyl]-carbamate (234 mg), iron powder (54 mg), ammonium chloride (8.6 mg), ethanol (3.51 ml) and water (1.17 ml) was refluxed for 50 minutes. After cooling to room temperature, the mixture was filtered through a Celite pad and washed with ethyl acetate (20 ml). The filtrate was washed with brine (20 ml) and dried over magnesium sulfate. Filtration followed by evaporation gave a crude product (217 mg) which was chromatographed on silica gel (eluent: hexane/ethyl acetate=1/2 to 1/3) to give tert-butyl [(2R)-2-(4-aminophenyl)-2-hydroxyethyl][2-[3'-(cyclohexyloxy)-4'-[[[(3-hydroxypropyl)sulfonyl]amino]carbonyl]-4-biphenylyl]ethyl]carbamate (136 mg) as a yellow solid.

(−)ESI-MS (m/z): 694 (M−H)$^-$

EXAMPLE 9

The following compounds were obtained according to a similar manner to that of Example 8.

(1) tert-Butyl [(2R)-2-(4-aminophenyl)-2-hydroxyethyl][2-[4'-[[[(3-hydroxypropyl)sulfonyl]amino]carbonyl]-3'-isobutyl-4-biphenylyl]ethyl]carbamate (−)ESI-MS (m/z): 652 (M−H)$^-$ (2) tert-Butyl [(2R)-2-(4-aminophenyl)-2-hydroxyethyl][2-[3'-cyclopentyl-4'-[[[(3-hydroxypropyl)sulfonyl]-amino]carbonyl]-4-biphenylyl]ethyl]carbamate (−)ESI-MS (m/z): 664 (M−H)$^-$ (3) tert-Butyl [(2R)-2-(4-aminophenyl)-2-hydroxyethyl][2-[[3'-(cyclohexyloxy)-4'-[[[(3-hydroxypropyl)sulfonyl]amino]carbonyl]-4-biphenylyl]oxy]ethyl]-carbamate (−)ESI-MS (m/z): 710 (M−H)$^-$ (4) tert-Butyl [(2R)-2-(4-aminophenyl)-2-hydroxyethyl][2-[[3'-cyclopentyl-4'-[[[(3-hydroxypropyl)sulfonyl]-amino]carbonyl]-4-biphenylyl]oxy]ethyl]carbamate
(−)ESI-MS (m/z): 680 (M−H)⁻
(5) tert-Butyl [(2R)-2-(3-aminophenyl)-2-hydroxyethyl][2-[3'-(cyclohexyloxy)-4'-[[[(3-hydroxypropyl)sulfonyl]-amino]carbonyl]-4-biphenylyl]ethyl]carbamate
(6) tert-Butyl [(2R)-2-(4-aminophenyl)-2-hydroxyethyl][3-[3'-(cyclohexyloxy)-4'-[[[(3-hydroxypropyl)sulfonyl]-amino]carbonyl]-4-biphenylyl]propyl]carbamate
(−)ESI-MS (m/z): 708 (M−H)⁻
(7) tert-Butyl [(2R)-2-(4-aminophenyl)-2-hydroxyethyl][3-[3'-cyclopentyl-4'-[[[(3-hydroxypropyl)sulfonyl]-amino]carbonyl]-4-biphenylyl]propyl]carbamate
(−)ESI-MS (m/z): 678 (M−H)⁻

EXAMPLE 10

A mixture of tert-butyl [2-[4'-[[[[2-(benzyloxy)-ethyl]sulfonyl]amino]carbonyl]-3'-(cyclohexyloxy)-4-biphenylyl]ethyl][(2R)-2-hydroxy-2-(4-nitrophenyl)ethyl]-carbamate (215 mg), 10% palladium on activated carbon (50% wet, 645 mg), ammonium formate (845 mg), methanol (6.45 ml) and water (0.65 ml) was refluxed for 20 minutes. After cooling to room temperature, the catalyst was removed by filtration and washed with methanol. The filtrate was concentrated in vacuo and the residue was chromatographed on silica gel (eluent: hexane/ethyl acetate) to give tert-butyl [(2R)-2-(4-aminophenyl)-2-hydroxyethyl][2-[3'-(cyclohexyloxy)-4'-[[[(2-hydroxyethyl)sulfonyl]amino]carbonyl]-4-biphenylyl]ethyl]-carbamate (123 mg) as a pale-yellow solid.
(−)ESI-MS (m/z): 680 (M−H)⁻

EXAMPLE 11

To a solution of 4'-[2-[(tert-butoxycarbonyl)[(2R)-2-hydroxy-2-(3-pyridyl)ethyl]amino]ethyl]-3-(cycloheptyloxy)-4-biphenylcarboxylic acid (457 mg) in N,N-dimethylformamide (4.6 ml) was added N,N'-carbonyldiimidazole (155 mg) and the mixture was stirred at room temperature for 1 hour. To the mixture were added 3-(aminosulfonyl)propyl acetate (173 mg) and 1,8-diazabicyclo[5.4.0]undec-7-ene (0.143 ml) and the mixture was stirred at 120° C. for 24 hours. After cooling to room temperature, the mixture was quenched by the addition of pH 6.86 buffer (20 ml) and extracted with ethyl acetate (20 ml×2). The combined extracts were washed with pH 6.86 buffer (40 ml×2) and brine (40 ml), and dried over magnesium sulfate. Filtration followed by evaporation gave a yellow solid (486 mg) which was chromatographed on silica gel (hexane/ethyl acetate) to give 3-[[[[4'-[2-[(tert-butoxycarbonyl)[(2R)-2-hydroxy-2-(3-pyridyl)ethyl]-amino]ethyl]-3-(cycloheptyloxy)-4-biphenylyl]carbonyl]-amino]sulfonyl]propyl acetate (276 mg) as a pale yellow solid.
(−)ESI-MS (m/z): 736 (M−H)⁻

EXAMPLE 12

The following compound was obtained according to a similar manner to that of Example 7.
tert-Butyl [2-[3'-(cycloheptyloxy)-4'-[[[(3-hydroxypropyl)sulfonyl]amino]carbonyl]-4-biphenylyl]ethyl][(2R)-2-hydroxy-2-(3-pyridyl)ethyl]carbamate
(−)ESI-MS (m/z): 694 (M−H)⁻

EXAMPLE 13

To a solution of 4'-[2-[(tert-butoxycarbonyl)[(2R)-2-(6-chloro-3-pyridyl)-2-(tetrahydro-2H-pyran-2-yloxy)ethyl]amino]ethyl]-3-(cyclohexyloxy)-4-biphenylcarboxylic acid (180 mg) in N,N-dimethylformamide (1 ml) were added 2-(aminosulfonyl)ethyl acetate (205 mg), N,N-dimethylaminopyridine (65 mg) and 1-[3-(dimethylamino)propyl]-3-ethylcarbodiimide hydrochloride (61 mg) at room temperature and the mixture was stirred at the same temperature for 4 days. The mixture was poured into 0.5N hydrochloric acid and extracted with ethyl acetate. The organic layer was washed with brine, dried over sodium sulfate and evaporated under reduced pressure to give an acylsulfonamide product. To a solution of the above product in methanol (3 ml) was added 4-methylbenzene-sulfonic acid (30 mg) at room temperature and the mixture was stirred at the same temperature overnight. The mixture was portioned into a mixture of ethyl acetate and water. The organic layer was separated, washed with brine, dried over sodium sulfate and evaporated under reduced pressure. The residue was purified by column chromatography on silica gel (chloroform/methanol=95/5) to give tert-butyl [(2R)-2-(6-chloro-3-pyridyl)-2-hydroxyethyl][2-[3'-(cyclohexyloxy)-4'-[[[(2-hydroxyethyl)sulfonyl]amino]carbonyl]-4-biphenylyl]ethyl]carbamate (49 mg).
(+)ESI-MS (m/z): 724 (M+Na)⁺

EXAMPLE 14

The following compound was obtained according to a similar manner to that of Example 6.
tert-Butyl [2-[3'-(cyclohexyloxy)-4'-[[[(2-hydroxyethyl)sulfonyl]amino]carbonyl]-4-biphenylyl]ethyl]-[(2R)-2-hydroxy-2-(3-pyridyl)ethyl]carbamate
(+)ESI-MS (m/z): 668 (M+H)⁺

EXAMPLE 15

To a solution of tert-butyl [2-(4-bromophenyl)ethyl]-[(2R)-2-hydroxy-2-(3-pyridyl)ethyl]carbamate (331 mg) in 1,4-dioxane (3.3 ml) were added [4-[[[(3-hydroxypropyl)sulfonyl]amino]carbonyl]-3-isopropoxyphenyl]boronic acid (325 mg), tetrakis(triphenylphosphine)palladium (91 mg) and aqueous solution of sodium carbonate (2M, 1.4 ml), and the mixture was stirred at 80° C. for 3 hours under nitrogen. The mixture was portioned into a mixture of ethyl acetate and water. The organic layer was separated, washed with brine, dried over sodium sulfate and evaporated under reduced pressure. The residue was purified by column chromatography on silica gel (ethyl acetate/methanol=100/3) to give tert-butyl [2-[4'-[[[(3-hydroxypropyl)sulfonyl]amino]carbonyl]-3'-isopropoxy-4-biphenylyl]-ethyl][(2R)-2-hydroxy-2-(3-pyridyl)ethyl]carbamate (108 mg).
(+)ESI-MS (m/z): 664 (M+Na)⁺

EXAMPLE 16

The following compounds were obtained according to a similar manner to that of Example 11.
(1) tert-Butyl [(2R)-2-hydroxy-2-phenylethyl][2-[4'-[[[(3-hydroxypropyl)sulfonyl]amino]carbonyl]-3'-isobutoxy-4-biphenylyl]ethyl]carbamate
(+)ESI-MS (m/z): 677 (M+Na)⁺
(2) tert-Butyl [2-[3'-cyclopentyl-4'-[[[(3-hydroxypropyl)sulfonyl]amino]carbonyl]-4-biphenylyl]ethyl]-[(2R)-2-hydroxy-2-phenylethyl]carbamate
(+)ESI-MS (m/z): 673 (M+Na)⁺
(3) 3-[[[[4'-[3-[(tert-Butoxycarbonyl)[(2R)-2-hydroxy-2-(3-pyridyl)ethyl]amino]propyl]-3-isobutoxy-4-biphenylyl]carbonyl]amino]sulfonyl]propyl acetate
(−)ESI-MS (m/z): 710 (M−H)⁻

(4) 3-[[[[4'-[3-[(tert-Butoxycarbonyl)[(2R)-2-hydroxy-2-(3-pyridyl)ethyl]amino]propyl]-3-isopropoxy-4-biphenylyl]carbonyl]amino]sulfonyl]propyl acetate
(−)ESI-MS (m/z): 696 (M−H)⁻

(5) Methyl 3-[[[[4'-[2-[(tert-butoxycarbonyl)[(2R)-2-hydroxy-2-phenylethyl]amino]ethyl]-3-(cyclohexyloxy)-4-biphenylyl]carbonyl]amino]sulfonyl]propanoate
(−)ESI-MS (m/z): 707 (M−H)⁻

(6) 4-[[[[4'-[2-[(tert-Butoxycarbonyl)[(2R)-2-hydroxy-2-phenylethyl]amino]ethyl]-3-(cyclohexyloxy)-4-biphenylyl]carbonyl]amino]sulfonyl]butyl acetate
(−)ESI-MS (m/z): 735 (M−H)⁻

EXAMPLE 17

The following compounds were obtained according to a similar manner to that of Example 13.
(1) tert-Butyl [2-[3'-(cyclohexyloxy)-4'-[[[(2-hydroxyethyl)sulfonyl]amino]carbonyl]-4-biphenylyl]-ethyl][(2R)-2-hydroxy-2-phenylethyl]carbamate
(+)ESI-MS (m/z): 689 (M+Na)⁺
(2) tert-Butyl [2-[3'-(cyclohexyloxy)-4'-[[[(2-hydroxyethyl)sulfonyl]amino]carbonyl]-4-biphenylyl]ethyl]-[(1S,2R)-2-hydroxy-1-methyl-2-phenylethyl]carbamate
(+)ESI-MS (m/z): 703 (M+Na)⁺

EXAMPLE 18

To a solution of tert-butyl [2-[4'-(aminosulfonyl)-3'-(cyclohexyloxy)-4-biphenylyl]ethyl][(2R)-2-phenyl-2-(tetrahydro-2H-pyran-2-yloxy)ethyl]carbamate (188 mg) in N,N-dimethylformamide (1 ml) were added 4-[(tert-butoxycarbonyl)amino]butanoic acid (146 mg), N,N-dimethylaminopyridine (40.6 mg) and 1-[3-(dimethylamino)propyl]-3-ethylcarbodiimide hydrochloride (149 mg) at room temperature and the mixture was stirred at the same temperature for 3 days. The mixture was diluted with ethyl acetate, and washed with aqueous sodium bicarbonate solution, 0.1N hydrochloric acid and brine. The organic layer was dried over sodium sulfate and evaporated under reduced pressure to give an acylsulfonamide product. To a solution of the product in methanol (3 ml) was added 4-methylbenzenesulfonic acid (36 mg) at room temperature and the mixture was stirred at the same temperature for 2 days. The mixture was diluted with ethyl acetate, and washed with water and brine. The organic layer was dried over sodium sulfate and evaporated under reduced pressure. The residue was purified by column chromatography on silica gel (hexane/ethyl acetate=6/4) to give tert-butyl [2-[4'-[[[4-[(tert-butoxycarbonyl)amino]butanoyl]amino]sulfonyl]-3'-(cyclohexyloxy)-4-biphenylyl]ethyl][(2R)-2-hydroxy-2-phenylethyl]carbamate (117 mg).
(+)ESI-MS (m/z): 802 (M+Na)⁺

EXAMPLE 19

To a solution of tert-butyl [2-[4'-[[[4-[(tert-butoxycarbonyl)amino]butanoyl]amino]sulfonyl]-3'-(cyclohexyloxy)-4-biphenylyl]ethyl][(2R)-2-hydroxy-2-phenylethyl]carbamate (110 mg) in ethyl acetate (1 ml) was added hydrogen chloride in ethyl acetate (4N, 1 ml) at room temperature and the mixture was stirred at the same temperature for 6 hours. The mixture was filtered to collect the precipitate and the precipitate was washed with ethyl acetate/hexane (1:1). The precipitate was dried under reduced pressure to give 4-amino-N-[[3-(cyclohexyloxy)-4'-[2-[[(2R)-2-hydroxy-2-phenylethyl]-amino]ethyl]-4-biphenylyl]sulfonyl]butanamide dihydrochloride (85 mg).

NMR (200 MHz, DMSO-$d_6$, δ): 1.25-1.98 (12H, m), 2.36 (2H, t, J=7.3 Hz), 2.64-2.77 (2H, m), 2.99-3.28 (6H, m), 4.76-4.85 (1H, m), 4.97-5.07 (1H, m), 6.24 (1H, d, J=4.0 Hz), 7.3-7.43 (9H, m), 7.73 (2H, d, J=8.5 Hz), 7.88 (1H, d, J=8.0 Hz), 7.98 (2H, br s), 8.98 (1H, br s), 9.41 (1H, br s), 11.94 (1H, br s)
(−)ESI-MS (m/z): 578 (M−H)⁻

EXAMPLE 20

The following compound was obtained according to a similar manner to that of Example 18.
tert-Butyl [2-[4'-[[[[(tert-butoxycarbonyl)amino]-acetyl]amino]sulfonyl]-3'-(cyclohexyloxy)-4-biphenylyl]-ethyl][(2R)-2-hydroxy-2-phenylethyl]carbamate
(+)ESI-MS (m/z): 774 (M+Na)⁺

EXAMPLE 21

The following compounds were obtained according to a similar manner to that of Example 19.
(1) 2-Amino-N-[[3-(cyclohexyloxy)-4'-[2-[[(2R)-2-hydroxy-2-phenylethyl]amino]ethyl]-4-biphenylyl]sulfonyl]-acetamide dihydrochloride
NMR (200 MHz, DMSO-$d_6$, δ) 1.24-1.98 (10H, m), 2.99-3.28 (6H, m), 3.65 (2H, br s), 4.74-4.87 (1H, m), 4.99-5.08 (1H, m), 6.25 (1H, br s), 7.3-7.45 (9H, m), 7.72 (2H, d, J=8.0 Hz), 7.93 (1H, d, J=8.5 Hz), 8.26 (3H, br s), 8.99 (1H, br s), 9.51 (1H, br s), 12.52 (1H, br s)
(−)ESI-MS (m/z): 550 (M−H)⁻

(2) 3-[[[[3-(Cyclohexyloxy)-4'-[2-[[(2R)-2-hydroxy-2-phenylethyl]amino]ethyl]-4-biphenylyl]carbonyl]-amino]sulfonyl]propanoic acid hydrochloride
NMR (200 MHz, DMSO-$d_6$, δ): 1.2-2.2 (10H, m), 2.74 (2H, t, J=7.2 Hz), 3.0-3.4 (6H, m), 3.75 (1H, t, J=7.2 Hz), 4.7-4.85 (1H, m), 4.9-5.0 (1H, m), 6.22 (1H, d, J=3.6 Hz), 7.3-7.4 (10H, m), 7.72 (2H, dd, J=2.1, 8.1 Hz)

(3) 3-(Cyclohexyloxy)-N-[(3-hydroxy-3-methylbutyl)sulfonyl]-4'-[2-[[(2R)-2-hydroxy-2-phenylethyl]-amino]ethyl]-4-biphenylcarboxamide hydrochloride
NMR (400 MHz, DMSO-$d_6$, δ): 1.11 (1H, s), 1.12-2.0 (12H, m), 2.98-3.06 (2H, m), 3.15-3.42 (6H, m), 3.51-3.57 (2H, m), 4.55 (1H, s), 4.75-4.82 (1H, m), 4.9.1-4.94 (1H, m), 6.21 (1H, d, J=1.7 Hz), 7.3-7.42 (10H, m), 7.73 (2H, d, J=4.1 Hz)
(−)ESI-MS (m/z): 607 (M−H)⁻

(4) N-[(3-Amino-3-oxopropyl)sulfonyl]-3-(cyclohexyloxy)-4'-[2-[[(2R)-2-hydroxy-2-phenylethyl]amino]ethyl]-4-biphenylcarboxamide hydrochloride
NMR (400 MHz, DMSO-$d_6$, δ): 1.38-1.72 (10H, m), 2.3-2.7 (2H, m), 2.6-2.9 (2H, m), 2.9-3.2 (2H, m), 3.3-3.5 (4H, m), 4.8-4.9 (1H, m), 4.92-4.96 (1H, m), 6.22 (1H, d, J=3.4 Hz), 7.03 (1H, s), 7.31-7.41 (8H, m), 7.52 (1H, s), 7.73 (2H, d, J=11.3 Hz)
(+)ESI-MS (m/z): 594 (M+H)⁺ (free)

(5) 3-(Cyclohexyloxy)-N-[(4-hydroxybutyl)sulfonyl]-4'-[2-[[(2R)-2-hydroxy-2-phenylethyl]amino]ethyl]-4-biphenylcarboxamide hydrochloride
NMR (400 MHz, DMSO-$d_6$, δ): 1.32-2.00 (14H, m), 3.06-3.65 (10H, m), 4.02 (1H, t, J=6.1 Hz), 4.78-4.82 (1H, m), 4.99 (1H, d, J=9.4 Hz), 6.2-6.23 (1H, m), 7.3-7.41 (10H, m), 7.7-7.74 (2H, m), 8.88 (1H, br s), 9.21 (1H, br s)
(−)ESI-MS (m/z): 593 (M−H)⁻

EXAMPLE 22

The following compound was obtained according to a similar manner to that of Example 2 followed by a similar manner to that of Example 3.

4-[(7S)-7-[[(2R)-2-(4-Chlorophenyl)-2-hydroxyethyl]-amino]-5,6,7,8-tetrahydro-2-naphthalenyl]-N-[(3-hydroxypropyl)sulfonyl]benzamide hydrochloride NMR (200 MHz, DMSO-$d_6$, δ): 1.4-2.4 (8H, m), 2.7-3.8 (6H, m), 4.11 (1H, m), 5.06 (1H, m), 6.34 (1H, m), 7.25 (1H, d, J=8.0 Hz), 7.3-7.5 (6H, m), 7.80 (2H, d, J=8.0 Hz), 8.02 (2H, d, J=8.0 Hz)

ESI-MS (m/z): 542 (M+H)

EXAMPLE 23

To a solution of 4'-[2-[(tert-butoxycarbonyl)[(2R)-2-(3-chlorophenyl)-2-hydroxyethyl]amino]ethyl]-3-(isopropylthio)-4-biphenylcarboxylic acid (150 mg) in tetrahydrofuran (1.5 ml) was added N,N'-carbonyldiimidazole (64 mg) and stirred at room temperature for 30 minutes. To the mixture were added 3-(aminosulfonyl)propyl acetate (67 mg) and 1,8-diazabicyclo[5.4.0]-7-undecene (55 μl) and stirred at room temperature, and then stirred at 50° C. for 3 hours. The reaction mixture was poured into 0.1N hydrochloric acid and ethyl acetate and the organic layer was separated. The organic layer was washed with water and brine, dried over magnesium sulfate and concentrated in vacuo to give 3-[[[[4'-[2-[(tert-butoxycarbonyl)[(2R)-2-(3-chlorophenyl)-2-hydroxyethyl]amino]ethyl]-3-(isopropylthio)-4-biphenylyl]carbonyl]amino]sulfonyl]propyl acetate (72 mg). To a solution of the product (72 mg) in methanol (2.0 ml) and tetrahydrofuran (2.0 ml) was added sodium hydroxide aqueous solution (1N, 532 μl) and stirred at room temperature for 10 minutes. To the mixture was added hydrochloric acid aqueous solution (1N, 532 μl) and diluted with ethyl acetate. The solution was poured into water and ethyl acetate and the organic layer was separated. The organic layer was washed with water and brine, dried over magnesium sulfate and concentrated in vacuo. The residue was purified with silica gel column chromatography to give tert-butyl [(2R)-2-(3-chlorophenyl)-2-hydroxyethyl][2-[4'-[[[(3-hydroxypropyl)sulfonyl]amino]carbonyl]-3'-(isopropylthio)-4-biphenylyl]-ethyl]carbamate (49 mg).

(−)ESI-MS (m/z): 689, 691 (M−H)⁻

EXAMPLE 24

The following compound was obtained according to a similar manner to that of Example 23.

tert-Butyl [(2R)-2-hydroxy-2-phenylethyl][2-[3'-(isopropylthio)-4'-[[[(2-methoxyethyl)sulfonyl]amino]-carbonyl]-4-biphenylyl]ethyl]carbamate (−)ESI-MS (m/z): 655 (M−H)⁻

EXAMPLE 25

To a solution of tert-butyl [(2R)-2-hydroxy-2-phenylethyl] [2-[3'-(isopropylthio)-4'-[[[(2-methoxyethyl)sulfonyl] amino]carbonyl]-4-biphenylyl]ethyl]carbamate (3.92 g) in ethyl acetate (20 ml) was added hydrogen chloride ethyl acetate solution (4M, 20 ml) and stirred at room temperature overnight. The resulting solid was collected by filtration and dried to give 4'-[2-[[(2R)-2-hydroxy-2-phenylethyl]amino] ethyl]-3-(isopropylthio)-N-[(2-methoxyethyl)sulfonyl]-4-biphenylcarboxamide hydrochloride (3.15 g).

NMR (200 MHz, DMSO-$d_6$, δ): 1.26 (6H, d, J=6.6 Hz), 3.06-3.28 (6H, m), 3.28 (3H, s), 3.61-3.78 (1H, m), 3.78 (4H, s), 4.97-5.03 (1H, m), 6.23 (1H, d, J=3.6 Hz), 7.31-7.42 (7H, m), 7.55-7.64 (2H, m), 7.70-7.74 (3H, m), 8.91 (1H, br s), 9.25 (1H, br s), 12.2 (1H, br s)

(−)ESI-MS (m/z): 555 (M−H)⁻

EXAMPLE 26

To a solution of tert-butyl [(2R)-2-hydroxy-2-phenylethyl] [2-(4-iodophenoxy)ethyl]carbamate (250 mg) and [3-(cyclohexylamino)-4-[[[(3-hydroxypropyl)sulfonyl]amino]-carbonyl]phenyl]boronic acid (258 mg) in toluene (3.0 ml) and ethanol (750 μl) were added 1,1'-bis(diphenylphosphino)ferrocene (29 mg), sodium carbonate aqueous solution (2M, 830 μl) and [1,1'-bis(diphenylphosphino)ferrocene]dichloropalladium (38 mg) at room temperature under nitrogen and stirred at 75° C. for 2 hours. The reaction mixture was poured into 0.5N hydrochloric acid (20 ml) and ethyl acetate (20 ml), added active carbon and stirred at room temperature for 30 minutes. The mixture was filtered and separated the organic layer. The organic layer was washed with brine, dried over magnesium sulfate and concentrated in vacuo. The residue was purified with silica gel column chromatography to give tert-butyl [2-[[3'-(cyclohexylamino)-4'-[[[(3-hydroxypropyl) sulfonyl]amino]carbonyl]-4-biphenylyl]oxy]ethyl][(2R)-2-hydroxy-2-phenylethyl]-carbamate (127 mg).

(−)ESI-MS (m/z): 694 (M−H)⁻

EXAMPLE 27

The following compounds were obtained according to a similar manner to that of Example 26.
(1)  3-[[[[4'-[2-[(tert-Butoxycarbonyl)[(2R)-2-hydroxy-2-phenylethyl]amino]ethoxy]-3-(isopropylthio)-4-biphenylyl]carbonyl]amino]sulfonyl]propyl acetate
(−)ESI-MS (m/z): 713 (M−H)⁻
(2) tert-Butyl [(2R)-2-hydroxy-2-phenylethyl][2-[[4'-[[[(3-hydroxypropyl)sulfonyl]amino]carbonyl]-3'-(isopropylthio)-4-biphenylyl]oxy]ethyl]carbamate
(−)ESI-MS (m/z): 671 (M−H)⁻
(3)  3-[[[[4'-[2-[(tert-Btoxycarbonyl)[(2R)-2-(3-chlorophenyl)-2-hydroxyethyl]amino]ethyl]-3-(cyclohexyloxy)-4-biphenylyl]carbonyl]amino]-sulfonyl]propyl acetate
(−)ESI-MS (m/z): 755 (M−H)⁻
(4)  3-[[[[4'-[2-[(tert-Butoxycarbonyl)[(2R)-2-(3-fluorophenyl)-2-hydroxyethyl]amino]ethyl]-3-(cyclohexyloxy)-4-biphenylyl]carbonyl]amino]-sulfonyl]propyl acetate
(+)ESI-MS (m/z): 763 (M+Na)⁺

EXAMPLE 28

The mixture of 3-[[[[4'-[2-[(tert-butoxycarbonyl)-[(2R)-2-(3-chlorophenyl)-2-hydroxyethyl]amino]ethyl]-3-(cyclohexyloxy)-4-biphenylyl]carbonyl]amino]sulfonyl]-propyl acetate (269 mg) in hydrogen chloride methanol solution (10%, 2.7 ml) was stirred at room temperature overnight. The reaction mixture was concentrated in vacuo and the residue was recrystallized from aqueous ethanol (50%) to give 4'-[2-[[(2R)-2-(3-chlorophenyl)-2-hydroxyethyl]amino]ethyl]-3-(cyclohexyloxy)-N-[(3-hydroxypropyl)sulfonyl]-4-biphenylcarboxamide hydrochloride (161 mg).

NMR (200 MHz, DMSO-$d_6$, δ): 1.23-2.03 (12H, m), 2.98-3.32 (6H, m), 3.36-3.61 (4H, m), 4.72-4.89 (1H, m), 5.04 (1H, d, J=8.0 Hz), 6.41 (1H, br s), 7.33-7.48 (8H, m), 7.67-7.82 (3H, m), 8.96 (1H, br s), 9.28 (1H, br s), 11.17 (1H, s)

(−)ESI-MS (m/z): 613 (M−H)⁻

EXAMPLE 29

The following compound was obtained according to a similar manner to that of Example 28.

3-(Cyclohexyloxy)-4'-[2-[[(2R)-2-(3-fluorophenyl)-2-hydroxyethyl]amino]ethyl]-N-[(3-hydroxypropyl)sulfonyl]-4-biphenylcarboxamide hydrochloride NMR (200 MHz, DMSO-$d_6$, δ): 1.39-1.94 (12H, m), 3.00-3.27 (6H, m), 3.48-3.59 (4H, m), 4.65-4.88 (2H, m), 5.03 (1H, d, J=9.5 Hz), 6.36 (1H, d, J=3.5 Hz), 7.11-7.51 (8H, m), 7.68-7.79 (3H, m), 9.44 (2H, br s)

(−)ESI-MS (m/z): 597 (M−H)−

EXAMPLE 30

To a solution of 3-[[[[4'-[3-[(tert-butoxycarbonyl)-[(2R)-2-hydroxy-2-(3-pyridyl)ethyl]amino]propyl]-3-isobutoxy-4-biphenylyl]carbonyl]amino]sulfonyl]propyl acetate (108 mg) in methanol (1.08 ml) and tetrahydrofuran (0.324 ml) was added 1N aqueous sodium hydroxide solution (0.455 ml) and the mixture was stirred at room temperature for 45 minutes. The reaction mixture was concentrated under reduced pressure and the pH value was adjusted to 6.0 with 0.1N hydrochloric acid. The mixture was extracted with ethyl acetate (twice) and the extracts were washed with water and brine, and dried over magnesium sulfate. Filtration followed by evaporation under reduced pressure gave tert-butyl [3-[4'-[[[(3-hydroxypropyl)sulfonyl]amino]carbonyl]-3'-isobutoxy-4-biphenylyl]-propyl][(2R)-2-hydroxy-2-(3-pyridyl)ethyl]carbamate (91.1 mg) as a white solid (foam).

(−)ESI-MS (m/z): 668 (M−H)−

EXAMPLE 31

To a solution of 3-[[[[4'-[3-[(tert-butoxycarbonyl)-[(2R)-2-hydroxy-2-(3-pyridyl)ethyl]amino]propyl]-3-isopropoxy-4-biphenylyl]carbonyl]amino]sulfonyl]propyl acetate (221 mg) in methanol (2.21 ml) and tetrahydrofuran (1.11 ml) was added 1N sodium hydroxide (0.950 ml) and the mixture was stirred at room temperature for 1 hour. Methanol and tetrahydrofuran were removed by evaporation under reduced pressure and to the residue was added water (50 ml). The mixture was acidified with 1N hydrochloric acid (pH=5.4) and extracted with ethyl acetate (50 ml×2). The combined organic layer was washed with water and brine, and dried over magnesium sulfate. Filtration followed by evaporation under reduced pressure gave tert-butyl [3-[4'-[[[(3-hydroxypropyl)sulfonyl]amino]carbonyl]-3'-isopropoxy-4-biphenylyl]propyl][(2R)-2-hydroxy-2-(3-pyridyl)ethyl]carbamate (212 mg) as a white solid.

(−)ESI-MS (m/z): 654 (M−H)−

EXAMPLE 32

The following compound was obtained according to a similar manner to that of Preparation 3.

3-[[[[4'-[2-[(tert-Butoxycarbonyl)[(2R)-2-hydroxy-2-phenylethyl]amino]ethyl]-3-(cyclohexyloxy)-4-biphenylyl]-carbonyl]amino]sulfonyl]propanoic acid NMR (200 MHz, DMSO-$d_6$, δ): 1.2-1.8 (10H, m), 1.33 (9H, s), 2.6-2.9 (4H, m), 3.0-3.6 (4H, m), 3.75 (2H, t, J=7 Hz), 4.62-4.82 (2H, m), 5.45 (1H, br s), 7.2-7.4 (9H, m), 7.6-7.73 (3H, m)

(+)ESI-MS (m/z): 695 (M+H)+

EXAMPLE 33

Under a nitrogen atmosphere, methylmagnesium chloride (3.0 M in tetrahydrofuran, 118 μl) was added to a solution, of methyl 3-[[[[4'-[2-[(tert-butoxycarbonyl)[(2R)-2-hydroxy-2-phenylethyl]amino]ethyl]-3-(cyclohexyloxy)-4-biphenylyl]carbonyl]amino]sulfonyl]propanoate (50.0 mg) in tetrahydrofuran (1.0 ml) at −78° C., and the mixture was stirred at 0° C. for 10 minutes. The mixture was poured into sat. ammonium chloride aq. solution and the products were extracted with ethyl acetate. The combined extracts were washed with brine, dried over magnesium sulfate, and evaporated in vacuo. The residue was purified by silica gel column chromatography to give tert-butyl [2-[3'-(cyclohexyloxy)-4'-[[[(3-hydroxy-3-methylbutyl)sulfonyl]-amino]carbonyl]-4-biphenylyl]ethyl][(2R)-2-hydroxy-2-phenylethyl]carbamate (33.8 mg).

(−)ESI-MS (m/z): 707 (M−H)−

EXAMPLE 34

Sodium methoxide (38.1 mg) was added to a solution of methyl 3-[[[[4'-[2-[(tert-butoxycarbonyl)[(2R)-2-hydroxy-2-phenylethyl]amino]ethyl]-3-(cyclohexyloxy)-4-biphenylyl]carbonyl]amino]sulfonyl]propanoate (125 mg) in formamide (2.0 ml) at room temperature. The mixture was stirred for 1.5 hours at 60° C. The product was extracted with ethyl acetate. The combined extracts were washed with brine, dried over magnesium sulfate and evaporated in vacuo. The residue was purified by silica gel column chromatography to give tert-butyl [2-[4'-[[[(3-amino-3-oxopropyl)sulfonyl]amino]carbonyl]-3'-(cyclohexyloxy)-4-biphenylyl]ethyl][(2R)-2-hydroxy-2-phenylethyl]carbamate (22.0 mg).

(+)ESI-MS (m/z): 694 (M+H)+

EXAMPLE 35

1N Sodium hydroxide (575 μl) was added to a solution of 4-[[[[4'-[2-[(tert-butoxycarbonyl)[(2R)-2-hydroxy-2-phenylethyl]amino]ethyl]-3-(cyclohexyloxy)-4-biphenylyl]-carbonyl]amino]sulfonyl]butyl acetate (212 mg) in methanol (4.24 ml). The mixture was stirred at room temperature overnight. The mixture was evaporated in vacuo. The residue was purified by silica gel column chromatography to give tert-butyl [2-[3'-(cyclohexyloxy)-4'-[[[(4-hydroxybutyl)sulfonyl]amino]carbonyl]-4-biphenylyl]ethyl]-[(2R)-2-hydroxy-2-phenylethyl]carbamate (111 mg).

(−)ESI-MS (m/z): 695 (M+H)+

PREPARATION 27

A mixture of 3-pyridinesulfonic acid (10.0 g), phosphorous pentachloride (13.1 g) and phosphoryl chloride (10.0 ml) was stirred at 130° C. for 3.5 hours. The solution was evaporated and diluted with acetone. The solution was evaporated and poured into water (200 ml) and isopropyl ether (400 ml). The organic layer was separated, washed with brine twice, saturated sodium bicarbonate aqueous solution and brine and dried over magnesium sulfate. The solution was evaporated, covered with hexane (20 ml) and added hydrogen chloride in ethyl acetate (4N, 20 ml) dropwise with stirring. The resulting solid was collected by filtration and dried to give 3-pyridinesulfonyl chloride hydrochloride (9.49 g).

NMR (200 MHz, DMSO-$d_6$, δ): 8.12 (1H, dd, J=5, 8 Hz), 8.72 (1H, dd, J=1.8, 3 Hz), 8.95 (1H, d, J=5.5 Hz), 8.99 (1H, d, J=1 Hz), 14.25 (1H, br s)

PREPARATION 28

To a suspension of 3-pyridinesulfonyl chloride hydrochloride (5.00 g) in acetone (8.5 ml) was added ammonia aqueous solution (28%, 8.5 ml) at 0° C. dropwise and stirred at room temperature for 3 hours. The solution was evaporated and poured into water (ca. 10 ml), ethyl acetate (100 ml) and tetrahydrofuran (100 ml). The organic layer was washed with brine twice and the aqueous layer was extracted with ethyl acetate (90 ml) and methanol (10 ml). The combined organic layer was dried over magnesium sulfate, evaporated and crystallized in hexane and ethyl acetate to give 3-pyridinesulfonamide (3.45 g).

(+)ESI-MS (m/z): 159 (M+H)⁺

PREPARATION 29

To a suspension of sodium sulfite (41.7 g) in water (40 ml) was added chloroacetonitrile (20.8 ml) and stirred at room temperature for 4 hours. The mixture was evaporated and diluted with methanol. The mixture was diluted with methanol and toluene, evaporated and crystallized from ethanol. The resulting solid was dried at 60° C. to give sodium cyanomethanesulfonate (53.5 g).

(−)ESI-MS (m/z): 120 (M−Na)⁻

PREPARATION 30

A mixture of sodium cyanomethanesulfonate (15.0 g), phosphorous pentachloride (21.8 g) and phosphoryl chloride (27.0 ml) was stirred at 70° C. under nitrogen for 3 hours. The solid was filtered off, and the solution was evaporated to give cyanomethanesulfonyl chloride (8.66 g) as crude oil. This compound was used for next reaction without further purification.

PREPARATION 31

A solution of crude cyanomethanesulfonyl chloride (8.66 g) in dichloromethane (52.0 ml) and tetrahydrofuran (13.0 ml) was bubbled with ammonia gas below 10° C. for 1 hour with stirring. The brown solid was collected by filtration, and eluted with methanol. The solution was evaporated and the residue was purified with silica gel column chromatography to give 1-cyanomethanesulfonamide (1.36 g).

(−)ESI-MS (m/z): 119 (M−H)⁻

PREPARATION 32

To a solution of 4'-[2-[(tert-butoxycarbonyl)[(2R)-2-phenyl-2-(tetrahydro-2H-pyran-2-yloxy)ethyl]amino]ethyl]-3-(isopropylthio)-4-biphenylcarboxylic acid (500 mg) in N,N-dimethylformamide (5 ml) was added N,N'-carbonyldiimidazole (157 mg) and stirred at room temperature for 30 minutes. To the mixture were added 3-pyridinesulfonamide (153 mg) and 1,8-diazabicyclo[5.4.0]-7-undecene (145 μl) and stirred at room temperature for 3 hours. The reaction mixture was poured into 0.1N hydrochloric acid and ethyl acetate and the organic layer was separated. The organic layer was washed with water and brine, dried over magnesium sulfate and concentrated in vacuo. The residue was purified with silica gel column chromatography to give tert-butyl [2-[3'-(isopropylthio)-4'-[[(3-pyridylsulfonyl)amino]carbonyl]-4-biphenylyl]-ethyl][(2R)-2-phenyl-2-(tetrahydro-2H-pyran-2-yloxy)ethyl]carbamate (613 mg).

(−)ESI-MS (m/z): 758 (M−H)⁻

The following compounds from Preparation 33 to Preparation 35 were obtained according to a similar manner to that of Preparation 32.

PREPARATION 33 tert-Butyl [2-[4'-[[[(cyanomethyl)sulfonyl]amino]-carbonyl]-3'-(isopropylthio)-4-biphenylyl]ethyl][(2R)-2-phenyl-2-(tetrahydro-2H-pyran-2-yloxy)ethyl]carbamate (−)ESI-MS (m/z): 720 (M−H)⁻

PREPARATION 34 tert-Butyl [(2R)-2-[[tert-butyl(dimethyl)silyl]oxy]-2-(3-pyridyl)ethyl][2-[3'-(cyclohexyloxy)-4'-[[(3-pyridylsulfonyl)amino]carbonyl]-4-biphenylyl]ethyl]-carbamate (−)ESI-MS (m/z): 813 (M−H)⁻

PREPARATION 35 tert-Butyl [(2R)-2-[[tert-butyl(dimethyl)silyl]oxy]-2-(3-pyridyl)ethyl][2-[4'-[[[(cyanomethyl)sulfonyl]amino]-carbonyl]-3'-(cyclohexyloxy)-4-biphenylyl]ethyl]carbamate (−)ESI-MS (m/z): 776 (M−H)⁻

PREPARATION 36

To a solution of tert-butyl [(2R)-2-(3-chlorophenyl)-2-hydroxyethyl][2-[(4-iodophenyl)amino]ethyl]carbamate (200 mg), [3-(cyclohexyloxy)-4-(methoxycarbonyl)phenyl]-boronic acid (193 mg), potassium phosphate (246 mg) in ethanol (1.5 ml) was added bis(dicyclohexylamine)-palladium (II) acetate (32.9 mg) and the mixture was stirred at 60° C. for 3 hours under nitrogen atmosphere. After warming to 80° C., the mixture was stirred at the same temperature for 3 hours. To the reaction mixture were added [3-(cyclohexyloxy)-4-(methoxycarbonyl)phenyl]boronic acid (107 mg) and bis(dicyclohexylamine)palladium(II) acetate (10.9 mg) and the mixture was stirred at 80° C. for 3 hours. After cooling to room temperature, the reaction mixture was diluted with ethyl acetate and filtered through the celite cake. The filtrate was washed with water and brine and dried over magnesium sulfate. Filtration followed by evaporation under reduced pressure gave the crude product which was purified by column chromatography on silica gel (eluent: hexane/ethyl acetate=1/6 to 1/2) to give methyl 4'-[[2-[(tert-butoxycarbonyl)[(2R)-2-(3-chlorophenyl)-2-hydroxyethyl]amino]-ethyl]amino]-3-(cyclohexyloxy)-4-biphenylcarboxylate (130 mg) as a white solid.

(+)ESI-MS (m/z): 623 (M+H)⁺, 646 (M+Na)⁺

PREPARATION 37

To a solution of methyl 4'-[[2-[(tert-butoxycarbonyl)-[(2R)-2-(3-chlorophenyl)-2-hydroxyethyl]amino]-ethyl]amino]-3-(cyclohexyloxy)-4-biphenylcarboxylate (125 mg) in methanol (1.750 ml) and tetrahydrofuran (0.900 ml) was added 1N aqueous sodium hydroxide solution (1.05 ml) and the mixture was stirred at room temperature for 1 day. To the reaction mixture was added 1N aqueous sodium hydroxide solution (0.900 ml) and the mixture was stirred at room temperature for 3 days. The reaction mixture was concentrated under reduced pressure and to the residue were added ethyl acetate (40 ml) and water (20 ml). The pH value was adjusted to 5.70 by addition of 0.1N hydrochloric acid and the separated organic layer was washed with water and brine and dried over magnesium sulfate. Filtration followed by evaporation gave 4'-[[2-[(tert-butoxycarbonyl)[(2R)-2-(3-chlorophenyl)-2-hydroxyethyl]amino]ethyl]amino]-3-(cyclohexyloxy)-4-biphenylcarboxylic acid (123 mg) as a yellow foam.

(−)ESI-MS (m/z): 607 (M−H)⁻

PREPARATION 38

To a solution of methyl 4'-[[2-[(tert-butoxycarbonyl)-[(2R)-2-(3-chlorophenyl)-2-hydroxyethyl]amino]-ethyl]

amino]-3-(cyclohexyloxy)-4-biphenylcarboxylate (125 mg) in methanol (1.750 ml) and tetrahydrofuran (0.900 ml) was added 1N aqueous sodium hydroxide solution (1.05 ml) and the mixture was stirred at room temperature for 1 day. To the reaction mixture was added 1N aqueous sodium hydroxide solution (0.900 ml) and the mixture was stirred at room temperature for 3 days. The reaction mixture was concentrated under reduced pressure and to the residue were added ethyl acetate (40 ml) and water (20 ml). The pH value was adjusted to 5.70 by addition of 0.1N hydrochloric acid and the separated organic layer was washed with water and brine and dried over magnesium sulfate. Filtration followed by evaporation gave 4'-[[2-[(tert-butoxycarbonyl)[(2R)-2-(3-chlorophenyl)-2-hydroxyethyl]amino]ethyl]amino]-3-(cyclohexyloxy)-4-biphenylcarboxylic acid (123 mg) as a yellow foam.

(+)ESI-MS (m/z): 597 (M+H)$^+$, 620 (M+Na)$^+$

PREPARATION 39

The following compound was obtained according to a similar manner to that of Preparation 37.

4'-[[2-[(tert-Butoxycarbonyl)[(2R)-2-(3-chlorophenyl)-2-hydroxyethyl]amino]ethyl]amino]-3-isobutoxy-4-biphenylcarboxylic acid (−)ESI-MS (m/z): 582 (M−H)$^-$

PREPARATION 40

To a solution of 6-bromo-1-isopropyl-1H-indole-3-carboxylic acid (1.94 g) in N,N-dimethylformamide (97 ml) were added potassium carbonate (1.43 g) and iodomethane (0.514 ml) at room temperature under nitrogen, and the mixture was stirred at the same temperature for 3.5 hours. The resulting mixture was poured into water and the aqueous layer was extracted with ethyl acetate. The organic layer was washed successively with water three times and brine, dried over anhydrous magnesium sulfate and evaporated under reduced pressure. The residue was purified by column chromatography on silica gel (hexane/ethyl acetate=10/1 to 5/1) to give methyl 6-bromo-1-isopropyl-1H-indole-3-carboxylate (1.9 g).

(+)ESI-MS (m/z): 318, 320 (M+Na)$^+$

PREPARATION 41

To a solution of methyl 6-bromo-2-naphthoate (5.0 g) in 1,4-dioxane (50 ml) were added 4,4,4',4',5,5,5',5'-octamethyl-2,2'-bi-1,3,2-dioxaborolane (5.3 g), dichlorobis(triphenylphosphine)palladium(II) (1.3 g) and potassium acetate (4.6 g) at room temperature under nitrogen, and the mixture was stirred at 90° C. for 2 hours. The resulting mixture was poured into water and the aqueous layer was extracted with ethyl acetate. The organic layer was washed with brine, dried over anhydrous magnesium sulfate, and evaporated under reduced pressure. The residue was purified by column chromatography on silica gel (eluent: chloroform) to give methyl 6-(4,4,5,5-tetramethyl-1,3,2-dioxaborolan-2-yl)-2-naphthoate (3.6 g).

(+)ESI-MS (m/z): 313 (M+H)$^+$

PREPARATION 42

The following compound was obtained according to a similar manner to that of Preparation 41.

Methyl 1-isopropyl-6-(4,4,5,5-tetramethyl-1,3,2-dioxaborolan-2-yl)-1H-indole-3-carboxylate (+)ESI-MS (m/z): 366 (M+Na)$^+$

PREPARATION 43

To a solution of tert-butyl [2-(4-bromophenyl)ethyl]-[(2R)-2-(3-chlorophenyl)-2-hydroxyethyl]carbamate (560 mg) and methyl 6-(4,4,5,5-tetramethyl-1,3,2-dioxaborolan-2-yl)-2-naphthoate (461 mg) in N,N-dimethylformamide (5.6 ml) were added [1',1'-bis(diphenylphosphino)ferrocene]-palladium(II) dichloride dichloromethane complex (151 mg), 1,1'-bis(diphenylphosphino)ferrocene (102 mg) and 2M sodium carbonate (2.0 ml) at room temperature, and the mixture was stirred at 80° C. for 4 hours. The resulting mixture was poured into water and the aqueous layer was extracted with ethyl acetate. The organic layer was washed successively with water three times and brine, dried over anhydrous magnesium sulfate, and evaporated under reduced pressure. The residue was purified by column chromatography on silica gel (hexane/ethyl acetate=2/1) to give methyl 6-[4-[2-[(tert-butoxycarbonyl)[(2R)-2-(3-chlorophenyl)-2-hydroxyethyl]amino]ethyl]phenyl]-2-naphthoate (514 mg).

(+)ESI-MS (m/z): 582, 584 (M+H)$^+$

PREPARATION 44

The following compound was obtained according to a similar manner to that of Preparation 43.

Methyl 6-[4-[2-[(tert-butoxycarbonyl)[(2R)-2-(3-chlorophenyl)-2-hydroxyethyl]amino]ethyl]phenyl]-1-isopropyl-1H-indole-3-carboxylate (+)ESI-MS (m/z): 613, 615 (M+Na)$^+$

PREPARATION 45

To a solution of methyl 6-[4-[2-[(tert-butoxycarbonyl) [(2R)-2-(3-chlorophenyl)-2-hydroxyethyl]amino]-ethyl] phenyl]-1-isopropyl-1H-indole-3-carboxylate (340 mg) in dichloromethane (5 ml) were added 3,4-dihydro-2H-pyran (0.105 ml) and a catalytic amount of pyridinium p-toluenesulfonate at room temperature under nitrogen, and the mixture was stirred at the same temperature for 12 hours. The resulting mixture was poured into water and the aqueous layer was extracted with ethyl acetate. The organic layer was washed successively with saturated aqueous sodium bicarbonate and brine, dried over anhydrous magnesium sulfate and evaporated under reduced pressure. The residue was purified by column chromatography on silica gel (hexane/ethyl acetate=4/1) to give methyl 6-[4-[2-[(tert-butoxycarbonyl) [(2R)-2-(3-chlorophenyl)-2-(tetrahydro-2H-pyran-2-yloxy) ethyl]amino]ethyl]phenyl]-1-isopropyl-1H-indole-3-carboxylate (310 mg).

(+)ESI-MS (m/z): 697 (M+Na)$^+$

PREPARATION 46

A mixture of methyl 6-[4-[2-[(tert-butoxycarbonyl)-[(2R)-2-(3-chlorophenyl)-2-hydroxyethyl]amino]ethyl]-phenyl]-2-naphthoate (105 mg) and 1N sodium hydroxide (0.375 ml) in 1,4-dioxane (1 ml) was stirred at room temperature for 12 hours. To the resulting mixture were added 1N hydrochloric acid (0.375 ml) and chloroform-methanol (5:1). After separation, the organic layer was dried over anhydrous magnesium sulfate, evaporated under reduced pressure. The residue was purified by column chromatography on silica gel (chlorofom/methanol=10/1) to give 6-[4-[2-[(tert-butoxycarbonyl)[(2R)-2-(3-chlorophenyl)-2-hydroxyethyl]amino]ethyl] phenyl]-2-naphthoic acid (100 mg).

(−)ESI-MS (m/z): 544, 546 (M−H)$^-$

PREPARATION 47

The following compound was obtained according to a similar manner to that of Preparation 46.

6-[4-[2-[(tert-Butoxycarbonyl)[(2R)-2-(3-chlorophenyl)-2-(tetrahydro-2H-pyran-2-yloxy)ethyl]amino]-ethyl]phenyl]-1-isopropyl-1H-indole-3-carboxylic acid (−)ESI-MS (m/z): 659, 661 (M−H)⁻

PREPARATION 48

To a solution of 6-[4-[2-[(tert-butoxycarbonyl)[(2R)-2-(3-chlorophenyl)-2-(tetrahydro-2H-pyran-2-yloxy)ethyl]-amino]ethyl]phenyl]-1-isopropyl-1H-indole-3-carboxylic acid (131 mg) in N,N-dimethylformamide (2 mL) was added 1,1'-carbonyldiimidazole (35 mg) at room temperature under nitrogen, and the mixture was stirred at the same temperature for 2.5 hours. To this one were added methanesulfonamide (46 mg) and 1,8-diazabicyclo[5.4.0]-7-undecene (72 mg) at room temperature, and the mixture was stirred at 60° C. for 10 hours. The resulting mixture was poured into 0.1N hydrochloric acid and the aqueous layer was extracted with ethyl acetate. The organic layer was washed successively with 0.1N hydrochloric acid three times and brine, dried over anhydrous magnesium sulfate and evaporated under reduced pressure. The residue was purified by column chromatography on silica gel (chloroform/methanol=200/1 to 100/1) to give tert-butyl [(2R)-2-(3-chlorophenyl)-2-(tetrahydro-2H-pyran-2-yloxy)ethyl][2-[4-[1-isopropyl-3-[[(methylsulfonyl)amino]-carbonyl]-1H-indol-6-yl]phenyl]ethyl]carbamate (134 mg).

(−)ESI-MS m/z: 736, 738 (M−H)⁻

PREPARATION 49

The following compound was obtained according to a similar manner to that of Preparation 48.

3-[[[[6-[4-[2-[(tert-Butoxycarbonyl)[(2R)-2-(3-chlorophenyl)-2-(tetrahydro-2H-pyran-2-yloxy)ethyl]amino]-ethyl]phenyl]-1-isopropyl-1H-indol-3-yl]carbonyl]amino]-sulfonyl]propyl acetate (+)ESI-MS (m/z): 846 (M+Na)⁺

PREPARATION 50

The following compound was obtained according to a similar manner to that of Preparation 38.

Methyl 4'-[2-[(tert-butoxycarbonyl)[(2R)-2-hydroxy-2-(3-pyridyl)ethyl]amino]ethyl]-3-(cyclohexyloxy)-4-biphenylcarboxylate NMR (200 MHz, DMSO-d₆, δ): 1.17-1.98 (10H, m), 1.27 (9H, s), 2.65-2.81 (2H, m), 3.10-3.55 (4H, m), 3.79 (3H, s), 4.60-4.85 (2H, m), 5.61-5.68 (1H, m), 7.22-7.72 (9H, m), 8.44-8.49 (2H, m)

(+)ESI-MS (m/z): 575 (M+H)⁺

PREPARATION 51

To a solution of methyl 4'-[2-[(tert-butoxycarbonyl)-[(2R)-2-hydroxy-2-(3-pyridyl)ethyl]amino]ethyl]-3-(cyclohexyloxy)-4-biphenylcarboxylate in N,N-dimethylformamide were added imidazole and tert-butyldimethylchlorosilane at room temperature. After stirring at room temperature for 15 minutes and at 35° C. for 3.5 hours. The reaction mixture was poured into 0.05N hydrochloric acid at room temperature. The products were extracted with ethyl acetate. The combined extracts were washed with water and brine, dried over magnesium sulfate, and evaporated. The residue was purified by silica gel column chromatography to give methyl 4'-[2-[(tert-butoxycarbonyl)[(2R)-2-[[tert-butyl(dimethyl)silyl]oxy]-2-(3-pyridyl)ethyl]amino]ethyl]-3-(cyclohexyloxy)-4-biphenylcarboxylate (11.22 g).

NMR (200 MHz, DMSO-d₆, δ): −0.15 (3H, s), 0.00 (3H, s), 0.81 (9H, s), 1.31-1.38 (9H, s), 1.20-1.30 (10H, m), 2.73-2.80 (2H, m), 3.25-3.43 (4H, m), 3.38 (3H, s), 4.50-4.80 (1H, m), 4.85-5.11 (1H, m), 7.20-7.71 (9H, m), 8.47-8.52 (2H, m)

(+)ESI-MS (m/z): 689 (M+H)⁺

PREPARATION 52

The following compound was obtained according to a similar manner to that of Preparation 37.

4'-[2-[(tert-Butoxycarbonyl)[(2R)-2-[[tert-butyl(dimethyl)silyl]oxy]-2-(3-pyridyl)ethyl]amino]ethyl]-3-(cyclohexyloxy)-4-biphenylcarboxylic acid NMR (200 MHz, DMSO-d₆, δ): −0.14 (3H, s), 0.01 (3H, s), 0.82 (9H, s), 1.32-1.39 (9H, m), 1.21-1.99 (10H, m), 2.48-2.77 (2H, m), 3.25-3.43 (4H, m), 4.58-1.65 (1H, m), 4.90-5.20 (1H, m), 7.20-7.41 (5H, m), 7.58-7.78 (4H, m), 8.47-8.52 (2H, m)

(+)ESI-MS (m/z): 675 (M+H)⁺

PREPARATION 53

The following compound was obtained according to a similar manner to that of Example 40.

Methyl 3-[[[[4'-[2-[(tert-butoxycarbonyl)[(2R)-2-[[tert-butyl(dimethyl)silyl]oxy]-2-(3-pyridyl)ethyl]-amino]ethyl]-3-(cyclohexyloxy)-4-biphenylyl]carbonyl]-amino]sulfonyl]propanoate NMR (200 MHz, DMSO-d₆, δ): −0.14 (3H, s), 0.00 (3H, s), 0.82 (9H, s), 1.28-1.32 (9H, m), 1.16-1.88 (10H, m), 1.90-2.00 (2H, m), 2.77-2.87 (3H, m), 2.55-3.50 (3H, m), 3.78 (2H, t, J=7.3 Hz), 3.33 (3H, s), 4.74-4.80 (1H, m), 4.90-5.04 (1H, m), 7.26-7.42 (5H, m), 7.60-7.72 (4H, m), 8.49-7.82 (2H, m), 11.30 (1H, s)

(−)ESI-MS (m/z): 822 (M−H)⁻

PREPARATION 54

The following compound was obtained according to a similar manner to that of Preparation 37.

3-[[[[4'-[2-[(tert-Butoxycarbonyl)[(2R)-2-[[tert-butyl(dimethyl)silyl]oxy]-2-(3-pyridyl)ethyl]amino]-ethyl]-3-(cyclohexyloxy)-4-biphenylyl]carbonyl]-amino]sulfonyl] propionic acid NMR (200 MHz, DMSO-d₆, δ): −0.13 (3H, s), 0.00 (3H, s), 0.82 (9H, s), 0.82-1.13 (9H, m), 1.13-1.80 (10H, m), 1.91-1.99 (2H, m), 2.70-2.78 (4H, m), 3.25-3.34 (2H, m), 3.74-3.78 (2H, m), 4.75-4.78 (1H, m), 4.90-5.02 (1H, m), 7.25-7.42 (5H, m), 7.64-7.76 (4H, m), 8.49-8.52 (2H, m)

(−)ESI-MS (m/z): 808 (M−H)⁻

PREPARATION 55

The following compound was obtained according to a similar manner to that of Example 33.

tert-Butyl [(2R)-2-[[tert-butyl(dimethyl)silyl]oxy]-2-(3-pyridyl)ethyl][2-[3'-(cyclohexyloxy)-4'-[[[(3-hydroxy-3-methylbutyl)sulfonyl]amino]carbonyl]-4-biphenylyl]ethyl] carbamate NMR (200 MHz, DMSO-d₆, δ): −0.14 (3H, s), 0.00 (3H, s), 0.82 (9H, s), 1.11 (6H, s), 1.71-1.21 (9H, m), 1.20-1.8 (10H, m), 1.95-2.05 (2H, m), 2.70-2.9 (2H, m), 3.23-3.60 (6H, m), 4.54 (1H, s), 4.76-4.82 (1H, m), 4.95-5.38 (1H, m), 7.26-7.42 (5H, m), 7.64-7.73 (4H, m), 8.49-8.52 (2H, m), 11.10 (1H, s)
(+)ESI-MS (m/z): 825 (M+H)⁺

PREPARATION 56

To a solution of tert-butyl [(2R)-2-[[tert-butyl(dimethyl)silyl]oxy]-2-(3-pyridyl)ethyl][2-[4'-[[[(cyanomethyl)sulfonyl]amino]carbonyl]-3'-(cyclohexyloxy)-4-biphenylyl]ethyl]carbamate (52.9 mg) in dimethyl sulfoxide (1.0 ml) was added potassium carbonate (28.3 mg), 30% aq. hydrogen peroxide solution (100 μl) at 0° C. After stirring for 16 hours at room temperature, 1N hydrochloric acid was added to the reaction mixture. The products were extracted with ethyl acetate. The combined extracts were washed with brine, dried over magnesium sulfate, and evaporated. The residue was purified by preparative thin-layer chromatography (chloroform/methanol=95/5) to give tert-butyl [2-[4'-[[[(2-amino-2-oxoethyl)sulfonyl]amino]-carbonyl]-3'-(cyclohexyloxy)-4-biphenylyl]ethyl][(2R)-2-[[tert-butyl(dimethyl)silyl]oxy]-2-(3-pyridyl)ethyl]-carbamate (30.0 mg).
(−)ESI-MS (m/z): 793 (M−H)⁻

PREPARATION 57

The following compound was obtained according to a similar manner to that of Example 40.
4-[[[[4'-[2-[(tert-Butoxycarbonyl)[(2R)-2-[[tert-butyl(dimethyl)silyl]oxy]-2-(3-pyridyl)ethyl]amino]ethyl]-3-(cyclohexyloxy)-4-biphenylyl]carbonyl]amino]sulfonyl]-butyl acetate
NMR (200 MHz, DMSO-d₆, δ): −0.15 (3H, s), 0.00 (3H, s), 0.82 (9H, s), 1.28-1.32 (9H, m), 1.26-2.00 (14H, m), 1.97 (3H, s), 2.75-2.79 (2H, m), 3.24-3.56 (6H, m), 3.98-4.04 (2H, m), 4.76-4.80 (1H, m), 4.94-5.04 (1H, m), 7.26-7.41 (5H, m), 7.63-7.72 (4H, m), 8.49-8.52 (2H, m), 11.18 (1H, s)
(−)ESI-MS (m/z): 850 (M−2H)⁻

PREPARATION 58

The following compound was obtained according to a similar manner to that of Example 35.
tert-Butyl [(2R)-2-[[tert-butyl(dimethyl)silyl]oxy]-2-(3-pyridyl)ethyl][2-[3'-(cyclohexyloxy)-4'-[[[(4-hydroxybutyl)sulfonyl]amino]carbonyl]-4-biphenylyl]-ethyl]carbamate
NMR (200 MHz, DMSO-d₆, δ): −0.15 (3H, s), 0.00 (3H, s), 0.82 (9H, s), 1.23-1.28 (9H, m), 1.22-2.10 (14H, m), 2.73-2.80 (2H, m), 3.20-3.58 (8H, m), 4.49 (1H, t, J=5 Hz), 4.76-4.80 (1H, m), 4.95-5.05 (1H, m), 7.25-7.41 (5H, m), 7.62-7.72 (4H, m), 8.49-8.52 (2H, m), 11.10 (H, s)
(−)ESI-MS (m/z): 809 (M−H)⁻

PREPARATION 59

The following compound was obtained according to a similar manner to that of Preparation 38.
Methyl 4'-[2-[(tert-butoxycarbonyl)[(2R)-2-(3-chlorophenyl)-2-hydroxyethyl]amino]ethyl]-3-(cyclohexyloxy)-4-biphenylcarboxylate
NMR (200 MHz, DMSO-d₆, δ): 1.43 (9H, s), 1.20-2.00 (10H, m), 2.64-2.98 (2H, m), 3.02-3.65 (4H, m), 3.83 (3H, s), 4.38-4.48 (1H, m), 4.84-4.91 (1H, m), 7.12-7.52 (10H, m), 7.84 (1H, d, J=8.5 Hz)
(+)ESI-MS (m/z): 631 (M+Na)⁺

PREPARATION 60

The following compound was obtained according to a similar manner to that of Preparation 51.

Methyl 4'-[2-[(tert-butoxycarbonyl)[(2R)-2-[[tert-butyl(dimethyl)silyl]oxy]-2-(3-chlorophenyl)ethyl]amino]-ethyl]-3-(cyclohexyloxy)-4-biphenylcarboxylate
NMR (200 MHz, DMSO-d₆, δ): −0.11 (3H, s), 0.10 (3H, s), 0.87-0.90 (9H, m), 1.39-1.45 (9H, m), 1.35-2.00 (10H, m), 2.72-3.89 (6H, m), 3.89 (3H, s), 4.40-4.43 (1H, m), 5.03-5.07 (1H, m), 7.12-7.38 (8H, m), 7.46-7.50 (2H, m), 7.84 (1H, d, J=8.5 Hz)
(+)ESI-MS (m/z): 744 (M+Na)⁺

PREPARATION 61

The following compound was obtained according to a similar manner to that of Preparation 37.
4'-[2-[(tert-Butoxycarbonyl)[(2R)-2-[[tert-butyl(dimethyl)silyl]oxy]-2-(3-chlorophenyl)ethyl]amino]-ethyl]-3-(cyclohexyloxy)-4-biphenylcarboxylic acid
NMR (200 MHz, DMSO-d₆, δ): −0.13 (3H, s), 0.00 (3H, s), 0.83 (9H, s), 1.30-1.34 (9H, m), 1.21-1.99 (10H, m), 2.52-2.80 (2H, m), 3.20-3.49 (4H, m), 4.59-4.65 (1H, m), 4.87-4.99 (1H, m), 7.21-7.70 (11H, m)
(−)ESI-MS (m/z): 706 (M−H)⁻

PREPARATION 62

The following compound was obtained according to a similar manner to that of Example 40.
tert-Butyl [(2R)-2-[[tert-butyl(dimethyl)silyl]oxy]-2-(3-chlorophenyl)ethyl][2-[4'-[[[(cyanomethyl)sulfonyl]-amino]carbonyl]-3'-(cyclohexyloxy)-4-biphenylyl]ethyl]-carbamate
NMR (200 MHz, DMSO-d₆, δ): −0.14 (3H, s), 0.00 (3H, s), 0.83 (9H, s), 1.29-1.34 (9H, m), 1.20-2.00 (10H, m), 2.72-2.81 (2H, m), 3.20-0.48 (4H, m), 4.70-4.76 (1H, m), 4.88-4.99 (1H, m), 5.24 (2H, s), 7.25-7.43 (8H, m), 7.63-7.68 (3H, m)
(−)ESI-MS (m/z): 808 (M−H)⁻

PREPARATION 63

The following compound was obtained according to a similar manner to that of Preparation 56.
tert-Butyl [2-[4'-[[[(2-amino-2-oxoethyl)sulfonyl]-amino]carbonyl]-3'-(cyclohexyloxy)-4-biphenylyl]ethyl]-[(2R)-2-[[tert-butyl(dimethyl)silyl]oxy]-2-(3-chlorophenyl)ethyl]carbamate
NMR (200 MHz, DMSO-d₆, δ): −0.13 (3H, s), 0.00 (3H, s), 0.83 (9H, s), 1.29-1.33 (9H, m), 1.20-2.00 (10H, m), 2.52-2.81 (2H, m), 3.20-3.48 (4H, m), 4.35 (2H, s), 4.81-4.99 (2H, m), 7.25-7.84 (11H, m), 11.20 (1H, s)
(−)ESI-MS (m/z): 826 (M−H)⁻

PREPARATION 64

A mixture of tert-butyl [(2R)-2-(3-chlorophenyl)-2-(tetrahydro-2H-pyran-2-yloxy)ethyl][2-[4-[1-isopropyl-3-[[(methylsulfonyl)amino]carbonyl]-1H-indol-6-yl]phenyl]-ethyl]carbamate (132 mg), 10% hydrogen chloride in methanol (2 ml) and 4N hydrogen chloride in 1,4-dioxane (2 ml) was stirred at room temperature for 12 hours. The resulting mixture was evaporated under reduced pressure. The residue was purified by reverse phase column chromatography followed by treatment of 1N hydrochloric acid to give 6-[4-[2-[[(2R)-2-(3-chlorophenyl)-2-hydroxyethyl]amino]ethyl]phenyl]-1-isopropyl-N-(methylsulfonyl)-1H-indole-3-carboxamide hydrochloride (81 mg).

NMR (200 MHz, DMSO-d$_6$, δ): 1.52 (6H, d, J=6.5 Hz), 3.00-3.45 (6H, m), 3.39 (3H, s), 4.90-5.10 (2H, m), 7.30-7.60 (7H, m), 7.76 (2H, d, J=8.2 Hz), 7.91 (1H, s), 8.19 (1H, d, J=8.3 Hz), 8.65 (1H, s)

(-)ESI-MS (m/z): 552 (M-HCl-H)$^-$

PREPARATION 65

The following compound was obtained according to a similar manner to that of Preparation 43.

Methyl 4'-[2-[(tert-butoxycarbonyl)[(2R)-2-phenyl-2-(tetrahydro-2H-pyran-2-yloxy)ethyl]amino]ethyl]-3-(isopropylthio)-4-biphenylcarboxylate (+)ESI-MS (m/z): 656 (M+Na)$^+$

PREPARATION 66

The following compound was obtained according to a similar manner to that of Example 2.

Methyl 4'-[2-[(tert-butoxycarbonyl)amino]ethyl]-3-(cyclohexyloxy)-4-biphenylcarboxylate (+)ESI-MS (m/z): 454 (M+H)$^+$

PREPARATION 67

The following compound was obtained according to a similar manner to that of Preparation 3.

4'-[2-[(tert-Butoxycarbonyl)[(2R)-2-phenyl-2-(tetrahydro-2H-pyran-2-yloxy)ethyl]amino]ethyl]-3-(isopropylthio)-4-biphenylcarboxylic acid (-)ESI-MS (m/z): 618 (M-H)$^-$

PREPARATION 68

To a solution of methyl 4'-[2-[(tert-butoxycarbonyl)-[(2R)-2-(6-cloro-3-pyridyl)-2-hydroxyethyl]amino]ethyl]-3-(cyclohexyloxy)-4-biphenylcarboxylate (1.43 g) in dichloromethane (25 ml) were added 3,4-dihydro-2H-pyran (0.64 ml) and pyridinium p-toluenesulfonate (118 mg) at room temperature and the mixture was stirred for 2 days under nitrogen. The mixture was diluted with ethyl acetate, washed with water and brine, dried over sodium sulfate and evaporated under reduced pressure to give residue (2.34 g). To a solution of the above residue in methanol (8 ml)/tetrahydrofuran (8 ml) was added aqueous solution of sodium hydroxide (1N, 8 ml) at room temperature and the mixture was stirred at room temperature overnight. The mixture solution was acidified with aqueous hydrochloric acid solution (1N), poured into water and extracted with ethyl acetate. The organic layer was washed with brine, dried over sodium sulfate and evaporated under reduced pressure. The residue was purified by column chromatography on silica gel (hexane/ethyl acetate=6/4) to give 4'-[2-[(tert-butoxycarbonyl)[(2R)-2-(6-chloro-3-pyridyl)-2-(tetrahydro-2H-pyran-2-yloxy)ethyl]amino]ethyl]-3-(cyclohexyloxy)-4-biphenylcarboxylic acid (1.42 g).

(-)ESI-MS (m/z): 677 (M-H)$^-$

PREPARATION 69

To a solution of 4'-[2-[(tert-butoxycarbonyl)[(2R)-2-phenyl-2-(tetrahydro-2H-pyran-2-yloxy)ethyl]amino]ethyl]-3-isopropoxy-4-biphenylcarboxylic acid (224 mg) in N,N-dimethylformamide (2 ml) was added 1,1'-carbonyldiimidazole (72 mg) at room temperature and the mixture was stirred at the same temperature for 1 hour. 1-Pentanesulfonamide (67 mg) and 1,8-diazabicyclo[5.4.0]-7-undecene (0.067 ml) were added to the mixture at room temperature. The mixture was stirred at 70° C. for 4 hours. After cooling down to room temperature, the mixture was diluted with ethyl acetate, washed with aqueous hydrochloric acid solution (0.5N) and brine, dried over sodium sulfate and evaporated under reduced pressure to give residue (403 mg). To a solution of the above residue in methanol (2 ml) was added 4-methylbenzenesulfonic acid at room temperature and the mixture was stirred at the same temperature for 2 days. The mixture was diluted with ethyl acetate, washed with water and brine, dried over sodium sulfate and evaporated under reduced pressure. The residue was purified by column chromatography on silica gel (hexane/ethyl acetate=7/3) to give tert-butyl [(2R)-2-hydroxy-2-phenylethyl]-[2-[3'-isopropoxy-4'-[[(pentylsulfonyl)amino]carbonyl]-4-biphenylyl]ethyl]carbamate (179 mg).

(+)ESI-MS (m/z): 675 (M+Na)$^+$

PREPARATION 70

The following compounds were obtained according to a similar manner to that of Preparation 69.
(1) tert-Butyl [(2R)-2-hydroxy-2-phenylethyl][2-[4'-[[[(3-hydroxypropyl)sulfonyl]amino]carbonyl]-3'-isopropoxy-4-biphenylyl]ethyl]carbamate (+)ESI-MS (m/z): 663 (M+Na)$^+$
(2) tert-Butyl [(2R)-2-hydroxy-2-phenylethyl][2-[4'-[[[(3-hydroxypropyl)sulfonyl]amino]carbonyl]-3'-(isopropylthio)-4-biphenylyl]ethyl]carbamate (+)ESI-MS (m/z): 679 (M+Na)$^+$
(3) tert-Butyl [2-[3'-(cyclohexyloxy)-4'-[[[(3-hydroxypropyl)sulfonyl]amino]carbonyl]-4-biphenylyl]-ethyl][(2R)-2-hydroxy-2-phenylethyl]carbamate (+)ESI-MS (m/z): 703 (M+Na)$^+$
(4) tert-Butyl [(2R)-2-(6-chloro-3-pyridyl)-2-hydroxyethyl][2-[3'-(cyclohexyloxy)-4'-[[[(3-hydroxypropyl)sulfonyl]amino]carbonyl]-4-biphenylyl]ethyl]carbamate (+)ESI-MS (m/z): 716 (M+H)$^+$
(5) tert-Butyl [(2R)-2-(6-chloro-3-pyridyl)-2-hydroxyethyl][2-[3'-(cyclohexyloxy)-4'-[[[(2-methoxyethyl)-sulfonyl]amino]carbonyl]-4-biphenylyl]ethyl]carbamate (+)ESI-MS (m/z): 716 (M+H)$^+$

PREPARATION 71

To a solution of methyl 4'-[2-[(tert-butoxycarbonyl)amino]ethyl]-3-(cyclohexyloxy)-4-biphenylcarboxylate (1.52 g) in 1,4-dioxane (6 ml) was added hydrochloric acid 1,4-dioxane solution (4N, 8 ml) at room temperature and the mixture was stirred overnight. The mixture was evaporated under reduced pressure. The residue was dissolved in chloroform/methanol (5/1, 80 ml). The solution was washed with aqueous sodium bicarbonate solution (80 ml) and brine, dried over sodium sulfate and evaporated under reduced pressure. A mixture of the above residue (1.18 g) and N,N'-bis(trimethylsilyl)urea (0.85 g) in dimethyl sulfoxide (6 ml) was stirred at 65° C. under nitrogen atmosphere. After 1 hour stirring, 2-chloro-5-[(2R)-2-oxiranyl]pyridine (0.65 g) was added to the mixture. The mixture was stirred at 65° C. for 40 hours. Conc. aqueous hydrochloric acid solution (0.4 ml) was added to the mixture at approximately 0° C. The mixture was stirred at room temperature for 30 minutes. Aqueous sodium bicarbonate solution (40 ml) was added into the mixture. The mixture was extracted with chloroform, dried over sodium sulfate and evaporated under reduced pressure. The mixture of the above residue (2.3 g) and di-tert-butyl dicarbonate (1.3 g) in tetrahydrofuran (5 ml) was stirred overnight. The mixture was poured into water, extracted with ethyl acetate, dried over sodium sulfate and evaporated under reduced pressure. The residue was purified by column chromatography on silica gel (hexane/ethyl acetate=5/5) to give methyl 4'-[2-[(tert-butoxycarbonyl)[(2R)-2-(6-chloro-3-pyridyl)-2-hydroxyethyl)amino]ethyl]-3-(cyclohexyloxy)-4-biphenylcarboxylate (1.44 g).

(+)ESI-MS (m/z): 609 (M+H)$^+$

PREPARATION 72

The mixture of tert-butyl [(2R)-2-(6-chloro-3-pyridyl)-2-hydroxyethyl][2-[3'-(cyclohexyloxy)-4'-[[[(3-hydroxypropyl)sulfonyl]amino]carbonyl]-4-biphenylyl]-ethyl]carbamate (145 mg), ammonium formate (128 mg) and palladium on carbon powder (50 mg) in methanol (2 ml) and water (0.2 ml) was refluxed for 50 minutes. The catalyst was filtered off and the filtrate was evaporated under reduced pressure. The residue was purified by column chromatography on silica gel (chloroform/methanol=94/6) to give tert-butyl [2-[3'-(cyclohexyloxy)-4'-[[[(3-hydroxypropyl)sulfonyl]amino]carbonyl]-4-biphenylyl]ethyl][(2R)-2-hydroxy-2-(3-pyridyl)ethyl]carbamate (117 mg).

(+)ESI-MS (m/z): 682 (M+H)$^+$

PREPARATION 73

The following compound was obtained according to a similar manner to that of Preparation 72.

tert-Butyl [2-[3'-(cyclohexyloxy)-4'-[[[(2-methoxyethyl)sulfonyl]amino]carbonyl]-4-biphenylyl]ethyl][(2R)-2-hydroxy-2-(3-pyridyl)ethyl]carbamate (+)ESI-MS (m/z): 682 (M+H)$^+$

EXAMPLE 36

A mixture of tert-butyl [2-[3'-(isopropylthio)-4'-[[(3-pyridylsulfonyl)amino]carbonyl]-4-biphenylyl]-ethyl][(2R)-2-phenyl-2-(tetrahydro-2H-pyran-2-yloxy)ethyl]carbamate (411 mg) and hydrogen chloride in methanol (10%, 8.22 ml) was stirred at room temperature overnight. The mixture was evaporated and recrystallized from ethanol to give 4'-[2-[[(2R)-2-hydroxy-2-phenylethyl]amino]ethyl]-3-(isopropylthio)-N-(3-pyridylsulfonyl)-4-biphenylcarboxamide dihydrochloride (242 mg).

NMR (200 MHz, DMSO-$d_6$, δ): 1.05 (6H, d, J=6.6 Hz), 2.89-3.33 (6H, m), 3.33-3.46 (1H, m), 5.00 (1H, dd, J=2.7, 10.3 Hz), 7.30-7.41 (7H, m), 7.54-7.64 (2H, m), 7.68-7.79 (4H, m), 8.41 (1H, dt, J=2.3, 4 Hz), 8.94 (1H, dd, J=1.5, 5 Hz), 8.93 (1H, br s), 9.15 (1H, d, J=1.5 Hz), 9.33 (1H, br s)

(−)ESI-MS (m/z): 574 (M−H)$^-$

The following compounds from Example 37 to Example 39 were obtained according to a similar manner to that of Example 36.

EXAMPLE 37

N-[(Cyanomethyl)sulfonyl]-4'-[2-[[(2R)-2-hydroxy-2-phenylethyl]amino]ethyl]-3-(isopropylthio)-4-biphenylcarboxamide hydrochloride NMR (200 MHz, DMSO-$d_6$, δ): 1.27 (6H, d, J=6.5 Hz), 3.05-3.24 (6H, m), 3.60-3.73 (1H, m), 4.86 (2H, s), 4.98 (1H, d, J=9.5 Hz), 6.22 (1H, br s), 7.31-7.42 (7H, m), 7.52 (1H, d, J=8 Hz), 7.62-7.63 (1H, m), 7.69-7.76 (3H, m), 8.85 (1H, br s), 9.06 (1H, br s)

(−)ESI-MS (m/z): 536 (M−H)$^-$

EXAMPLE 38

3-(Cyclohexyloxy)-4'-[2-[[(2R)-2-hydroxy-2-(3-pyridyl)ethyl]amino]ethyl]-N-(3-pyridylsulfonyl)-4-biphenylcarboxamide trihydrochloride NMR (200 MHz, DMSO-$d_6$, δ): 1.31-1.67 (8H, m), 1.71-1.91 (2H, m), 3.02-3.50 (6H, m), 4.61-4.78 (1H, m), 5.34 (1H, d, J=5.6 Hz), 7.29 (1H, d, J=8 Hz), 7.36-7.40 (3H, m), 7.54 (1H, d, J=8 Hz), 7.70 (2H, d, J=8 Hz), 7.74 (1H, dd, J=6.2, 10.5 Hz), 8.08 (1H, dd, J=5.5, 8 Hz), 8.41 (1H, dt, J=2.8, 3.8 Hz), 8.60 (1H, d, J=8 Hz), 8.88-8.94 (3H, m), 9.15 (1H, d, J=1.5 Hz), 9.36 (2H, br s), 12.06 (1H, br s)

(−)ESI-MS (m/z): 599 (M−H)$^-$

EXAMPLE 39

N-[(Cyanomethyl)sulfonyl]-3-(cyclohexyloxy)-4'-[2-[[(2R)-2-hydroxy-2-(3-pyridyl)ethyl]amino]ethyl]-4-biphenylcarboxamide dihydrochloride NMR (200 MHz, DMSO-$d_6$, δ): 1.32-1.85 (8H, m), 1.86-2.02 (2H, m), 3.04-3.48 (6H, m), 4.63-4.91 (1H, m), 5.20-5.32 (3H, m), 7.34-7.42 (3H, m), 7.67 (1H, d, J=8 Hz), 7.74 (2H, d, J=8 Hz), 8.00 (1H, dd, J=5.5, 8 Hz), 8.50 (1H, d, J=8.5 Hz), 8.85 (1H, d, J=5.5 Hz), 8.91 (1H, s), 9.28 (1H, br s), 9.39 (1H, br s)

(−)ESI-MS (m/z): 561 (M−H)$^-$

EXAMPLE 40

To a solution of 4'-[[2-[(tert-butoxycarbonyl)[(2R)-2-(3-chlorophenyl)-2-hydroxyethyl]amino]ethyl]amino]-3-isobutoxy-4-biphenylcarboxylic acid (60.0 mg) in N,N-dimethylformamide (0.450 ml) was added 1,1'-carbonylbis-1H-imidazole (18.3 mg) and the mixture was stirred at room temperature for 1.5 hours under nitrogen atmosphere. To the mixture were added 2,3,4,6,7,8,9,10-octahydropyrimido-[1,2-a]azepine (0.0185 ml) and a solution of 3-(aminosulfonyl)propyl acetate (22.4 mg) in N,N-dimethylformamide (0.300 ml) and the mixture was stirred at room temperature for 2 days. The reaction mixture was warmed to 120° C. and stirred at the same temperature for 2 hours. After cooling to room temperature, the reaction mixture was extracted with ethyl acetate, washed with water and brine and dried over magnesium sulfate. Filtration followed by evaporation gave the crude product which was purified by column chromatography on silica gel (eluent: hexane/ethyl acetate=1/3 to 1/1) to give 3-[[[[4'-[[2-[(tert-butoxycarbonyl)[(2R)-2-(3-chlorophenyl)-2-hydroxyethyl]amino]ethyl]amino]-3-isobutoxy-4-biphenylyl]carbonyl]amino]sulfonyl]propyl acetate (34.1 mg) as a yellow paste.

(−)ESI-MS (m/z): 744 (M−H)$^-$

EXAMPLE 41

To a solution of 3-[[[[4'-[[2-[(tert-butoxycarbonyl)-[(2R)-2-(3-chlorophenyl)-2-hydroxyethyl]amino]ethyl]amino]-3-isobutoxy-4-biphenylyl]carbonyl]amino]sulfonyl]propyl acetate (34.0 mg) in methanol (0.340 ml) and tetrahydrofuran (0.170 ml) was added 1N aqueous sodium hydroxide solution (0.228 ml) and the mixture was stirred at room temperature for 1 hour. The reaction mixture was extracted with ethyl acetate, washed with water and brine and dried over magnesium sulfate. The solvent was concentrated under reduced pressure. To a solution of the resulting residue in 1,4-dioxane (0.340 ml) was added 4N hydrogen chloride in 1,4-dioxane (0.340 ml) and the mixture was stirred at room temperature overnight. The solvent was concentrated under reduced pressure and to the residue was added ethyl acetate. The precipitate was collected by filtration and dried in vacuo to give 4'-[[2-[[(2R)-2-(3-chlorophenyl)-2-hydroxyethyl]amino]ethyl]amino]-N-[(3-hydroxypropyl)sulfonyl]-3-isobutoxy-4-biphenylcarboxamide dihydrochloride (24.8 mg) as a yellow powder.

NMR (200 MHz, DMSO-$d_6$, δ): 1.05 (6H, d, J=7 Hz), 1.79-1.93 (2H, m), 2.02-2.19 (1H, m), 2.99-3.35 (4H, m), 3.61-3.44 (6H, m), 4.01-4.06 (2H, m), 4.98-5.05 (1H, m), 6.75 (2H, d, J=8.5 Hz), 7.28-7.49 (6H, m), 7.57-7.71 (3H, m), 8.85 (1H, br s), 9.18 (1H, br s), 10.99 (1H, s)

(−)ESI-MS (m/z): 603 (M−H)⁻

EXAMPLE 42

The following compound was obtained according to a similar manner to that of Example 40.

3-[[[[4'-[[2-[(tert-Butoxycarbonyl)[(2R)-2-(3-chlorophenyl)-2-hydroxyethyl]amino]ethyl]amino]-3-(cyclohexyloxy)-4-biphenylyl]carbonyl]amino]sulfonyl]propyl acetate (−)ESI-MS (m/z): 770 (M−H)⁻

EXAMPLE 43

The following compound was obtained according to a similar manner to that of Example 41.

4'-[[2-[[(2R)-2-(3-Chlorophenyl)-2-hydroxyethyl]amino]ethyl]amino]-3-(cyclohexyloxy)-N-[(3-hydroxypropyl)sulfonyl]-4-biphenylcarboxamide dihydrochloride NMR (200 MHz, DMSO-$d_6$, δ): 1.29-1.64 (6H, m), 1.68-1.78 (2H, m), 1.82-1.91 (2H, m), 1.93-2.01 (2H, m), 3.02-3.31 (4H, m), 3.48-3.58 (6H, m), 4.80-4.86 (1H, m), 5.01-5.04 (1H, m), 6.76 (2H, d, J=8.8 Hz), 7.29-7.48 (6H, m), 7.58 (2H, d, J=8.8 Hz), 7.74 (1H, d, J=8.4 Hz), 8.87 (1H, br s), 9.24 (1H, br s), 10.97 (1H, s)

(−)ESI-MS (m/z): 628 (M−H)⁻

EXAMPLE 44

The following compound was obtained according to a similar manner to that of Preparation 64.

6-[4-[2-[[(2R)-2-(3-Chlorophenyl)-2-hydroxyethyl]amino]ethyl]phenyl]-N-[(3-hydroxypropyl)sulfonyl]-1-isopropyl-1H-indole-3-carboxamide hydrochloride NMR (200 MHz, DMSO-$d_6$, δ): 1.52 (6H, d, J=6.5 Hz), 1.75-1.95 (2H, m), 2.95-3.65 (10H, m), 4.90-5.05 (2H, m), 7.30-7.60 (7H, m), 7.76 (2H, d, J=8.2 Hz), 7.90 (1H, s), 8.18 (1H, d, J=8.4 Hz), 8.65 (1H, s)

(−)ESI-MS (m/z): 596 (M-2HCl-H)⁻

EXAMPLE 45

To 3-[[[[4'-[2-[(tert-Butoxycarbonyl)[(2R)-2-[[tert-butyl(dimethyl)silyl]oxy]-2-(3-pyridyl)ethyl]amino]ethyl]-3-(cyclohexyloxy)-4-biphenylyl]carbonyl]amino]sulfonyl]-propionic acid (49.7 mg) was added 4N hydrogen chloride in 1,4-dioxane (1.5 ml). After stirring at room temperature for 12 hours, the mixture was evaporated to give 3-[[[[3-(cyclohexyloxy)-4'-[2-[[(2R)-2-hydroxy-2-(3-pyridyl)ethyl]amino]ethyl]-4-biphenylyl]carbonyl]amino]sulfonyl]propanoic acid dihydrochloride (41.0 mg).

NMR (200 MHz, DMSO-$d_6$, δ): 1.23-1.70 (10H, m), 1.90-1.98 (2H, m), 2.71-2.79 (2H, m), 3.07-3.36 (4H, m), 3.56-3.79 (2H, m), 5.20-5.29 (1H, m), 5.70-5.76 (1H, m), 6.30 (1H, br s), 7.16-7.41 (4H, m), 7.63-7.75 (3H, m), 7.90-7.97 (1H, m), 8.41-8.46 (1H, m), 8.84 (2H, d, J=16 Hz), 9.20-9.34 (2H, m)

(−)ESI-MS (m/z): 594 (M-2HCl-H)⁻

The following compounds from Example 46 to Example 49 were obtained according to a similar manner to that of Example 45.

EXAMPLE 46

3-(Cyclohexyloxy)-N-[(3-hydroxy-3-methylbutyl)sulfonyl]-4'-[2-[[(2R)-2-hydroxy-2-(3-pyridyl)ethyl]amino]ethyl]-4-biphenylcarboxamide dihydrochloride NMR (200 MHz, DMSO-$d_6$, δ): 1.12 (6H, s), 1.12-1.92 (10H, m), 1.92-1.98 (2H, m), 3.07-3.59 (8H, m), 4.78-4.83 (1H, m), 5.20-5.28 (1H, m), 7.33-7.44 (4H, m), 7.72-7.76 (3H, m), 7.88-7.95 (1H, m), 8.30-8.42 (1H, m), 8.75-8.86 (2H, m)

(−)ESI-MS (m/z): 608 (M−H)⁻

EXAMPLE 47

N-[(2-Amino-2-oxoethyl)sulfonyl]-3-(cyclohexyloxy)-4'-[2-[[(2R)-2-hydroxy-2-(3-pyridyl)ethyl]amino]ethyl]-4-biphenylcarboxamide dihydrochloride NMR (200 MHz, DMSO-$d_6$, δ): 1.39-1.72 (10H, m), 2.99 (2H, s), 3.00-3.50 (6H, m), 4.70-4.90 (1H, m), 5.25-5.30 (1H, m), 7.23-7.44 (4H, m), 7.73-7.97 (4H, m), 8.40-8.45 (1H, m), 8.81-8.88 (2H, m), 9.24-9.40 (2H, m)

(−)ESI-MS (m/z): 579 (M−H)⁻

EXAMPLE 48

3-(Cyclohexyloxy)-N-[(4-hydroxybutyl)sulfonyl]-4'-[2-[[(2R)-2-hydroxy-2-(3-pyridyl)ethyl]amino]ethyl]-4-biphenylcarboxamide dihydrochloride NMR (200 MHz, DMSO-$d_6$, δ): 1.23-1.91 (14H, m), 3.11-3.80 (10H, m), 4.78-4.82 (1H, m), 5.23-5.27 (1H, m), 7.30-7.42 (4H, m), 7.71-7.75 (3H, m), 7.86-7.93 (1H, m), 8.34-8.39 (1H, m), 8.78-8.86 (2H, m), 9.12-9.29 (2H, m), 11.17 (1H, s)

(−)ESI-MS (m/z): 594 (M−H)⁻

EXAMPLE 49

N-[(2-Amino-2-oxoethyl)sulfonyl]-4'-[2-[[(2R)-2-(3-chlorophenyl)-2-hydroxyethyl]amino]ethyl]-3-(cyclohexyloxy)-4-biphenylcarboxamide hydrochloride NMR (200 MHz, DMSO-$d_6$, δ): 1.02-1.94 (10H, m), 3.05-3.33 (6H, m), 4.35 (2H, s), 4.81-4.83 (1H, m), 4.98-5.03 (1H, m), 6.36 (1H, d, J=2 Hz), 7.36-7.48 (7H, m), 7.73-7.84 (4H, m), 8.90-9.13 (2H, m), 11.2 (1H, br s)

(+)ESI-MS (m/z): 594 (M+H)⁺

EXAMPLE 50

To a mixture of 4'-[2-[(tert-butoxycarbonyl)[(2R)-2-(6-chloro-3-pyridyl)-2-(tetrahydro-2H-pyran-2-yloxy)ethyl]amino]ethyl]-3-(cyclohexyloxy)-4-biphenylcarboxylic acid (180 mg) in N,N-dimethylformamide (2 ml) was added 1,1'-carbonyldiimidazole (51.6 mg) at room temperature and the mixture was stirred at the same temperature for 1 hour.

N-Ethylsulfamide (46.1 mg) and 1,8-diazabicyclo[5.4.0]-7-undecene (0.056 ml) were added to the mixture at room temperature. The mixture was stirred at room temperature for 0.5 hour and at 120° C. for 16 hours. The mixture was diluted with ethyl acetate, and washed with water, 0.5N hydrochloric acid and brine, and dried over sodium sulfate and evaporated under reduced pressure to give residue (220 mg). To a mixture of the above residue in methanol (3 ml) was added 4-methylbenzensulfonic acid (22 mg) at room temperature and the mixture was stirred at room temperature overnight. The mixture was diluted with ethyl acetate, and washed with water and brine, dried over sodium sulfate and evaporated under reduced pressure to give the residue. The residue was purified by column chromatography on silica gel (hexane/ethyl acetate=50/50) to give the residue (135 mg). To a mixture of the above residue and ammonium formate (118 mg) in methanol (2 ml) and water (0.2 ml) was added 10% palladium on carbon (50% wet, 25 mg) under nitrogen atmosphere. The mixture was refluxed for 30 minutes. The mixture was filtered through celite pad and the filtrate was evaporated under reduced pressure. The residue was purified by column chromatography (chloroform/methanol=95/5) to give tert-butyl [2-[3'-(cyclohexyloxy)-4'-[[[(ethylamino)sulfonyl]amino]carbonyl]-4-biphenylyl]ethyl][(2R)-2-hydroxy-2-(3-pyridyl)ethyl]carbamate (132 mg).

(−)ESI-MS (m/z): 665 (M−H)⁻

EXAMPLE 51

The following compound was obtained according to a similar manner to that of Example 41.

4'-[2-[[(2R)-2-(6-Chloro-3-pyridyl)-2-hydroxyethyl]amino]ethyl]-3-(cyclohexyloxy)-N-[(3-hydroxypropyl)sulfonyl]-4-biphenylcarboxamide hydrochloride NMR (200 MHz, DMSO-$d_6$, δ): 1.29-2.03 (12H, m), 3.02-3.33 (6H, m), 3.48-3.60 (4H, m), 4.02-4.38 (2H, m), 4.75-4.87 (1H, m), 5.13 (1H, dd, J=3.0, 9.5 Hz), 7.33-7.42 (4H, m), 7.57 (H, d, J=8.0 Hz), 7.71-7.76 (3H, m), 7.89 (1H, d, J=2.5 Hz), 8.46 (1H, d, J=2.5 Hz), 9.09 (1H, br s), 9.35 (1H, br s), 11.18 (1H, s)

(−)ESI-MS (m/z): 614 (M−H)⁻

EXAMPLE 52

To a solution of tert-butyl [2-[3'-(cyclohexyloxy)-4'-[[[(3-hydroxypropyl)sulfonyl]amino]carbonyl]-4-biphenylyl]ethyl][(2R)-2-hydroxy-2-(3-pyridyl)ethyl]-carbamate (110 mg) in 1,4-dioxane (1.5 ml) was added hydrogen chloride in 1,4-dioxane (4N, 1.5 ml) at room temperature and the mixture was stirred at the same temperature overnight. The mixture was evaporated under reduced pressure to give 3-(cyclohexyloxy)-N-[(3-hydroxypropyl)sulfonyl]-4'-[2-[[(2R)-2-hydroxy-2-(3-pyridyl)ethyl]amino]ethyl]-4-biphenylcarboxamide dihydrochloride (105 mg) as a white solid.

NMR (200 MHz, DMSO-$d_6$, δ): 1.35-2.02 (12H, m), 3.05-3.39 (6H, m), 3.48-3.60 (4H, m), 4.75-4.87 (1H, m), 5.27-5.35 (1H, m), 7.33-7.44 (4H, m), 7.71-7.75 (3H, m), 7.98 (1H, dd, J=5.5, 8.5 Hz), 8.49 (1H, d, J=8.5 Hz), 8.83-8.91 (2H, m), 9.30 (1H, br s), 9.41 (1H, br s), 11.18 (1H, s)

(−)ESI-MS (m/z): 580 (M−H)⁻

EXAMPLE 53

To a solution of tert-butyl [2-[3'-(cyclohexyloxy)-4'-[[[(2-methoxyethyl)sulfonyl]amino]carbonyl]-4-biphenylyl]ethyl][(2R)-2-hydroxy-2-(3-pyridyl)ethyl]carbamate (199 mg) in 1,4-dioxane (2.0 ml) was added hydrogen chloride in 1,4-dioxane (4N, 2.0 ml) at room temperature and the mixture was stirred at the same temperature 3 hours. The mixture was evaporated under reduced pressure to give 3-(cyclohexyloxy)-4'-[2-[[(2R)-2-hydroxy-2-(3-pyridyl)ethyl]amino]ethyl]-N-[(2-methoxyethyl)sulfonyl]-4-biphenylcarboxamide dihydrochloride (153 mg) as a white solid.

NMR (200 MHz, DMSO-$d_6$, δ): 1.31-2.04 (10H, m), 3.04-3.50 (6H, m), 3.23 (3H, s), 3.72-3.84 (4H, m), 4.78-4.89 (1H, m), 5.27-5.37 (1H, m), 7.34-7.45 (4H, m), 7.68-7.79 (3H, m), 8.00 (1H, dd, J=5.5, 8.4 Hz), 8.51 (1H, d, J=8.4 Hz), 8.83-8.92 (2H, m), 9.33 (1H, br s), 9.45 (1H, br s), 11.19 (1H, s)

(−)ESI-MS (m/z): 580 (M−H)⁻

EXAMPLE 54

To a solution of tert-butyl [(2R)-2-hydroxy-2-phenylethyl][2-[4'-[[[(3-hydroxypopyl)sulfonyl]amino]carbonyl]-3'-(isopropylthio)-4-biphenylyl]ethyl]carbamate (94 mg) in 1,4-dioxane (1.5 ml) was added hydrogen chloride in 1,4-dioxane (4N, 1.5 ml) at room temperature and the mixture was stirred at the same temperature overnight. The mixture was evaporated under reduced pressure to give 4'-[2-[[(2R)-2-hydroxy-2-phenylethyl]amino]ethyl]-N-[(3-hydroxypropyl)sulfonyl]-3-(isopropylthio)-4-biphenylcarboxamide hydrochloride (75 mg) as a white solid.

NMR (200 MHz, DMSO-$d_6$, δ): 1.25 (6H, d, J=6.5 Hz), 1.85-1.99 (2H, m), 3.02-3.27 (6H, m), 3.49-3.58 (4H, m), 3.62-3.72 (1H, m), 4.76 (1H, br s), 4.95-5.04 (1H, m), 6.23 (1H, d, J=4 Hz), 7.31-7.42 (7H, m), 7.55-7.64 (2H, m), 7.70-7.74 (3H, m), 8.92 (1H, br s), 9.26 (1H, br s), 12.14 (1H, s)

(−)ESI-MS (m/z): 555 (M−H)⁻

EXAMPLE 55

To a solution of 3-(cyclohexyloxy)-N-[(3-hydroxypropyl)sulfonyl]-4'-[2-[[(2R)-2-hydroxy-2-(3-pyridyl)ethyl]amino]ethyl]-4-biphenylcarboxamide dihydrochloride (1.2 g) in water (5 ml) was added 1N sodium hydroxide aqueous solution (3.7 ml). The obtained solid was filtrated and then followed by crystallization from isopropyl alcohol to give 3-(cyclohexyloxy)-N-[(3-hydroxypropyl)sulfonyl]-4'-[2-[[(2R)-2-hydroxy-2-(3-pyridyl)ethyl]amino]ethyl]-4-biphenylcarboxamide (1.0 g).

NMR (200 MHz, DMSO-$d_6$, δ): 1.30-2.00 (12H, m), 2.80-3.10 (6H, m), 3.40-3.60 (4H, m), 4.51 (1H, m), 4.85 (1H, m), 7.10-7.40 (5H, m), 7.48 (1H, d, J=8 Hz), 7.60 (1H, d, J=8 Hz), 7.76 (1H, d, J=8 Hz), 8.47 (1H, m), 8.57 (1H, s)

(+)ESI-MS (m/z): 582 (M+H)⁺

EXAMPLE 56

The following compound was obtained according to a similar manner to that of Example 55.

3-(Cyclohexyloxy)-N-[(3-hydroxypropyl)sulfonyl]-4'-[3-[[(2R)-2-hydroxy-2-(3-pyridyl)ethyl]amino]propyl]-4-biphenylcarboxamide NMR (200 MHz, DMSO-$d_6$, δ): 1.30-2.00 (14H, m), 2.80-3.60 (10H, m), 4.53 (1H, m), 4.87 (1H, m), 7.10-7.40 (5H, m), 7.49 (1H, d, J=8 Hz), 7.60 (1H, d, J=8 Hz), 7.79 (1H, d, J=8 Hz), 8.47 (1H, m), 8.57 (1H, s)

(+)ESI-MS (m/z): 596 (M+H)$^+$

The invention claimed is:

1. A compound of formula [I] or salt thereof:

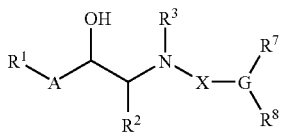

wherein

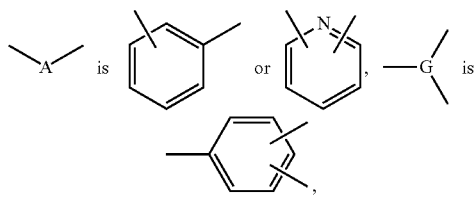

$R^1$ is hydrogen, halogen, nitro, or amino,
$R^2$ is hydrogen or lower alkyl,
$R^3$ is hydrogen,
—X— is

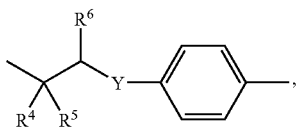

in which —Y— is a bond, —O—, —NH—, or —CH$_2$—, and
$R^4$, $R^5$, and $R^6$ are each hydrogen,
$R^7$ is lower alkyl, cyclo(lower)alkyl, —Z—R$^9$, or

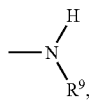

in which —Z— is —O— or —S—, and
each $R^9$ is independently lower alkyl or cyclo(lower)alkyl, and $R^8$ is -D-E-R$^{10}$, in which
-D- is —CONHSO$_2$—,
E is lower alkylene selected from the group consisting of ethylene, trimethylene, 2,2-dimethyltrimethylene, 3,3-dimethyltrimethylene, tetramethylene, pentamethylene, hexamethylene and propylene, and $R^{10}$ is —OH.

2. A pharmaceutical composition which comprises, as an active ingredient, a compound of claim 1 or a pharmaceutically acceptable salt thereof in admixture with a pharmaceutically acceptable carrier or excipient.

3. A compound or salt thereof, which is selected from the group consisting of (1) 4'-[2-[[(2R)-2-hydroxy-2-phenylethyl]amino]ethyl]-N-[(3-hydroxypropyl)sulfonyl]-3-isopropoxy-4-biphenyl-carboxamide, (2) 4'-[2-[[(2R)-2-hydroxy-2-phenylethyl]amino]ethyl]-N-[(3-hydroxypropyl)sulfonyl]-3-(isopropylthio)-4-biphenylcarboxamide, (3) 3-(cyclohexyloxy)-4'-[2-[[(2R)-2-hydroxy-2-phenylethyl]amino]ethyl]-N-[(3-hydroxypropyl)sulfonyl]-4-biphenylcarboxamide, (4) 3-(cyclohexyloxy)-N-[(3-hydroxypropyl)sulfonyl]-4'-[2-[[(2R)-2-hydroxy-2-(3-pyridyl) ethyl]amino]ethyl]-4-biphenylcarboxamide, (5) 3-(cyclohexyloxy)-N-[(2-hydroxyethyl)sulfonyl]-4'-[2-[[(2R)-2-hydroxy-2-(3-pyridyl)ethyl]amino]ethyl]-4-biphenylcarboxamide, (6) N-[(3-hydroxypropyl)sulfonyl]-4'-[2-[[(2R)-2-hydroxy-2-(3-pyridyl) ethyl]amino]ethyl]-3-isopropoxy-4-biphenylcarboxamide, (7) 3-(cyclohexyloxy)-N-[(2-hydroxyethyl)sulfonyl]-4'-[2-[[(2R)-2-hydroxy-2-phenylethyl]amino]ethyl]-4-biphenylcarboxamide, (8) N-[(3-hydroxypropyl)sulfonyl]-4'-[2-[[(2R)-2-hydroxy-2-(3-pyridyl) ethyl]amino]ethyl]-3-propoxy-4-biphenylcarboxamide, (9) 3-cyclopentyl-4'-[2-[[(2R)-2-hydroxy-2-phenylethyl]amino]ethoxy]-N-[(3-hydroxypropyl)sulfonyl]-4-biphenylcarboxamide,

(10) 4'-[2-[[(2R)-2-(4-aminophenyl)-2-hydroxyethyl]amino]ethyl]-N-[(3-hydroxypropyl) sulfonyl]-3-isobutyl-4-biphenylcarboxamide,

(11) 4'-[2-[[(2R)-2-(4-aminophenyl)-2-hydroxyethyl]amino]ethoxy]-3-(cyclohexyloxy) -N-[(3-hydroxypropyl)sulfonyl]-4-biphenylcarboxamide,

(12) 3-(cycloheptyloxy)-N-[(3-hydroxypropyl)sulfonyl]-4'-[2-[[(2R)-2-hydroxy-2-(3-pyridyl)ethyl]amino]ethyl]-4-biphenylcarboxamide,

(13) 3-(cyclohexyloxy)-N-[(2-hydroxyethyl)sulfonyl]-4'-[2-[[(1S,2R)-2-hydroxy-1-methyl-2-phenylethyl]amino]ethyl]-4-biphenylcarboxamide,

(14) 3-(cyclohexylamino)-4'-[2-[[(2R)-2-hydroxy-2-phenylethyl]amino]ethoxy]-N -[(3-hydroxypropyl)sulfonyl]-4-biphenylcarboxamide,

(15) 3-(cyclohexyloxy)-N-[(3-hydroxypropyl)sulfonyl]-4'-[3-[[(2R)-2-hydroxy-2-(3-pyridyl)ethyl]amino]propyl]-4-biphenylcarboxamide,

(16) N-[(3-hydroxypropyl)sulfonyl]-4'-[3-[[(2R)-2-hydroxy-2-(3-pyridyl)ethyl]amino]propyl]-3-isobutoxy-4-biphenylcarboxamide,

(17) 3-(cyclohexyloxy)-N-[(3-hydroxy-3-methylbutyl) sulfonyl]-4'-[2-[[(2R)-2-hydroxy-2-phenylethyl]amino]ethyl]-4-biphenylcarboxamide,

(18) 3-(cyclohexyloxy)-4'-[2-[[(2R)-2-(3-fluorophenyl)-2-hydroxyethyl]amino]ethyl]-N-[(3-hydroxypropyl) sulfonyl]-4-biphenylcarboxamide,

(19) 4'-[[2-[[(2R)-2-(3-chlorophenyl)-2-hydroxyethyl]amino]ethyl]amino]-N-[(3-hydroxypropyl)sulfonyl]-3-isobutoxy-4-biphenylcarboxamide, and pharmaceutically acceptable salts thereof.

4. A pharmaceutical composition which comprises, as an active ingredient, a compound of claim 3 or a pharmaceutically acceptable salt thereof in admixture with a pharmaceutically acceptable carrier or excipient.

5. The compound of claim 1, wherein the compound is 4'-[2-[[(2R)-2-hydroxy-2-phenylethyl]amino]ethyl]-N-[(3-hydroxypropyl)sulfonyl]-3-isopropoxy-4-biphenyl-carboxamide or a salt thereof.

6. The compound of claim 1, wherein the compound is 4'-[2-[[(2R)-2-hydroxy-2-phenylethyl]amino]ethyl]-N-[(3-hydroxypropyl)sulfonyl]-3-(isopropylthio) -4-biphenylcarboxamide or a salt thereof.

7. The compound of claim 1, wherein the compound is 3-(cyclohexyloxy)-4'-[2-[[(2R)-2-hydroxy-2-phenylethyl]amino]ethyl]-N-[(3-hydroxypropyl) sulfonyl]-4-biphenylcarboxamide or a salt thereof.

8. The compound of claim 1, wherein the compound is 3-(cyclohexyloxy)-N-[(3-hydroxypropyl)sulfonyl]-4'-[2-[[(2R)-2-hydroxy-2-(3-pyridyl) ethyl]amino]ethyl]-4-biphenylcarboxamide or a salt thereof.

9. The compound of claim 1, wherein the compound is 3-(cyclohexyloxy)-N-[(2-hydroxyethyl)sulfonyl]-4'-[2-[[(2R)-2-hydroxy-2-(3-pyridyl) ethyl]amino]ethyl]-4-biphenylcarboxamide or a salt thereof.

10. The compound of claim 1, wherein the compound is N-[(3-hydroxypropyl)sulfonyl]-4'-[2-[[(2R)-2-hydroxy-2-(3-pyridyl)ethyl]amino]ethyl]-3-isopropoxy-4-biphenylcarboxamide or a salt thereof.

11. The compound of claim 1, wherein the compound is 3-(cyclohexyloxy)-N-[(2-hydroxyethyl)sulfonyl]-4'-[2-[[(2R)-2-hydroxy-2-phenylethyl]amino]ethyl]-4-biphenylcarboxamide or a salt thereof.

12. The compound of claim 1, wherein the compound is N-[(3-hydroxypropyl)sulfonyl]-4'-[2-[[(2R)-2-hydroxy-2-(3-pyridyl)ethyl]amino]ethyl]-3-propoxy-4-biphenylcarboxamide or a salt thereof.

13. The compound of claim 1, wherein the compound is 3-cyclopentyl-4'-[2-[[(2R)-2-hydroxy-2-phenylethyl]amino]ethoxy]-N-[(3-hydroxypropyl) sulfonyl]-4-biphenylcarboxamide or a salt thereof.

14. The compound of claim 1, wherein the compound is 4'-[2-[[(2R)-2-(4-aminophenyl)-2-hydroxyethyl]amino]ethyl]-N-[(3-hydroxypropyl) sulfonyl]-3-isobutyl-4-biphenylcarboxamide or a salt thereof.

15. The compound of claim 1, wherein the compound is 4'-[2-[[(2R)-2-(4-aminophenyl)-2-hydroxyethyl]amino]ethoxy]-3-(cyclohexyloxy)-N-[(3-hydroxypropyl)sulfonyl]-4-biphenylcarboxamide or a salt thereof.

16. The compound of claim 1, wherein the compound is 3-(cycloheptyloxy)-N-[(3-hydroxypropyl)sulfonyl]-4'-[2-[[(2R)-2-hydroxy-2-(3-pyridyl) ethyl]amino]ethyl]-4-biphenylcarboxamide or a salt thereof.

17. The compound of claim 1, wherein the compound is 3-(cyclohexyloxy)-N-[(2-hydroxyethyl)sulfonyl]-4'-[2-[[(1S,2R)-2-hydroxy-1-methyl-2-phenylethyl]amino]ethyl]-4-biphenylcarboxamide or a salt thereof.

18. The compound of claim 1, wherein the compound is 3-(cyclohexylamino)-4'-[2-[[(2R)-2-hydroxy-2-phenylethyl]amino]ethoxy]-N-[(3-hydroxypropyl) sulfonyl]-4-biphenylcarboxamide or a salt thereof.

19. The compound of claim 1, wherein the compound is 3-(cyclohexyloxy)-N-[(3-hydroxypropyl)sulfonyl]-4'-[3-[[(2R)-2-hydroxy-2-(3-pyridyl) ethyl]amino]propyl]-4-biphenylcarboxamide or a salt thereof.

20. The compound of claim 1, wherein the compound is N-[(3-hydroxypropyl)sulfonyl]-4'-[3-[[(2R)-2-hydroxy-2-(3-pyridyl)ethyl]amino]propyl]-3-isobutoxy-4-biphenylcarboxamide or a salt thereof.

21. The compound of claim 1, wherein the compound is 3-(cyclohexyloxy)-N-[(3-hydroxy-3-methylbutyl)sulfonyl]-4'-[2-[[(2R)-2-hydroxy-2-phenylethyl]amino]ethyl]-4-biphenylcarboxamide or a salt thereof.

22. The compound of claim 1, wherein the compound is 3-(cyclohexyloxy)-4'-[2-[[(2R)-2-(3-fluorophenyl)-2-hydroxyethyl]amino]ethyl]-N-[(3-hydroxypropyl)sulfonyl]-4-biphenylcarboxamide or a salt thereof.

23. The compound of claim 1, wherein the compound is 4'-[[2-[[(2R)-2-(3-chlorophenyl)-2-hydroxyethyl]amino]ethyl]amino]-N-[(3-hydroxypropyl) sulfonyl]-3-isobutoxy-4-biphenylcarboxamide or a salt thereof.

24. The compound of claim 1, wherein E is lower alkylene selected from the group consisting of ethylene, 2,2-dimethyltrimethylene, 3,3-dimethyltrimethylene, tetramethylene, pentamethylene, hexamethylene and propylene.

25. The compound of claim 1, wherein E is lower alkylene selected from the group consisting of ethylene, trimethylene, 2,2-dimethyltrimethylene, 3,3-dimethyltrimethylene, tetramethylene, pentamethylene, and hexamethylene.

26. The compound of claim 1, wherein E is trimethylene.

27. The compound of claim 1, wherein E is propylene.

\* \* \* \* \*